United States Patent
Yang

(10) Patent No.: US 10,751,396 B2
(45) Date of Patent: Aug. 25, 2020

(54) EARLY HYPERLIPIDEMIA PROMOTES ENDOTHELIAL ACTIVATION VIA A CASPASE-1-SIRTUIN 1 PATHWAY

(71) Applicant: Temple University—Of The Commonwealth System of Higher Education, Philadelphia, PA (US)

(72) Inventor: Xiaofeng Yang, Huntingdon Valley, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 38 days.

(21) Appl. No.: 15/547,137

(22) PCT Filed: Feb. 1, 2016

(86) PCT No.: PCT/US2016/015964
§ 371 (c)(1),
(2) Date: Jul. 28, 2017

(87) PCT Pub. No.: WO2016/123615
PCT Pub. Date: Aug. 4, 2016

(65) Prior Publication Data
US 2018/0015152 A1 Jan. 18, 2018

Related U.S. Application Data

(60) Provisional application No. 62/109,918, filed on Jan. 30, 2015.

(51) Int. Cl.
| | | |
|---|---|---|
| *A61K 38/00* | (2006.01) | |
| *A61K 38/50* | (2006.01) | |
| *A61K 31/7088* | (2006.01) | |
| *C12N 15/00* | (2006.01) | |
| *C07K 14/47* | (2006.01) | |
| *A61K 39/395* | (2006.01) | |
| *C12N 9/80* | (2006.01) | |

(52) U.S. Cl.
CPC .......... *A61K 38/50* (2013.01); *A61K 31/7088* (2013.01); *A61K 39/395* (2013.01); *C07K 14/4703* (2013.01); *C07K 14/4747* (2013.01); *C12N 9/80* (2013.01); *C12N 15/00* (2013.01); *C12Y 305/01* (2013.01)

(58) Field of Classification Search
None
See application file for complete search history.

(56) References Cited

U.S. PATENT DOCUMENTS

| | | |
|---|---|---|
| 2005/0222034 A1 | 10/2005 | Hsu |
| 2010/0137345 A1 | 6/2010 | Leo et al. |
| 2010/0210692 A1 | 8/2010 | Farmer et al. |
| 2012/0329721 A1 | 12/2012 | Chauvier et al. |
| 2014/0314746 A1 | 10/2014 | Artlett et al. |

OTHER PUBLICATIONS

Yin et al., 2009, Inflammasomes are differentially expressed in cardiovascular and other tissues, Int J Immunopathol Pharmacol 22:311-22.
Yin et al., 2013, Inflammasomes: sensors of metabolic stresses for vascular inflammation, Front Biosci 18:638-49.
Shen et al., 2010, Caspase-1 recognizes extended cleavage sites in its natural substrates, Atherosclerosis 201:422-9.
Zhang et al., 2008, Endothelium-specific overexpression of class III deacetylase SIRT1 decreases atherosclerosis in apolipoprotein E-deficient mice, Cardiovasc Res 80:191-9.
Zhang et al., 2010, SIRT1 Suppresses Activator Protein-1 Transcriptional Activity and Cyclooxygenase-2 Expression in Macrophages, J Biol Chem 285:7097-10.
Yang et al., 2012, SIRT1 Activators Suppress Inflammatory Responses through Promotion of p65 Deacetylation and Inhibition of NF-kB Activity, PLoS One 7:e46364.
Usui et al., 2012, Critical role of caspase-1 in vascular inflammation and development of atherosclerosis in Western diet-fed apolipoprotein E-deficient mice, Biochem Biophys Res Commun 425:162-8.
Stein et al., 2010, SIRT1 reduces endothelial activation without affecting vascular function in ApoE-/- mice, Aging 2:353-60.
Yin et al., 2015, Early Hyperlipidemia Promotes Endothelial Activation via a Caspase-1-Sirtuin 1 Pathway, Arterioscler Thromb Vasc Biol, 35(4), 804-16.
Potente et al., 2007, SIRT1 controls endothelial angiogenic functions during vascular growth, Genes Dev, 21(20), 2644-58.
Chalkiadaki et al., 2012, High-Fat Diet Triggers Inflammation-Induced Cleavage of SIRT1 in Adipose Tissue to Promote Metabolic Dysfunction, Cell Metab, 16(2), 180-8.

*Primary Examiner* — Thomas S Heard
(74) *Attorney, Agent, or Firm* — Riverside Law LLP

(57) ABSTRACT

The present invention provides compositions and methods for treating or preventing a disease or disorder associated with endothelial activation, inflammation or atherogenesis, including but not limited to cardiovascular diseases and inflammatory disorders.

1 Claim, 34 Drawing Sheets
Specification includes a Sequence Listing.

A.
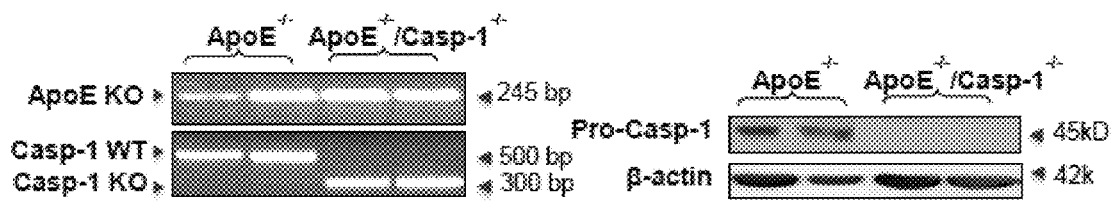
B.
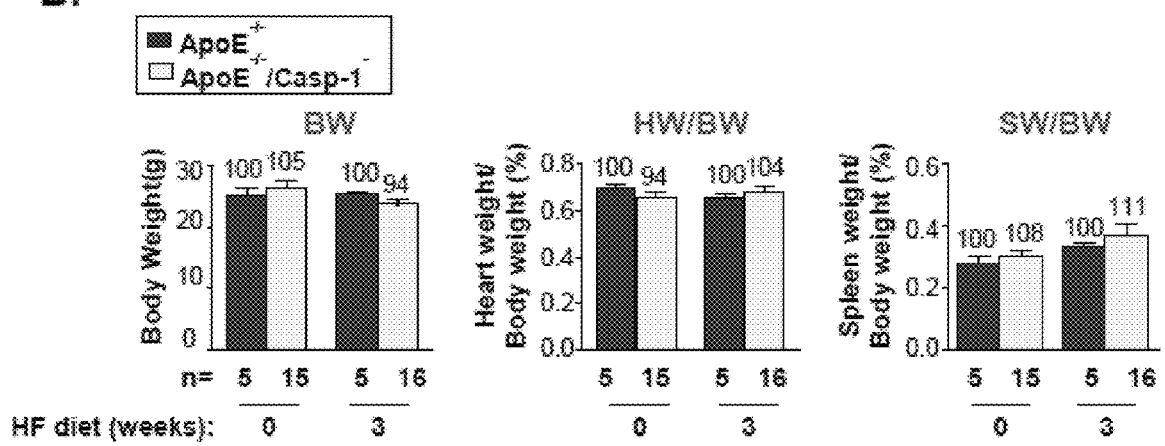
C.
|  | Cholesterol (mg/dl) | | Triglyceride (mg/dl) | |
| --- | --- | --- | --- | --- |
|  | Normal Chow | HF3w | Normal Chow | HF3w |
| ApoE$^{-/-}$ | 220 ± 67.5 (n=6) | 587 ± 120.5 (n=3) | 257.2 ± 55.5 | 289 ± 13.7 |
| ApoE$^{-/-}$/Casp-1$^{-/-}$ | 320.4 ± 64.6 (n=5) | 623.25 ± 85.5 (n=4) | 303 ± 28.2 | 328 ± 99.3 |
($P>0.05$, no statistical differences between the groups)
Figures 2A – 2C

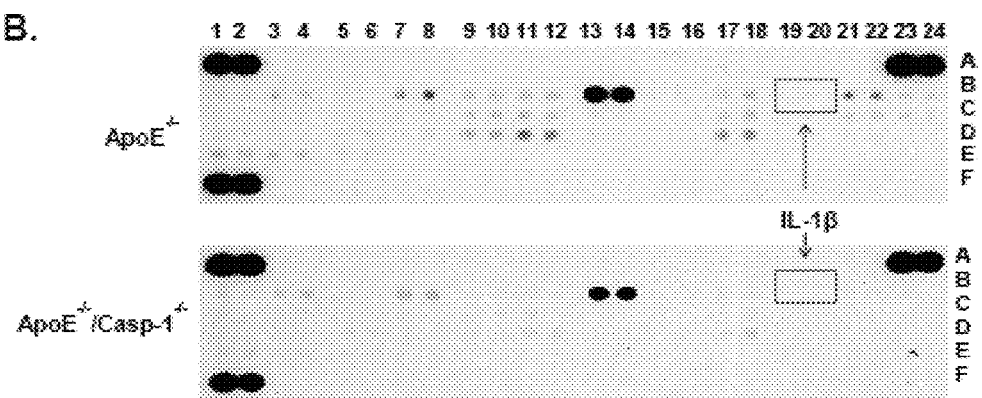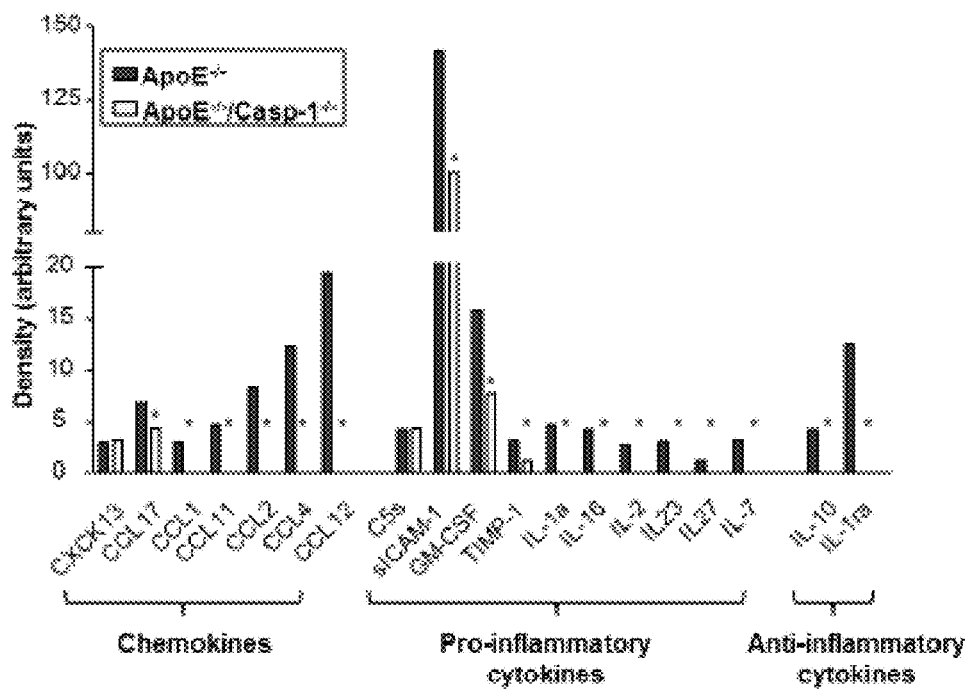
Figures 9A – 9C

A.
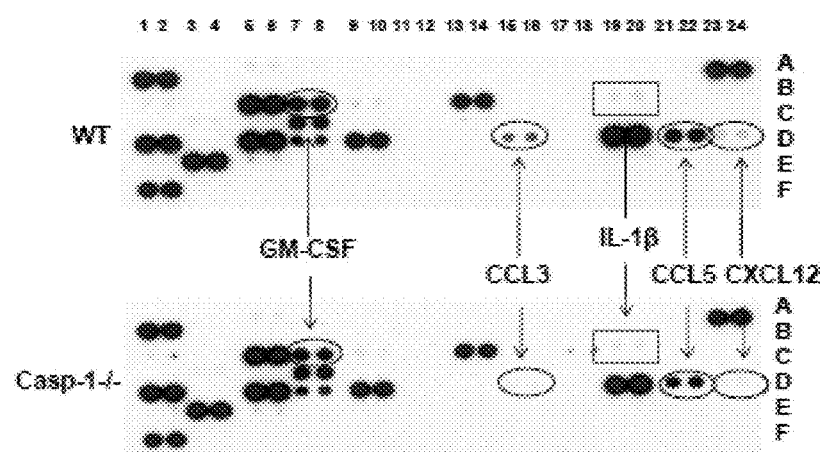
B.
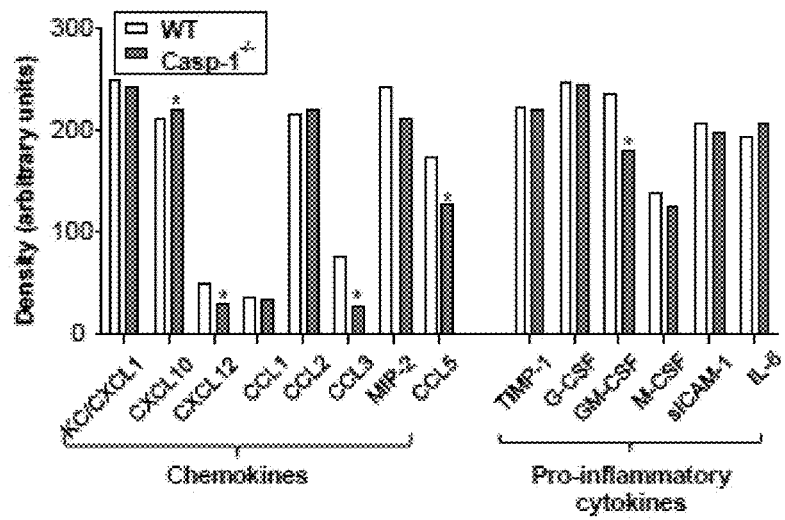
Figures 11A – 11C

A

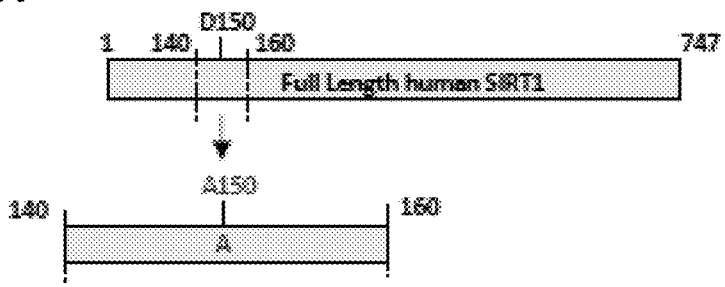

B

```
  1   MADEVALALQAAGSPSAAAA-MEAASQPADEPLRKRPRRDGPGLGRSPGEPSAA-----V   54
      MADE ALALQ  GSPSAA A  EAAS PA EPLRKRPRRDGPGL RSPGEP  A     V
  1   MADEAALALQPGGSPSAAGADREAASSPAGEPLRKRPRRDGPGLERSPGEPGGAAPEREV   60

55   APAAAGCEAASAAAPAALWREAAGAAASAEREAPATAVAGDGDNGSGLR---REPRAADD  111
      AA GC  A+AAA        A AA   +   ATA AG+GDNG GL+    REP  AD+
 61   PAAARGCPGAAAAALWREAEAEAAAAGGEQEAQ-ATAAAGEGDNGPGLQGPSREPPLADN  119
```

Mouse SIRT1
```
112   FDDDEGEEEDEAAAAAAAAAIGYRDNLLLTDGLLTNGFHSCESDDQDRTSHASSSDWTPR  171
      D++ ++E E     AAAAAIGYRDNLL  D ++TNGFHSCESD++DR SHASSSDWTPR
```
Human SIRT1
```
120   LYDEDDDDEGEEEEEAAAAAIGYRDNLLFGDELITNGFHSCESDEEDRASHASSSDWTPR  179

172   PRIGPYTFVQQHLMIGTDPRTILKDLLPETIPPPELDDMTLWQIVINILSEPPKRKKRKD  231
      PRIGPYTFVQQHLMIGTDPRTILKDLLPETIPPPELDDMTLWQIVINILSEPPKRKKRKD
180   PRIGPYTFVQQHLMIGTDPRTILKDLLPETIPPPELDDMTLWQIVINILSEPPKRKKRKD  239

232   INTIEDAVKLLQECKKIIVLTGAGVSVSCGIPDFRSRDGIYARLAVDFPDLPDPQAMFDI  291
      INTIEDAVKLLQECKKIIVLTGAGVSVSCGIPDFRSRDGIYARLAVDFPDLPDPQAMFDI
240   INTIEDAVKLLQECKKIIVLTGAGVSVSCGIPDFRSRDGIYARLAVDFPDLPDPQAMFDI  299

292   EYFRKDPRPFFKFAKEIYPGQFQPSLCHKFIALSDKEGKLLRNYTQNIDTLEQVAGIQRI  351
      EYFRKDPRPFFKFAKEIYPGQFQPSLCHKFIALSDKEGKLLRNYTQNIDTLEQVAGIQRI
300   EYFRKDPRPFFKFAKEIYPGQFQPSLCHKFIALSDKEGKLLRNYTQNIDTLEQVAGIQRI  359

352   LQCHGSFATASCLICKYKVDCEAVRGDIFNQVVPRCPRCPADEPLAIMKPEIVFFGENLP  411
      +QCHGSFATASCLICKYKVDCEAVRGDIFNQVVPRCPRCPADEPLAIMKPEIVFFGENLP
360   IQCHGSFATASCLICKYKVDCEAVRGDIFNQVVPRCPRCPADEPLAIMKPEIVFFGENLP  419

412   EQFHRAMKYDKDEVDLLIVIGSSLKVRPVALIPSSIPHEVPQILINREPLPHLHFDVELL  471
      EQFHRAMKYDKDEVDLLIVIGSSLKVRPVALIPSSIPHEVPQILINREPLPHLHFDVELL
420   EQFHRAMKYDKDEVDLLIVIGSSLKVRPVALIPSSIPHEVPQILINREPLPHLHFDVELL  479

472   GDCDVIINELCHRLGGEYAKLCCNPVKLSEITEKPPRPQKELVHLSELPPTPLHISEDSS  531
      GDCDVIINELCHRLGGEYAKLCCNPVKLSEITEKPPR QKEL +LSELPPTPLH+SEDSS
480   GDCDVIINELCHRLGGEYAKLCCNPVKLSEITEKPPRTQKELAYLSELPPTPLHVSEDSS  539

532   SPERTVPQDSSVIATLVDQATNNNVNDLEVSES-SCVEEKPQEVQTSRNVERI--NVENP  588
      SPERT P  DSSVI TL+DQA +N +DL+VSES  C+EEKPQEVQTSRNVE+I   +ENP
540   SPERTSPPDSSVIVTLLDQAAKSN-DDLDVSESKGCMEEKPQEVQTSRNVESIAEQMENP  598

589   DFKAVGSSTADKNERTSVAETVRKCWPNRLAKEQISKRLEGNQYLFVPPNRYIFHGAEVY  648
      D K VGSST +KNERTSVA TVRKCWPNR+AKEQIS+RL+GN+YLF PPNRYIFHGAEVY
599   DLKNVGSSTGEKNERTSVAGTVRKCWPNRVAKEQISRRLIGNQYLFLPPNRYIFHGAEVY  658

649   SDSEDDVLSSSSCGSNSDSGTCQSPSLEEPLEDESEIEEFYNGLEDDTERPECAGGSGFG  708
      SDSEDDVLSSSSCGSNSDSGTCQSPSLEEP+EDESEIEEFYNGLED+ + PE AGG+GFG
659   SDSEDDVLSSSSCGSNSDSGTCQSPSLEEPMEDESEIEEFYNGLEDEPDVPERAGGAGFG  718

709   ADGGDQEVVNEAIATRQELTDVNYPSDKS   737 (SEQ ID NO: 33)
       DG DQE +NEAI+ +QE+TD+NYPS+KS
719   TDGDDQEAINEAISVKQEVTDMNYPSNKS   747 (SEQ ID NO: 34)
```

| Species | Casp1 Cleavage Site |
|---|---|
| Mouse SIRT1 | D142 (Chalkiadaki, A et al., Cell Metab, 2012) |
| Human SIRT1 | D150 (BLAST search and conformation by previously published method: Shen, J et al., Atherosclerosis, 2008 |

Figures 12A – 12B

A.
Caspase-1 depletion increases VEGFR-2 expression
| Gene | Dataset (GSE25205) WT vs. Casp1 KO | | | | |
|---|---|---|---|---|---|
| | WT Value | Casp1KO Value | ΔValue | Fold Change | p value |
| VEGFR-2 | | | | | |
| Vegfr-2 (Flk1/Kdr) | 7.97 | 8.66 | -0.68 | 0.62 | 0.01021 |
| Caspase-1 Activation Complex | | | | | |
| Casp1 | 9.32 | 4.85 | 4.47 | 22.23 | 0.00000 |
| Caspase-1 Related Cytokines | | | | | |
| IL-1β | 3.96 | 4.17 | -0.20 | 0.87 | 0.23650 |
| IL-18 | 7.99 | 8.14 | -0.16 | 0.90 | 0.37939 |
| House keeping genes | | | | | |
| Gapdh | 12.47 | 12.54 | -0.07 | 0.95 | 0.55139 |
| Nono | 11.23 | 11.13 | 0.10 | 1.07 | 0.98092 |
| Aldoa | 12.58 | 12.64 | -0.06 | 0.96 | 0.90721 |
B.
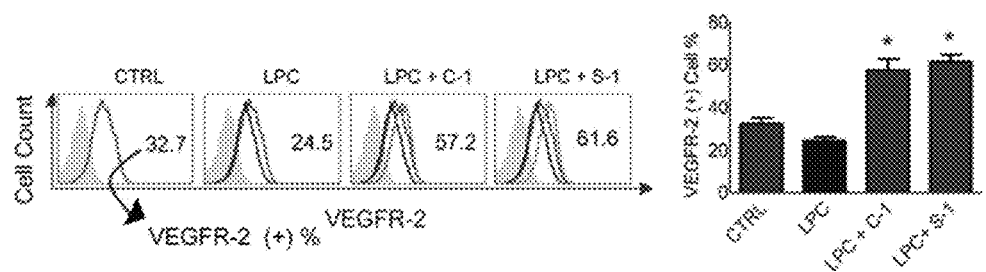
C.
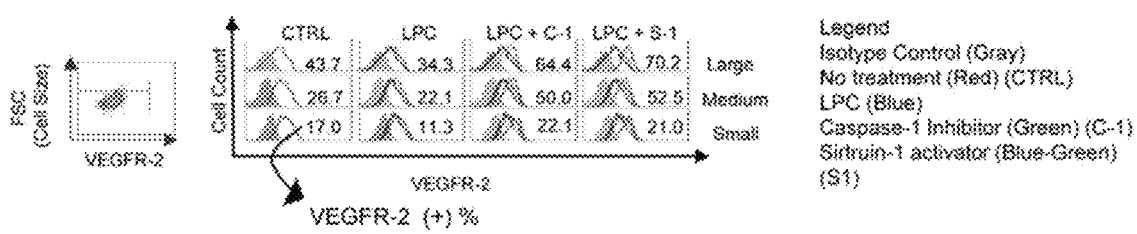
D.
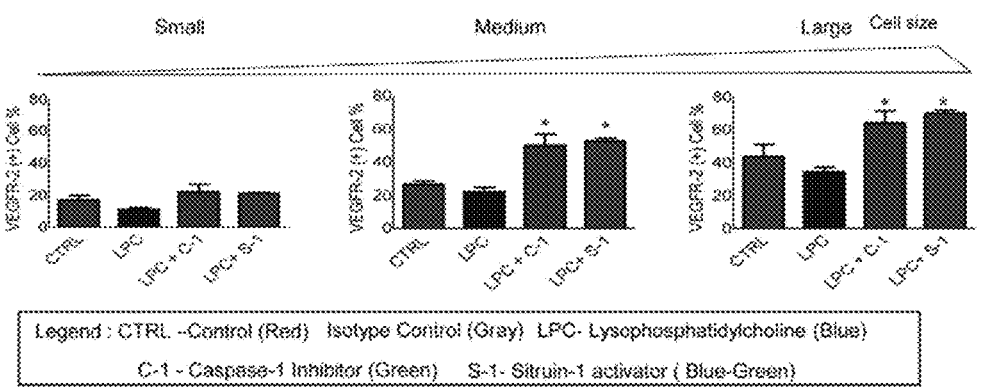
Figures 17A – 17D

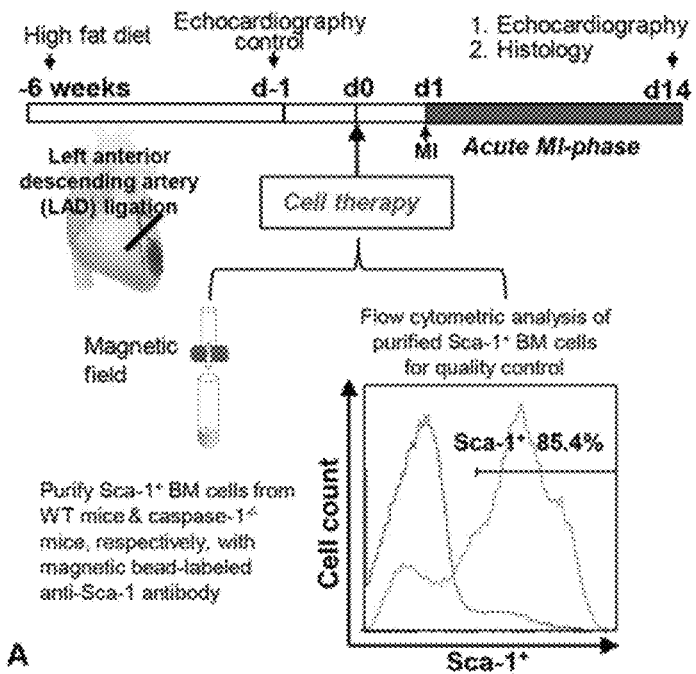
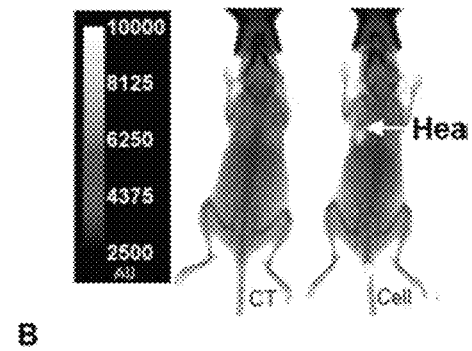
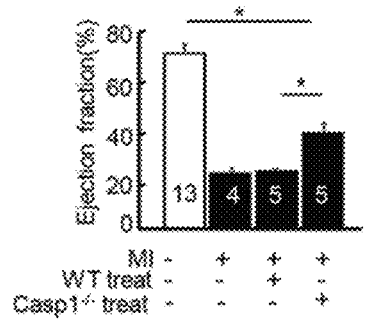
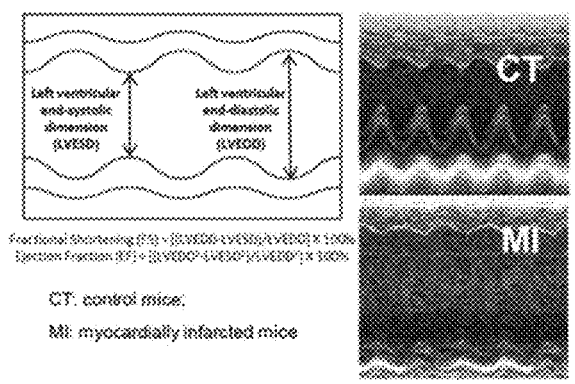
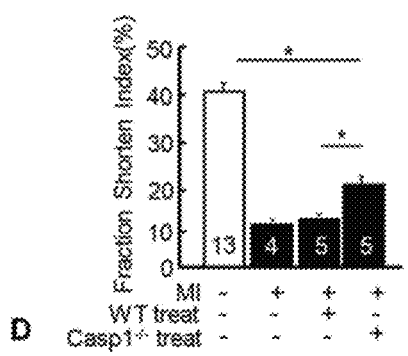
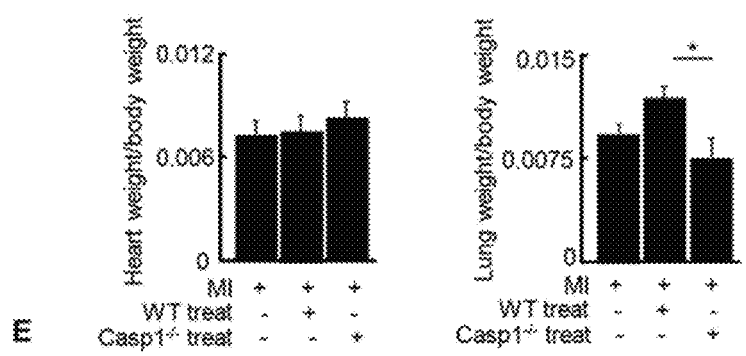
Figures 25A – 25E

A.

| Genes | Dataset (GSE25205) WT Vs. Casp1 -/- | |
|---|---|---|
| | Fold Change | P.Value |
| Casp1 (Caspase 1) | 22.23 | 2.59E-07 |
| Itgav (Integrin alpha V) | 1.53 | 0.0247 |
| Vtn (Vitronectin) | -1.19 | 0.1910 |
| Housekeeping Genes (HG) | | |
| Gapdh | 1.12 | 0.3250 |
| Aldoa | 1.03 | 0.6990 |
| Nono | 1.07 | 0.2760 |
| Confidence Interval of HG | 1.07 ±0.08 | |

(# analyzed from the microarray data set GSE25205 from epididymal white adipose in the NIH -Geo Database)

EARLY HYPERLIPIDEMIA PROMOTES ENDOTHELIAL ACTIVATION VIA A CASPASE-1-SIRTUIN 1 PATHWAY

CROSS-REFERENCE TO RELATED APPLICATIONS

This application is the U.S. national phase application filed under 35 U.S.C. § 371 claiming benefit to International Patent Application No. PCT/US 16/15964, filed Feb. 1, 2016, which is entitled to priority under 35 U.S.C. § 119(e) to U.S. Provisional Patent Application No. 62/109,918 filed Jan. 30, 2015, the contents of which are each incorporated herein by reference in their entirety.

STATEMENT REGARDING FEDERALLY SPONSORED RESEARCH OR DEVELOPMENT

This invention was made with government support under RO1 HL 094451-01A1 and RO1 HL 108910-01, awarded by the National Institutes of Health (NIH). The government has certain rights in the invention.

BACKGROUND OF THE INVENTION

Hyperlipidemia, a risk factor for cardiovascular disease, is defined as pathologically elevated plasma concentrations of cholesterol and other lipids, which are commonly found in patients with atherosclerosis (Libby et al., 2011, Nature 473:317-25). It has been reported that hyperlipidemia, proinflammatory mediators, and other risk factors promote endothelial cell (EC) activation and atherosclerosis via several mechanisms, which include inducing endothelial activation and injury (Mestas and Ley, 2008, Trends Cardiovasc Med 18:228-32; Jiang et al., 2005, Arterioscler Thromb Vasc Biol 24:2515-21), increasing monocyte recruitment and differentiation (Zhang et al., 2009, Circulation 120:1893-902; Combadière et al., 2008, Circulation 117:1649-57), and decreasing regulatory T cell population (Xiong et al., 2009, Atherosclerosis. 203:401-8: Ait-Oufella et al., 2006, Nat Med 12:178-80).

ECs that line the inner surface of vessel wall are the first cells exposed to metabolite-related endogenous danger signals in the circulatory system (Libby et al., 2011, Nature 473:317-25). Endothelial activation is, therefore, defined as the initial event responsible for monocyte recruitment in atherogenesis (Chowienczyk et al., 1992, Lancet 340:1430-2). However, questions such as how hyperlipidemia can be sensed by ECs and how hyperlipidemia-induced vascular inflammation is initiated remain largely unanswered.

The cellular receptors, which can recognize the risk factors for atherogenesis, such as hyperlipidemia, have been under intensive search. The role of receptors for pathogen-associated molecular patterns has been characterized recently as bridging innate immune sensory systems for exogenous infectious agents and endogenous metabolic danger signals associated molecular patterns (DAMPs) to initiation of inflammation (Yang et al., 2008, Drug Discov Today Ther Strateg 5:125-42). The toll-like receptors, mainly located in the plasma membrane, recognize a variety of conserved microbial pathogen-associated molecular patterns and metabolic DAMPs and promote inflammatory gene transcription. As we described previously (Yin et al., 2009, Int J Immunopathol Pharmacol 22:311-22), for inflammation-privileged tissues in which inflammasome component genes are not constitutively expressed, toll-like receptors also work in synergy with cytosolic sensing receptor families, including nod-like receptors (NLRs; NOD [nucleotide binding and oligomerization domain]-like receptors) in recognizing endogenous DAMPs and in mediating upregulation and activation of a range of inflammatory genes (Yin et al., 2013, Front Biosci 18:638-49). Caspase-1, a member of the cysteine protease family of caspases, is present in the cell cytosol as pro-caspase-1, an inactive zymogen, and requires the assembly of an NLR family member-containing protein complex called inflammasome for activation. Activated caspase-1 is required for cleaving/processing pro-interleukin-1β (IL-1β) and pro-IL-18 into mature proinflammatory cytokines IL-1β and IL-18, respectively, and activation of other inflammatory pathways. However, it remains unclear whether in early atherosclerosis, the caspase-1-inflammasome pathway in ECs can sense elevated lipids as a DAMP and promote endothelial activation.

Previous reports showed that cholesterol crystals activate NLRP3 inflammasome in macrophages (Duewell et al., 2010, Nature 464:1357-61; Rajamäki, 2010, PLoS One 5:e11765), suggesting that NLRP3 inflammasome in macrophages can sense cholesterol crystals formed in advanced stage of atherosclerosis (Lim et al., 2011, J Limpid Res 52:2177-86). However, monocyte migration into the aorta after 3 weeks of high fat (HF) diet feeding is detected in atherosclerotic apolipoprotein E (ApoE)$^{-/-}$ mice (Nakashima et al., 1994, Arterioscler Thromb 14:133-40), suggesting that before cholesterol crystal formation in the vessels, ECs may respond to hyperlipidemia and activate caspase-1 precedent for monocyte recruitment. It has been reported that in response to various proinflammatory stimuli, including lipopolysaccharide, human ECs secrete IL-1β, resulted from the cleavage of pro-IL-1β by activated caspase-1. However, IL-1β secretion from human ECs, detected by ELISA, are 70.6-folds lower than that secreted from human monocytes (Wilson et al., 2007, Br J Pharmacol 151:115-27), suggesting that IL-1β role in ECs as functional consequence of caspase-1 activation may not be as significant as that in monocytes. Thus, additional roles of caspase-1 in ECs need to be further explored. Although proatherogenic functions of caspase-1 (Gage et al., 2012, Can J Cardiol 28:222-9), NLRP3 (Duewell et al., 2010, Nature 464:1357-61), IL-1β (Merhi-Soussi et al., 2005, Cardiovasc Res 66:583-93), and IL-18 (Whitman et al., 2002, Circ Res 30:E34-8) have been reported, important knowledge gaps remain, such as (1) whether caspase-1 sensing system in ECs can sense early hyperlipidemia (noncholesterol crystals lipid stimulus) and (2) whether caspase-1 activation in ECs can promote endothelial activation, monocyte recruitment, and atherogenesis.

It has been reported that caspase-1 can have >70 protein substrates (Shen et al., 2010, Atherosclerosis 201:422-9), the list of which is getting longer. A recent report showed that caspase-1 specifically cleaves sirtuin 1 (Sirt1), a nicotinamide adenine dinucleotide-dependent protein/class III histone deacetylase, in adipose tissue during metabolic stress (Chalkiadaki and Guarente, 2012, Cell Metab 16:180-8). However, the question of whether caspase-1 cleaves Sirt1 in aortic ECs remains unanswered.

Thus, there is a need in the art for compositions and methods for treating hyperlipidemia. The present invention satisfies this unmet need.

SUMMARY OF THE INVENTION

In one aspect, the invention provides a method for treating or preventing a disease or disorder associated with at least one of endothelial activation, inflammation and atherogenesis in a subject in need thereof. In one embodiment, the method comprises administering to the subject an inhibitor of caspase-1-Sirt1-AP-1 pathway.

In one embodiment, the inhibitor is an inhibitor of at least one of the group consisting of caspase-1 activity and caspase-1 expression. In one embodiment, the inhibitor is a non-cleavable Sirt1 peptide inhibitor. In another embodiment, the inhibitor is a human non-cleavable Sirt1 peptide inhibitor.

In one embodiment, the non-cleavable Sirt1 peptide inhibitor comprises a cell membrane permeable protein transduction sequence. In another embodiment, the non-cleavable Sirt1 peptide inhibitor is at least one of Mouse nc-Sirt1: RQIKIWFQNRRMKWKKGYRDNLLLTA-GLLTNGFHSC (SEQ ID NO: 1); or Human nc-Sirt1: RQIKIWFQNRRMKWKKGYRDNLLFGAEIITNGFHSC (SEQ ID NO: 2).

In one embodiment, the inhibitor is selected from the group consisting of a nucleic acid, a siRNA, an antisense nucleic acid, a ribozyme, a peptide, a small molecule, an antagonist, an aptamer, and a peptidomimetic.

In another aspect, the invention provides an inhibitor of caspase-1 activity comprising a non-cleavable Sirt1 peptide inhibitor. In one embodiment, the inhibitor is a human non-cleavable Sirt1 peptide inhibitor. In another embodiment, the non-cleavable Sirt1 peptide inhibitor comprises a cell membrane permeable protein transduction sequence. In yet another embodiment, the non-cleavable Sirt1 peptide inhibitor is at least one of Mouse nc-Sirt1: RQIKIWFQN-RRMKWKKGYRDNLLLTAGLLTNGFHSC (SEQ ID NO: 1); or Human nc-Sirt1: RQIKIWFQNRRMKWKK-GYRDNLLFGAEIITNGFHSC (SEQ ID NO: 2).

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts plasma levels of cholesterol and triglycerides in wild-type mice (WT) and apolipoprotein E gene-deficient mice (ApoE$^{-/-}$) after 0 week (ND), 3 weeks (HF3w), or 6 weeks (HF6w) of high fat (HF) diet (n=5 for each group). FIG. 1B depicts the protein expression of pro-casp-1 and active casp-1 p20 subunit in mouse aorta lysate of WT and ApoE$^{-/-}$ mice after 0, 3, or 6 weeks of HF diet (n=2 for each group). FIG. 1C depicts the correlation of caps-1 activation and plasma lipid levels (of A and B). FIG. 1D depicts Casp-1 mRNA expression in aortas of WT and ApoE$^{-/-}$ after 0, 3, or 6 weeks of HF diet (n=3 for each group). FIG. 1E depicts the protein expression of pro-IL-1β and active IL-1β in mouse aorta lysate of WT and ApoE$^{-/-}$ mice with or without HF diet for 3 weeks. Data are expressed as mean±SE. *P<0.05, changes with the statistical significance.

FIG. 2, comprising FIG. 2A through FIG. 2C, depicts experimental results showing genotyping and characterization of ApoE$^{-/-}$ Casp-1$^{-/-}$ mice. FIG. 2A depicts Polymerase chain reaction (PCR) analysis of ApoE and caspase-1 (casp-1) gene expressions in ApoE$^{-/-}$ mice and ApoE$^{-/-}$/Casp-1$^{-/-}$ mice (left panel). Western blot analysis of pro-casp-1 expression in the aortas of ApoE$^{-/-}$ mice and ApoE$^{-/-}$/Casp-1$^{-/-}$ mice (right panel) (n=2). FIG. 2B depicts General phenotype of Casp-1 deficiency in ApoE$^{-/-}$ mice after 0 or 3 weeks of HF diet: body weight (BW), ratio of heart weight (HW) to BW, and ratio of spleen weight (SW) to BW. FIG. 2C depicts Plasma levels of cholesterol and triglycerides in ApoE$^{-/-}$ mice and ApoE$^{-/-}$/Casp-1$^{-/-}$ mice after 3 weeks of HF diet (HF3w).

FIG. 3, comprising FIG. 3A depicts representative images of atherosclerotic lesion staining of ApoE$^{-/-}$ (n=6) and ApoE$^{-/-}$/Casp-1$^{-/-}$ mice (n=9) in mouse aortic sinus, as the arrows indicated. FIG. 3B depicts atherosclerotic lesion quantification. Data are expressed as mean±SE. *P<0.05, changes with statistical significance. ApoE indicates apolipoprotein E.

FIG. 4, comprising FIG. 4A depicts representative flow cytometric dot plots of live cells (Gate i) in mouse aortic single cell preparations. Monocytes were gated as CD11b$^+$/F4/80$^+$ and CD11b$^+$/F4/80$^-$. Macrophages were gated as CD11b$^-$/F4/80$^+$. FIG. 4B depicts the percentage of macrophages (CD11b$^-$/F4/80$^+$), monocytes (F4/80$^+$/CD11b$^+$ and F4/80$^-$CD11b$^+$) in total aortic cell population in ApoE$^{-/-}$ and ApoE$^{-/-}$/Casp-1$^{-/-}$ mice after 3 weeks of a HF diet (n=10 for each group). FIG. 4C depicts representative flow cytometric dot plots of live cells (Gate i) in mouse peripheral blood. Mononuclear cells (MNC, Gate ii) were first gated according to the forward scatter (FSC) and side scatter (SSC). Monocytes (MC) were identified as CD11b$^+$ mononuclear cells (Gate iii; n=7 for each group). Data are expressed as mean±SE. *P<0.05 and **P<0.01 indicate changes with the statistical significance. ApoE indicates apolipoprotein E.

FIG. 5, comprising FIG. 5A depicts protein expression of intercellular adhesion molecule (ICAM)-1, vascular cell adhesion molecule (VCAM)-1, and E-selectin in aortic tissues from ApoE$^{-/-}$ and ApoE$^{-/-}$/Casp1$^{-/-}$ mice after a high fat (HF) diet for 3 weeks. Representative western blots (top). Quantification of protein expression normalized to the levels of β-actin (bottom). FIG. 5B depicts mRNA expressions of ICAM-1, VCAM-1, and E-selectin in mouse aortic endothelial cells (MAECs) from WT and Casp$^{-/-}$ mice, cultured and treated with oxidized low-density lipoprotein (oxLDL; 100 μg/mL) for 24 hours. FIG. 5C depicts expression level of ICAM-1 in Casp-1 active human aortic endothelial cells (HAECs) after oxLDL treated for 6 hours. FIG. 5D depicts the effect of Casp-1 inhibition on oxLDL-induced monocytic THP-1 cell static adhesion to HAECs. HAECs were cultured and treated with oxLDL (100 μg/mL) for 24 hours. Caspase-1 peptide inhibitor (10 μM, z-YVAD-FMK) and caspase-1 small molecular inhibitor (10 mmol/L) were added 1 hour before the treatment. Data are expressed as mean±SE. *P<0.05. ApoE indicates apolipoprotein E; and WT, wild-type FIG. 6, comprising FIG. 6A depicts a schematic representation of chimeric bone marrow (BM) enhanced green fluorescence protein (EGFP) mice generation. Casp-1$^{+/+}$ BM cells collected from EGFP$^+$ mice were injected into irradiated ApoE$^{-/-}$ mice or ApoE$^{-/-}$/Casp-1$^{-/-}$ mice to determine the effect of caspase-1 deficiency in vascular cells on monocyte migration into the aorta. After a 6-week reconstitution period, the chimeric mice were fed with a high fat (HF) diet for 3 weeks. FIG. 6B depicts the reconstitution rates of EGFP$^+$ nuclear cells in the peripheral blood 6 weeks after BM transplantation. FIG. 6C depicts the monocyte population in mouse aorta after reconstitution with EGFP$^+$ BM. Representative dot plots of CD11b$^-$/EGFP$^+$ cells (Gate ii), CD11b$^+$/EGFP$^+$ monocytes (Gate iii), and CD11b$^+$/EGFP$^-$ (Gate iv) monocyte in mouse aorta. Monocytes in each of the 3 gates were further divided into 3 subsets: Ly-6C$^{high}$, Ly-6C$^{mid}$, and Ly-6C$^{low}$. FIG. 6D depicts the quantification of EGFP$^+$ and CD11b$^-$/EGFP$^+$ cells, and CD11b$^+$/EGFP$^+$ and CD11b$^+$/EGFP$^-$ monocytes within live cells and Ly-6C$^{high}$, Ly-6C$^{middle}$, and Ly-6C$^{low}$ monocytes within indicated gates in ApoE$^{-/-}$ and ApoE$^{-/-}$/Casp-1$^{-/-}$ mouse aortas after BM reconstitution. Number within each graph represents cells in the ApoE$^{-/-}$/Casp-1$^{-/-}$ mouse group as a percentage of the ApoE$^{-/-}$ mouse group (n=6 for each group). FIG. 6E depicts the monocyte population in mouse peripheral blood after reconstitution with EGFP$^+$ BM. Representative dot plots of CD11b$^+$/F4/80$^+$ monocytes in both EGFP$^+$ and EGFP$^-$ peripheral blood cells. Monocytes were further divided into 3 subsets: Ly-6C$^{high}$, Ly-6C$^{mid}$, and Ly-6C$^{low}$. FIG. 6F depicts the quantification of CD11b$^+$/F4/80$^+$ monocytes in both EGFP$^+$ and EGFP$^-$ peripheral blood cells and Ly-6C$^{high}$, Ly-6C$^{middle}$, and Ly-6C$^{low}$ cells in EGFP$^+$ and EGFP$^-$ monocytes. Number within each graph represents cells in the ApoE$^{-/-}$/Casp-1$^{-/-}$ mouse group as a percentage of the ApoE$^{-/-}$ mouse group (n=8 for each group). FIG. 6G depicts the quantification of atherosclerotic lesion area in ApoE$^{-/-}$ and ApoE$^{-/-}$/Casp-1$^{-/-}$ mouse aortas after BM reconstitution. Data are expressed as mean±SE. *P<0.05. ApoE indicates apolipoprotein E; ECs, endothelial cells; FSC, forward scatter; and SSC, side scatter.

FIG. 7, comprising FIG. 7A depicts pyroptotic cell death in HAECs caused by activation of casp-1 induced by oxLDL and its components. HAECs were cultured and treated with low-density lipoprotein (LDL; 100 µg/mL), oxLDL (100 µg/mL), oxLDL-derivatives lysophosphatidic acid (LPA, 100 µM), or lysophosphatidylcholine (LPC, 15 µM) as indicated for 6 hours. Casp-1 activity was determined by a commercial kit, and 7-aminoactinomycin D (7-AAD) fluorescence dye was used to determine the cell membrane integrity. Casp-1$^+$/7-AAD$^+$ cells were gated as pyrototic cells (Q3), casp-1$^+$ single positive cells (Q2) were gated as inflammatory cells, and 7-AAD$^+$ single positive cells (Q4) were gated as necrotic cells. FIG. 7B depicts ROS levels in pyroptotic cells. ROS levels were determined by dihydroethidium (DHE) fluorescence dye staining, and the mean fluorescence intensity (MFI) of DHE$^+$ cell fraction was determined. FIG. 7C depicts attenuation of oxLDL-induced caspase-1 activation in HAECs with ROS inhibitors Allopurinol (xanthine oxidase inhibitor) and Apocynin (NADPH oxidase inhibitor). Allopurinol (1 mmol/L) and Apocynin (100 µM) were added 1 hour before oxLDL treatment. HAECs were then treated with oxLDL (100 µg/mL) for 6 hours and stained for caspase-1 activity. FIG. 7D depicts mRNA upregulation of inflammasome components, including NLRP1 (Nod-like receptor protein 1), NLRP3 (Nod-like receptor 3), PYCARD (or ASC, inflammasome adaptor apoptosis-associated speck-like protein containing a CARD), caspase-1, and IL-1β (interleukin-1β) in HAECs treated with oxLDL. Data are expressed as mean±SE. *P<0.05, changes with statistical significance.

FIG. 8, comprising FIG. 8A depicts Casp-1 deficiency results in Sirt1 accumulation in mouse aorta in ApoE$^{-/-}$/Casp-1$^{-/-}$ mice. ApoE$^{-/-}$ mice and ApoE$^{-/-}$/Casp-1$^{-/-}$ mice were fed with a high fat (HF) diet for 3 weeks. Mouse aortic tissues were collected for uncleaved Sirt1 protein expression analysis by Western blot with the specific antibody (left panel). The quantification of Sirt1 expression in the Western blot was presented after normalized with the expression of β-actin in the same sample (right panel). FIG. 8B depicts oxidized low-density lipoprotein (OxLDL) induces Sirt1 cleavage in human aortic endothelial cells (HAECs). HAECs were cultured and treated with oxLDL (100 µg/mL) for 24 hours. Different doses of non-caspase-1 cleavable sirt1 peptide (NC-SIRT1), superoxide scavengers PEG-SOD and PEG-CAT, and proteasome inhibitor MG-132 were added 1 hour before oxLDL treatment. The protein lysates were collected, and cleaved-Sirt1 expression was determined by Western blot with anti-Sirt1 antibody. The relative changes of Sirt1 expression normalized by β-actin (ratios) were calculated based on the ratios of Sirt1 expression levels in treated samples over that in nontreated samples. FIG. 8C depicts inhibition of caspase-1 attenuates lysophosphatidylcholine (LPC)-induced AP-1 binding to the AP-1 site, revealed by AP-1 electrophoretic gel mobility shift assay (upper panel), whereas inhibition of caspase-1 does not decrease NF-kB binding to the NF-kB site (lower panel). Data are expressed mean±SE. *P<0.05 changes with statistical significance. ApoE indicates apolipoprotein E. Exemplary nc-Sirt1 is set forth in SEQ ID Nos 1 and 2.

FIG. 9, comprising FIG. 9A through FIG. 9C, depicts experimental results showing caspase-1 deficiency attenuates cytokine and chemokine expression in ApoE$^{-/-}$/Casp-1$^{-/-}$ mouse aorta. FIG. 9A depicts the layout of the cytokine and chemokine array (R&D system). FIG. 9B depicts representative array images of the aortic lysates from ApoE$^{-/-}$-mice or ApoE$^{-/-}$/Casp-1$^{-/-}$ mice. Two aortas were pooled together for blotting each array. The signal areas of a caspase-1 substrate, IL-1β, in two arrays were selectively highlighted with red boxes. FIG. 9C depicts quantification of cytokine and chemokine expressions. The variations of the manufacture's designate positive control (PC) spots between each array were used to determine the confidence interval of non-specific variations between samples (n=4 for each group). *, p<0.05 indicates the expression changes with statistical significance

FIG. 11, comprising FIG. 11A through FIG. 11C, depicts experimental results showing caspase-1 promotes secretome of pro-inflammatory cytokines and chemokines in MAECs. FIG. 11A depicts the of the cytokines and chemokine array purchased from R&D systems. FIG. 11B depicts array images of the culture supernatant from WT MAECs or Casp-1$^{-/-}$-MAECs cultured and primed with 50 ng/ml LPS and treated with 200 µg/ml oxLDL for 24 hours followed with ATP (5 mM) spike for 20 min. The array spots of IL-1β were highlighted with the red boxes where the array spots of GM-CSF, CCL3, CCL5 and CXCL12 were indicated with the black ovals, respectively. FIG. 11C depicts quantification of cytokine and chemokine expressions. The variations of the manufacture's designate positive control (PC) spots between each array were used to determine the confidence interval of non-specific variations between samples (n=2 for each group). *, $p<0.05$ change with significance.

FIG. 12, comprising FIG. 12A and FIG. 12B, depicts experimental results showing generation of cell-permeable non-Casp1 cleavable Sirt1 polypeptide. FIG. 12A depicts the NIH-NCBI Blast homology search between mouse SIRT1 (upper) and human SIRT1 (lower). Caspase-1 cleavage site is highlighted in the red box. FIG. 12B depicts the non-cleavable Sirt1 polypeptide was generated with a single amino acid replacement in the sequence from 140-160 position of human SIRT1. Capase-1 cleavage site D150 from human SIRT1 was mutated to A150, rendering the peptide sequence non-casp1 cleavable.

FIG. 14, comprising FIG. 14A depicts experiments where HAECs were treated with different proatherogenic stimuli as follows: oxLDL (100 µM), LPA (30 µM), LPC (30 µM), and $H_2O_2$ (500 µM) for 6 h. Caspase-1(+) cell percentage was measured, and the results showed an increase in caspase-1 activation after proatherogenic lipid treatments. FIG. 14B depicts experiments three different sizes of cell populations after caspase-1 activation were identified using FSC, which is widely used to define the cell size in flow cytometry. The gates were established as small, medium, and large according to the cell size (FSC, y axis) and caspase-1 activation (x axis) to analyze the differential caspase-1 activation percentage according to the cell size. Analysis of three gates showed an increase in caspase-1 activation percentage in larger HAECs. FIG. 14C depicts the quantitation data of caspase-1 activation. *, $p<0.05$.

FIG. 16, comprising FIG. 16A depicts VEGFR-2 depletion increases the expressions of caspase-1 and inflammasome adaptor protein ASC. The microarray data-mining analyses were performed using the National Institutes of Health NCBI-Geo-profile database. The microarray dataset IDs were indicated. FIG. 16B depicts experiments where HAECs were pretreated with VEGFR-2 inhibitor (SU1498) and then treated with LPC (30 µM) for 6 h after overnight starvation with serum-free medium. The bar graph shows the quantitation data of caspase-1 activation, which demonstrates an increase in caspase-1 activation after the inhibition of VEGFR-2 in LPC-treated HAECs. *, $p<0.05$.

FIG. 17, comprising FIG. 17A through FIG. 17D, depicts experimental results showing inhibition of caspase-1 activation and activation of Sirt-1 increase VEGFR-2 expression. FIG. 17A depicts experiments showing caspase-1 depletion increases VEGFR-2 expression. A microarray data-mining analysis was performed by analyzing the indicated microarray dataset deposited in the National Institutes of Health NCBI-Geo-profile database. The gene expression value was determined based on the relative threshold cycle on the database. Caspase-1 expression was used as a control to show that caspase-1 expression was absent in the caspase-1 gene depletion samples. In addition, depletion of caspase-1 slightly increases the expressions of the caspase-1-cleaving substrates cytokines IL-1β and IL-18. As the microarray data quality controls, caspase-1 depletion did not significantly change the expressions of three housekeeping genes, Gadph, Nono, and Aldoa. FIG. 17B depicts caspase-1 inhibition and Sirt-1 activation increase the expression of VEGFR-2 after LPC treatment in HAECs. HAECs pretreated with the caspase-1 inhibitor (10 µM) and Sirt-1 activator (10 µM) and then treated with LPC (30 µM) for 6 h have an increased expression of VEGFR-2. FIG. 17C depicts three cell size gates were established, small, medium, and large according to FSC (y axis); and VEGFR-2 expression (x axis) was measured in those gated cells to analyze differential VEGFR-2 expressions according to the cell size after treatments with LPC (30 µM), caspase-1 inhibitor (10 µm), and Sirt-1 activator (10 µm) for 6 h. The analysis shows increases in VEGFR-2 expression as the cell sizes became larger. FIG. 17D depicts bar graphs showing the quantitation data of VEGFR-2 expressions. *, $p<0.05$.

FIG. 18, comprising FIG. 18A depicts experiments where HAECs were treated with LPC (30 µm) and caspase-1 inhibitor (10 µm) for 6 h. After the treatment, the cells were incubated in the Matrigel for 16 h for the analysis of tube formation. FIG. 18B depicts bar graph showing the increases of total master segment lengths after the inhibition of caspase-1 in LPC-treated HAECs.*, $p<0.05$.

FIG. 19, comprising FIG. 19A depicts experiments where hind limb ischemia model was performed in WT and caspase-1 KO mice. The blood flow was recorded with the LDSII Doppler at different time points. The data show that the caspase-1 KO mice have a trend of increased blood flow after hind limb ischemia. FIG. 19B depicts linear graph shows the quantification of the ischemia/normal leg perfusion ratio. FIG. 19C depicts that an absolute value (y−x) was used to create a confidence interval.

FIG. 21, comprising FIG. 21A depicts the experiment design. Wild-type (WT) mice and ApoE$^{-/-}$ mice were fed with either chow diet or high fat (HF) for 12 weeks (w) before their bone marrows (BM) were collected for fluorescence activated cell sorter (FACS) analysis. FIG. 21B depicts experiments where after gating mononuclear cells from the BM, Sca-1$^+$ stem cells were gated from the mononuclear cells. FIG. 21C depicts experiments where among Sca-1$^+$ stem cell populations in the BM, caspase-1 activity was measured. Gating of caspase-1 positive (Casp1$^+$) cells in Sca-1$^+$ population of mouse BM was shown in the left. Quantification was shown in the right.

FIG. 23, comprising FIG. 23A depicts volcano plots of apoliprotein E deficient (ApoE$^{-/-}$) mice versus Wild type (WT) mice aorta DNA expression comparisons (blue), with the overlay of Caspase-1 (Casp1)$^{-/-}$/ApoE$^{-/-}$ versus ApoE$^{-/-}$ comparisons (red) are depicted by estimated fold change (FC)(log 2 FC, x-axis) and statistical significance (−log 10 P value, y-axis). FIG. 23B depicts cooperation between Caspase1 and hyperlipidemia is shown by Log 2 FC/Log 2 FC plot comparing gene expression value for Caspase1/ApoE DKO versus ApoE KO (x-axis), and parallel ApoE KO versus WT (y-axis). FIG. 23C depicts a Venn diagram showing the profile of two gene expression comparisons. Among 23,470 mapped genes, a total of 6,745 genes were significantly changed induced by hyperlipidemia and 2,541 genes were significantly changed caused by Caspase1 deletion. Among the changed genes, there are 969 genes changed in condition of hyperlipidemia and reversed by Caspase1 deletion. FIG. 23D depicts heatmaps representing the z-score of the expression level of top 50 reversed genes (hyperlipidemia increased or decreased genes which are down-regulated or up-regulated by deletion of Caspase1). FIG. 23E depicts core analysis with Ingenuity pathway analysis (IPA) shows that the major molecular and cellar functional pathways are cellular growth and proliferation and cell death. FIG. 23F depicts the network showing the connection of the caspase-1 reserved genes associated with apoptosis and necrosis of endothelial cells.

FIG. 25, comprising FIG. 25A through FIG. 25E, depicts experimental results showing caspase-1$^{-/-}$ Sca-1$^+$ progenitor cell therapy improves cardiac function after MI. FIG. 25A depicts the myocardiac infarction (MI) and cell therapy model. Schematic representation of experimental plan including high fat diet feeding, cardiac function monitoring with echocardiography, cell therapy with purified Sca-1+ bone marrow cells followed by immunohistochemistry and flow cytometry analyses. FIG. 25B depicts the CellVueR NIR780 fluorescence-labeled cells were traced to heart after intravenous injection. The CellVueR NIR780 fluorescence-labeled purified Sca-1+ bone marrow cells (2×10$^6$ cells/mouse) were traced to mouse heart after cell therapy (n=4 for tracer group, n=2 for non-cell tracer group). CT: no cell therapy control; cell: cell therapy FIG. 25C depicts M-mode Echocardiography. Representative M-mode echocardiographs of control mice and myocardiac infarcted mice. FIG. 25D depicts cardiac functions measured with echocardiography. The cardiac function measurements of control mice, myocardial infarction (MI) mice, mice receiving wild-type (WT) Sca-1+BM cells and mice receiving caspase-1 (Casp1)$^{-/-}$ Sca-1$^+$ BM cells. The numbers shown indicate the numbers of mice in the group. FIG. 25 E depicts heart, Lung, Liver weight/body weight. The ratios of heart weight/body weight, lung weight/body weight and liver weight/body weight of mice receiving cell therapy and control mice.

FIG. 26, comprising FIG. 26A depicts capillary density detected with IB4 staining for endothelial cells in neovasculature. Histochemical analysis of heart cross sections showed that cell therapy with Sca-1+ BM cells from casp-1$^{-/-}$ mice increases IB4+ capillary density (endothelial cells) in comparison to the cell therapy with Sca-1$^+$ BM cells from wild type (WT) mice. FIG. 26B depicts TUNEL Assay for detecting cell death in myocardial infarcted heart. Histochemical analysis of heart cross sections showed that the cell therapy with Sca-1$^+$ BM cells from casp-1$^{-/-}$ mice decreases TUNEL$^+$ cardiomyocytes in comparison to the cell therapy with Sca-1$^+$ BM cells from WT mice.

FIG. 30, comprising FIG. 30A depicts the experimental design for the creation of CKD model and NH model in WT and caspase-1−/− mice. The model was created by performing right kidney ablation at 9 weeks of age on both WT and caspase-1−/− mice. After one week, left nephrectomy was performed to create a CKD state. To verify the CKD state in mice, the blood urea nitrogen (BUN) levels were measured. At week 4, after the CKD creation, a left common carotid artery (LCCA) ligation was performed in order to induce neointimal hyperplasia (NH). Three weeks after the LCCA ligation, the artery was perfused and fixed with formalin at 100 mm HG for 15 minutes and harvested for cross-section immunohistochemistry analysis. The Verhoeff elastic-van Gieson (VVG) staining was used on LCCA cross-sections to determine the development of neointimal hyperplasia. FIG. 30B depicts the animal weight and BUN levels measured in both mouse groups. There were no statistically significant differences in body weight and BUN levels between both groups.

FIG. 31, comprising FIG. 31A depicts representative cross-sections of left common carotid arteries stained with VVG. At 9 weeks of age, the mice underwent CKD creation. 3 weeks later the mice underwent left common carotid artery (LCCA) ligation. At 15 weeks of age, representative cross-sections of the left common carotid arteries from WT sham, WT CKD, and caspase-1−/− (Casp1−/−) CKD mice were stained with the VVG. The results demonstrate that the carotid artery in caspase-1−/− CKD mice has decreased neointimal hyperplasia development. FIG. 31E depicts results showing the media volume in WT CKD mice is not significantly different from that of caspase-1−/− CKD mice. *P value<0.05.

FIG. 33, comprising FIG. 33A depicts microarray data analysis showing that the expression of Integrin alpha V RNA transcripts in wild-type tissue is significantly higher than that in caspase-1−/− mice after feeding with high fat diet for 16 weeks. FIG. 33B depicts the mean±2SD of the ratio of three housekeeping genes was used as the 95% confidence interval.

DETAILED DESCRIPTION

Figures 1A, 1B, 1C, 1D, 1E:
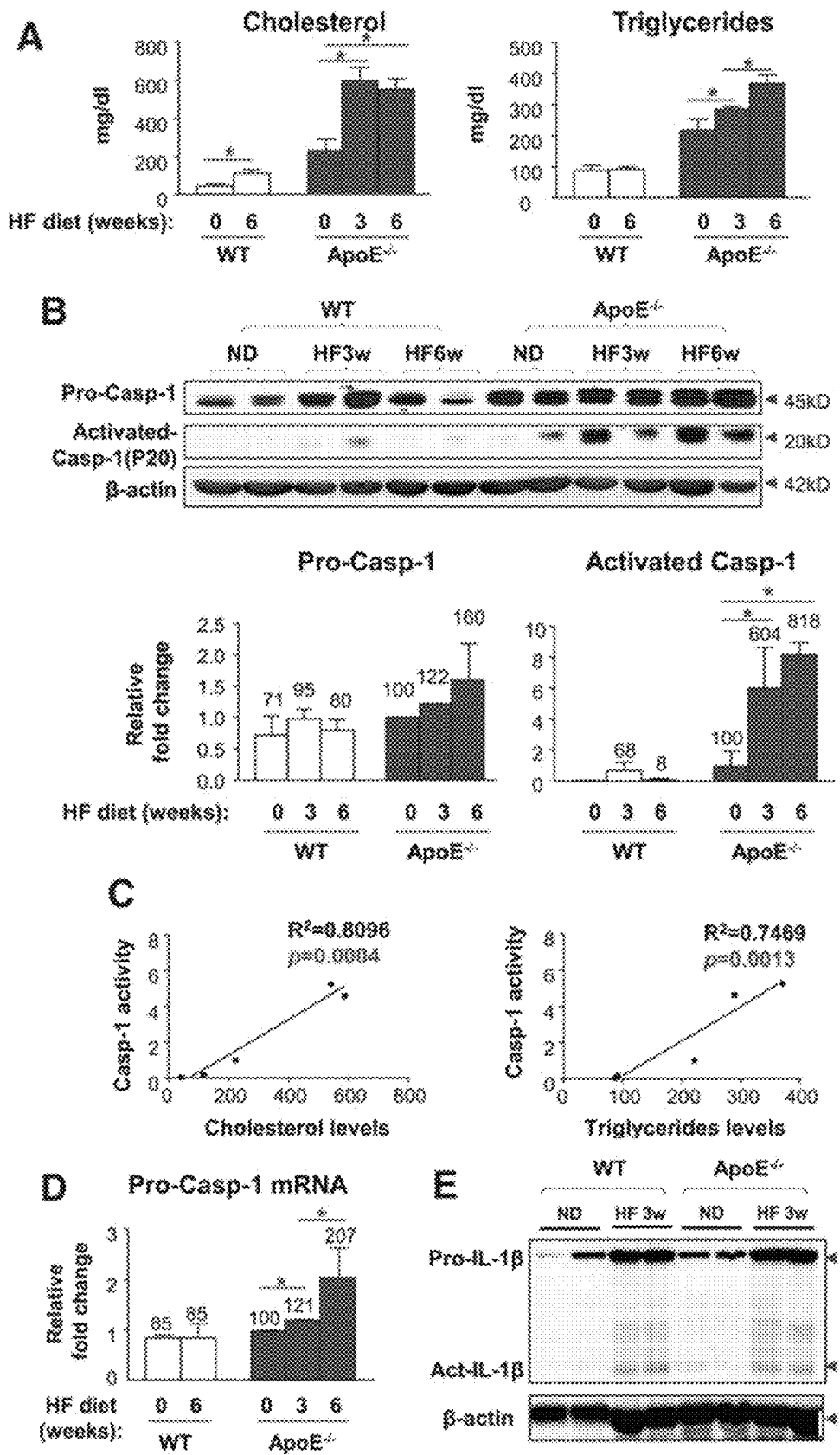
FIG. 1A through FIG. 1E, depicts experimental results showing early hyperlipidemia induces caspase-1 (casp-1) expression and activation in mouse aorta.

The present invention relates generally to compositions and methods for treating cardiovascular disease, inflammation, or atherosclerosis. The invention is useful, for example, in decreasing the expression of proinflammatory cytokines, atherosclerotic lesions in the early stage of atherogenesis, monocyte recruitment in the aorta, endothelial activation. The invention is also useful in increasing the anti-inflammatory protein sirt1. In certain embodiments, the invention provides compositions and methods for reducing expression of cytokines, chemokines and adhesion molecules which are expressed via an Sirt1-AP-1-mediated pathway.

In one embodiment, the present invention provides a composition for treating cardiovascular disease, inflammation, or atherosclerosis in a subject. In one embodiment, the composition comprises an inhibitor of caspase-1 expression, activity or a combination thereof. In one embodiment, the inhibitor inhibits the caspase-1 dependent cleavage of Sirt1.

In another embodiment, the present invention provides a method of treating a disease or disorder related to cardiovascular disease, inflammation, or atherosclerosis in a subject. In one embodiment, the method comprises administering to the subject an effective amount of an inhibitor of caspase-1 expression, activity or a combination thereof.

The present invention relates to a method for treating or preventing a disease or disorder associated with endothelial activation, inflammation or atherogenesis, including but not limited to cardiovascular diseases and inflammatory disorders. The method comprises administering to a subject an inhibitor of caspase-1-Sirt1-AP-1 pathway. In one aspect, the method comprises administering to a subject a composition comprising a non-cleavable Sirt1 peptide inhibitor, which inhibits the activity of caspase-1.

In one aspect, the present invention relates to compositions and pharmaceutical compositions for inhibiting the activity of caspase-1. In one embodiment, the composition comprises a non-cleavable Sirt1 peptide inhibitor.

In one aspect, the invention provides methods of compositions and methods for treating cardiovascular disease, inflammation, or atherosclerosis. In one embodiment, the composition comprises an inhibitor of caspase-1 activation or expression. In one embodiment, the inhibitor of caspase-1 activation or expression increases VEGFR-2 expression. In another embodiment, the inhibitor of caspase-1 increases pyroptosis of large aortic endothelial cells. In another embodiment, the inhibitor of caspase-1 increases tube formation of aortic endothelial cells. In another embodiment, the inhibitor of caspase-1 increases ischemia and blood perfusion ratio. In yet another embodiment, the inhibitor of caspase-1 increases angiogensis.

In one embodiment, the method of the invention comprises, administering an inhibitor of caspase-1 activity or expression to a bone marrow-derived stem cell antigen-1 positive stem cell or progenitor cell; and transplanting the cell in a subject. In one embodiment, the method the subject has experienced a myocardial infarction. In one embodiment, the transplantation improves cardiac function. In one embodiment, the transplantation decreases cardiomyocyte cell death.

In one embodiment, the inflammation is a symptom of chronic kidney disease. In another embodiment, the inhibition of caspase-1 decreases chronic kidney disease-induced neointima hyperplasia.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity or frequency of at least one sign or symptom of the disease or disorder experienced by a patient is reduced.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

The term "expression" as used herein is defined as the transcription and/or translation of a particular nucleotide sequence driven by its promoter.

As used herein, a "peptidomimetic" is a compound containing non-peptidic structural elements that is capable of mimicking the biological action of a parent peptide. A peptidomimetic may or may not comprise peptide bonds.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods. A host cell that comprises a recombinant polynucleotide is referred to as a "recombinant host cell." A gene which is expressed in a recombinant host cell wherein the gene comprises a recombinant polynucleotide, produces a "recombinant polypeptide."

As used herein, a "recombinant cell" is a host cell that comprises a recombinant polynucleotide.

By the term "specifically binds," as used herein, is meant a molecule, such as an antibody, which recognizes and binds to another molecule or feature, but does not substantially recognize or bind other molecules or features in a sample.

As used herein, the term "transdominant negative mutant gene" refers to a gene encoding a polypeptide or protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "subject" or "patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for treating or preventing a disease or disorder associated with endothelial activation, inflammation or atherogenesis, including but not limited to cardiovascular diseases and inflammatory disorders.

In one embodiment, the composition comprises an inhibitor of the expression of caspase-1. For example, in one embodiment, the composition comprises an isolated nucleic acid (e.g., siRNA, ribozyme, antisense RNA, etc.) that reduces the nucleic acid or protein expression level in a cell of caspase-1.

In one embodiment, the composition comprises an inhibitor of the activity of caspase-1. For example, in one embodiment, the composition comprises a nucleic acid, peptide, antibody, small molecule, antagonist, aptamer, or peptidomimetic that reduces the activity of caspase-1.

Composition

In one embodiment, the composition of the invention comprises an inhibitor of caspase-1. An inhibitor of caspase-1 is any compound, molecule, or agent that reduces, inhibits, or prevents the function of caspase-1. In certain embodiments, the inhibitor inhibits the transcription of DNA, inhibits the translation of RNA, or inhibits the protein itself. In one embodiment, an inhibitor of caspase-1 comprises a nucleic acid, a peptide, an antibody, a small molecule, a siRNA, a ribozyme, an antisense nucleic acid, an antagonist, an aptamer, a peptidomimetic, or any combination thereof.

Small Molecule Inhibitors

In various embodiments, the inhibitor is a small molecule. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analog or derivative of an inhibitor described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to reduce skin pigmentation.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acid Inhibitors

In other related aspects, the invention includes an isolated nucleic acid. In one embodiment, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In another aspect of the invention, caspase-1, can be inhibited by way of inactivating and/or sequestering caspase-1. As such, inhibiting the activity of caspase-1 can be accomplished by using a transdominant negative mutant.

In one embodiment, the composition comprises a nucleic acid molecule encoding a peptide inhibitor of caspase-1. In one embodiment, the nucleic acid molecule encodes a non-cleavable Sirt1 peptide, which inhibits caspase-1 activity. In one embodiment, the nucleic acid molecule comprises a nucleic acid sequence encoding a peptide inhibitor comprising an amino acid sequence of SEQ ID NO: 1. In one embodiment, the nucleic acid molecule comprises a nucleic acid sequence encoding a peptide inhibitor comprising an amino acid sequence of SEQ ID NO: 2.

In certain embodiments, the peptide inhibitor is encoded by a nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 1. In certain embodiments, the peptide inhibitor is encoded by a nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

In one embodiment, siRNA is used to decrease the level of caspase-1, or caspase-1 protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of caspase-1 using RNAi technology.

In another aspect, the invention includes a vector comprising an siRNA or antisense polynucleotide. Preferably, the siRNA or antisense polynucleotide is capable of inhibiting the expression of a target polypeptide. The incorporation of a desired polynucleotide into a vector and the choice of vectors is well-known in the art as described in, for example, Sambrook et al. (2012), and in Ausubel et al. (1997), and elsewhere herein.

In certain embodiments, the expression vectors described herein encode a short hairpin RNA (shRNA) inhibitor. shRNA inhibitors are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

In one embodiment of the invention, an antisense nucleic acid sequence which is expressed by a plasmid vector is used to inhibit caspase-1, or caspase-1 protein expression. The antisense expressing vector is used to transfect a mammalian cell or the mammal itself, thereby causing reduced endogenous expression of caspase-1.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used to inhibit caspase-1 expression. Ribozymes useful for inhibiting the expression of a target molecule may be designed by incorporating target sequences into the basic ribozyme structure which are complementary, for example, to the mRNA sequence encoding caspase-1. Ribozymes targeting caspase-1, may be synthesized using commercially available reagents (Applied Biosystems, Inc., Foster City, Calif.) or they may be genetically expressed from DNA encoding them.

In one embodiment, the nucleic acid inhibitor of the invention is an antagonist of caspase-1. For example, in certain embodiments, the isolated nucleic acid specifically binds to caspase-1, or a target of caspase-1, to inhibit the functional activity of caspase-1.

Peptide Inhibitors

In other related aspects, the invention includes an isolated peptide inhibitor that inhibits caspase-1. For example, in one embodiment, the peptide inhibitor of the invention inhibits caspase-1 directly by binding to caspase-1 thereby preventing the normal functional activity of caspase-1. In another embodiment, the peptide inhibitor of the invention inhibits caspase-1 by competing with endogenous caspase-1. In yet another embodiment, the peptide inhibitor of the invention inhibits the activity of caspase-1 by acting as a transdominant negative mutant.

In one embodiment, the peptide inhibitor of the invention comprises a non-cleavable Sirt1 peptide. For example, in one embodiment, the peptide inhibitor comprises the amino acid sequence of SEQ ID NO: 1. In one embodiment, the peptide inhibitor comprises the amino acid sequence of SEQ ID NO: 2.

In one embodiment, the peptide inhibitor comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 1. In one embodiment, the peptide inhibitor comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

A peptide inhibitor of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide inhibitor.

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

(a) Tags

In one embodiment, the composition comprises a peptidomimetic inhibitor of at least one of caspase-1. Peptidomimetics are compounds based on, or derived from, peptides and proteins. The peptidomimetics of the present invention typically can be obtained by structural modification of known caspase-1 sequences or sequences that interact with caspase-1, using unnatural amino acids, conformational restraints, isosteric replacement, and the like. The peptidomimetics constitute the continuum of structural space between peptides and non-peptide synthetic structures.

Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988, p123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124:141), and methyleneamino-modified (Roark et al. in Peptides: Chemistry and Biology, G. R. Marshall ed., ESCOM Publisher: Leiden, Netherlands, 1988, p 134). Also, see generally, Session III: Analytic and synthetic methods, in Peptides: Chemistry and Biology, G. R. Marshall ed., ESCOM Publisher: Leiden, Netherlands, 1988)

In addition to a variety of side chain replacements which can be carried out to generate peptidomimetics, the present invention contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

A peptide or peptidomimetic inhibitor of the invention may be synthesized by conventional techniques. For example, the peptide or peptidomimetic inhibitor may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J.

Meienhofer, Eds., The Peptides: Analysis, Synthesis, Biology, suprs, Vol 1, for classical solution synthesis.)

Antibody Inhibitors

The invention also contemplates an inhibitor of caspase-1 comprising an antibody, or antibody fragment, specific for caspase-1. That is, the antibody can inhibit caspase-1 to provide a beneficial effect.

The antibodies may be intact monoclonal or polyclonal antibodies, and immunologically active fragments (e.g., a Fab or (Fab)$_2$ fragment), an antibody heavy chain, an antibody light chain, humanized antibodies, a genetically engineered single chain Fv molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magnetic-actived cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

The invention also includes functional equivalents of the antibodies described herein. Functional equivalents have binding characteristics comparable to those of the antibodies, and include, for example, hybridized and single chain antibodies, as well as fragments thereof.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')$_2$ fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers (H$_2$L$_2$) formed of two dimers associated through at least one disulfide bridge.

Cells

In certain embodiments, the composition comprises a cell genetically modified to express one or more isolated nucleic acids and/or proteins described herein. For example, the cell may be transfected or transformed with one or more vectors comprising a nucleic acid encoding a caspase-1 inhibitor. The cell can be the subject's cells or they can be haplotype matched. In specific embodiments, the cell is a stem cell. In some embodiments the stem cell is a bone marrow-derived Sca1$^+$ stem cell.

Scaffolds

The present invention provides a scaffold or substrate composition comprising an inhibitor of the invention, a peptide of the invention, a cell of the invention or any combination thereof.

For example in one embodiment, the scaffold or substrate composition comprising an inhibitor of caspase-1, a nucleic acid molecule encoding a caspase-1 inhibitor, a cell comprising a caspase-1 inhibitor, a cell comprising a nucleic acid molecule encoding a caspase-1 inhibitor, or a combination thereof.

For example, in one embodiment, an inhibitor of caspase-1, a nucleic acid molecule encoding a caspase-1 inhibitor, a cell comprising a caspase-1 inhibitor, a cell comprising a nucleic acid molecule encoding a caspase-1 inhibitor, or a combination thereof is within a scaffold.

In one embodiment, an inhibitor of caspase-1, a nucleic acid molecule encoding a caspase-1 inhibitor, a cell comprising a caspase-1 inhibitor, a cell comprising a nucleic acid molecule encoding a caspase-1 inhibitor, or a combination thereof is applied to the surface of a scaffold.

The scaffold of the invention may be of any type known in the art. Non-limiting examples of such a scaffold includes a, hydrogel, electrospun scaffold, foam, mesh, sheet, patch, and sponge.

Treatment Methods

The present invention provides methods of treating or preventing a disease or disorder associated with endothelial activation, inflammation or atherogenesis. In one embodiment, the method comprises administering an effective amount of a composition of the invention.

Administration of a caspase-1 inhibitor comprising for example one or more peptides, a small molecule, an antisense nucleic acid, a soluble receptor, an antibody, a cell, or a scaffold in a method of treatment can be achieved in a number of different ways, using methods known in the art.

It will be appreciated that an inhibitor of the invention may be administered to a subject either alone, or in conjunction with another therapeutic agent.

In one embodiment, an exogenous caspase inhibitor of the invention is administered to a subject. The exogenous peptide may also be a hybrid or fusion protein to facilitate, for instance, delivery to target cells or efficacy. In one embodiment, a hybrid protein may comprise a tissue-specific targeting sequence.

The therapeutic and prophylactic methods of the invention thus encompass the use of pharmaceutical compositions comprising a caspase inhibitory peptide, fusion protein, small molecule, soluble receptor, or antibody of the invention and/or an isolated nucleic acid encoding a caspase inhibitory peptide, fusion protein small molecule, soluble receptor, or antibody of the invention to practice the methods of the invention. The pharmaceutical compositions useful for practicing the invention may be administered to deliver a dose of from ng/kg/day and 100 mg/kg/day. In one embodiment, the invention envisions administration of a dose which results in a concentration of the compound of the present invention from 1 μM and 10 μM in a mammal.

Typically, dosages which may be administered in a method of the invention to a mammal, preferably a human, range in amount from 0.5 μg to about 50 mg per kilogram of body weight of the mammal. While the precise dosage administered will vary depending upon any number of factors, including but not limited to, the type of mammal and type of disease state being treated, the age of the mammal and the route of administration. Preferably, the dosage of the compound will vary from about 1 μg to about 10 mg per kilogram of body weight of the mammal. More preferably, the dosage will vary from about 3 μg to about 1 mg per kilogram of body weight of the mammal.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

The administration of the inhibitor of the invention to the subject may be accomplished using gene therapy. Gene therapy, which is based on inserting a therapeutic gene into a cell by means of an ex vivo or an in vivo technique. Suitable vectors and methods have been described for genetic therapy in vitro or in vivo, and are known as expert on the matter; see, for example, Giordano, Nature Medicine 2 (1996), 534-539; Schaper, Circ. Res 79 (1996), 911-919; Anderson, Science 256 (1992), 808-813; Isner, Lancet 348 (1996), 370-374; Muhlhauser, Circ. Res 77 (1995), 1077-1086; Wang, Nature Medicine 2 (1996), 714-716; WO94/29469; WO97/00957 or Schaper, Current Opinion in Biotechnology 7 (1996), 635-640 and the references quoted therein. The polynucleotide codifying the polypeptide of the invention can be designed for direct insertion or by insertion through liposomes or viral vectors (for example, adenoviral or retroviral vectors) in the cell. Preferably the cell is a cell of the germinal line, an embryonic cell or egg cell or derived from the same, more preferably the cell is a core cell. Suitable gene distribution systems that can be used according to the invention may include liposomes, distribution systems mediated by receptor, naked DNA and viral vectors such as the herpes virus, the retrovirus, the adenovirus and adeno-associated viruses, among others. The distribution of nucleic acids to a specific site in the body for genetic therapy can also be achieved by using a biolistic distribution system, such as that described by Williams (Proc. Natl. Acad. Sci. USA, 88 (1991), 2726-2729). The standard methods for transfecting cells with recombining DNA are well known by an expert on the subject of molecular biology, see, for example, WO94/29469; see also supra. Genetic therapy can be carried out by directly administering the recombining DNA molecule or the vector of the invention to a patient or transfecting the cells with the polynucleotide or the vector of the invention ex vivo and administering the transfected cells to the patient.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents useful in the treatment of fibrosis include anti-inflammatories, including corticosteroids, and immunosuppressants.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrastemal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Early Hyperlipidemia Promotes Endothelial Activation Via a Caspase-1-Sirtuin 1 Pathway This study examined a novel hypothesis that caspase-1 in ECs can sense hyperlipidemia in mice fed a HF diet for 3 weeks and that caspase-1 activation in ECs, potentially via the caspase-1-Sirt1 pathway, can promote endothelial activation, monocyte recruitment, and atherogenesis. Double gene knockout (KO) mice were generated that are deficient of caspase-1 and ApoE (ApoE$^{-/-}$/caspase-1$^{-/-}$) by crossing caspase-1$^{-/-}$ mice into ApoE$^{-/-}$ mouse background. Our results demonstrate that caspase-1 activation significantly contributes to endothelial activation, monocyte recruitment, and atherogenesis via the caspase-1-Sirt1-activator protein-1 (AP-1) pathway. Therefore, these results indicate a role for caspase-1 activation in sensing hyperlipidemia as a DAMP and promoting endothelial activation.

The results demonstrate for the first time that early hyperlipidemia promotes EC activation before monocyte recruitment via a caspase-1-sirtuin 1-activator protein-1 pathway, which provides an important insight into the development of novel therapeutics for blocking caspase-1 activation as early intervention of metabolic cardiovascular diseases and inflammations.

The material and methods employed in these experiments are now described.

Reagents

Dulbecco's modified Eagle's medium, M199, penicillin, streptomycin, L-glutamate, and heparin were purchased from Invitrogen (Carlsbad, Calif.). Dihydroethidium (DHE) was purchased from Molecular Probes (Eugene, Oreg.). Caspase-1 peptide inhibitor (Ac-YVAD-CHO) was from ALEXIS Biochemicals (San Diego, Calif.), and caspase-1 small molecular inhibitor was generously provided by Dr. Craig Thomas of the NIH Chemical Genomics Center. Antibodies against β-actin were purchased from Sigma-Aldrich (St. Louis, Mo.). Caspase-1 antibody (Cat #14-9832-80) was purchased from eBioscience (San Diego, Calif.). Low-density lipoprotein (LDL), oxidized LDL (ox-LDL), and acetylated LDL labeled with 1,1'-dioctadecyl-3, 3,3',3'-tetramethyl-indocarbocyanine perchlorate (Dil-Ac-LDL) were purchased from Biomedical Technologies (Stoughton, Mass.). Lysophosphatidylcholine (LysoPC, 1-hexadecanoyl-sn-glycerol-3-phosphorylcholine) and lysophosphatidic acid (LysoPA; mono-acylsn-glycero-3-phosphate) were purchased from Avanti Polar Lipids (Alabaster, Ala.). Antibodies to intercellular adhesion molecule-1 (ICAM-1) (sc-18853), vascular cell adhesion molecule-1 (VCAM-1) (sc-8304), and E-selectin [CD62 antigen-like family member E (CD62E)] (sc-14011) were purchased from Santa Cruz (Santa Cruz, Calif.). All other reagents were purchased from Sigma-Aldrich, unless indicated otherwise.

Mice and Diets

C57BL/6J mice, chicken β-actin promoter possessing cytomegalovirus (CMV) enhancer driven enhanced green fluorescence protein (EGFP)-transgenic mice, and apolipoprotein E gene deficient (ApoE$^{-/-}$) mice in a C57BL/6J background were obtained from the Jackson Laboratory (Bar Harbor, Me.). Caspase-1$^{-/-}$ (Casp-1$^{-/-}$) mice in a C57BL/6J background were generously provided by Dr. Richard Flavell's laboratory (Yale University School of Medicine, CT). ApoE$^{-/-}$ mice and Casp-1$^{-/-}$ mice were crossed to establish ApoE$^{-/-}$/Casp-1$^{-/-}$ mice. All mice were kept under specific pathogen-free conditions in a temperature controlled environment. Age-matched male mice were used for all experiments. At the age of 8 weeks, mice were maintained on a normal chow diet (5% fat, Labdiet 5001) or fed a diet supplemented with 0.2% (w/w) cholesterol and 21.2% (w/w) fat (HF diet) (TD. 88137, Harlan Teklad, WI) for designated periods. For tissue collection, mouse heart, aorta, and spleen were collected under a dissecting microscope and weighed from euthanized mice. All procedures in animals were performed in accordance with the approvals of Temple University Institutional Animal Care and Use Committee (IACUC).

Genotyping

Murine genomic deoxyribonucleic acid (DNA) was collected using the following method. Briefly, a small piece of mouse tail tissue was collected from the mouse and digested with 500 μl lysate buffer [100 mM Tris-HCl (pH 8.5), 5 mM EDTA, 0.2% SDS, 200 mM NaCl] supplemented with 200 mg/mL proteinase K (EMD Millipore, Billerica, Mass.) overnight at 55° C. with shaking in a Thermomixer. The DNA was separated from the wrapping protein by occasional gentle taps of the digestion tube during the digestion process. The tissue debris was separated by centrifugation. The digestion supernatant (450 μL) was transferred into a new tube and mixed with 700 μL of isopropanol. The DNA was then precipitated and transferred into a new tube containing 200 μL of H$_2$O, and dissolved by overnight incubation at 55° C. The genomic DNA was used for polymerase chain reaction (PCR) and the PCR product was separated on an agarose gel. Specific primers were used to determine the genotype of the mice. For ApoE, primer 180 (5'-GCCTAGC-CGAGGGAGAGCCG-3' (SEQ ID NO: 3)), 181 (5'-TGT-GACTTGGGAGCTCTGCAGC-3'(SEQ ID NO: 4)), and 182 (5'-GCCGCCCCGACTGCATCT-3' (SEQ ID NO: 5)) were used. The PCR cycle was 94° C. for 30 seconds (sec), 68° C. for 40 sec, 72° C. for 1 minute (min), and repeated for 35 cycles. The DNA fragment for ApoE$^{-/-}$ mice was 245 base pairs (bp), and the DNA fragment for WT mice was 150 bp in length. For detection of caspase-1 KO mice, primer ICE 3(5'-ATGGCACACCACAGATATCGG-3'(SEQ ID NO:6)), ICEKO (5'-TGCTAAAGCGCATGCTCCA-GACTG-3'(SEQ ID NO: 7)), and ICES (5'-GAGA-CATATAAGG GAGAAGGG-3' (SEQ ID NO: 8)) were used. The PCR cycle was 94° C. for 30 sec, 60° C. for 1 min, 72° C. for 1 min, and repeat for 40 cycles. The DNA fragment for Casp-1$^{-/-}$ mice was 300 bp and the DNA fragment for WT mice was 500 bp in length.

Lipid and Lipoprotein Analysis

Blood was collected in 5% EDTA coated tubes from the inferior vena cava of anesthetized animals. Plasma was separated by low speed centrifugation for 20 min at 4° C. Plasma concentrations of total cholesterol (TC) and triglyceride (TG) in each sample were measured at the National Mouse Metabolic Phenotyping Center in Vanderbilt University (Nashville, Tenn.).

Aortic Sinus Cross-Section and Atherosclerotic Lesion Characterization

Mouse hearts were harvested, weighed, and fixed overnight with 4% paraformaldehyde (PFA). Fixed tissues were then impregnated with 20% (v/v) sucrose in PBS [1 mM Na$_2$HPO$_4$, 137 mM NaCl, 1.5 mM KH$_2$PO$_4$, 2.7 mM KCl at pH 7.4] embedded with optimal cutting temperature compound (OCT) (Tissue Tek, Sakura Finetek, DK), and quickly frozen on dry ice. Serial cross sections of the aortic root were collected on slides; 10 μm cryostat sections were taken from the level where the 3 aortic valves first appeared to the level where the aortic valves disappeared. A total of 80 sections were collected on 10 slides. Sections of the aortic sinus were stained with Oil Red O and alum hematoxylin. Briefly, fixed sections were rinsed with 60% isopropanol and stained with freshly prepared Oil Red O working solution (0.3% Oil Red O in 60% isopropanol) for 18 min. Followed with another rinse with 60% isopropanol, the sections were then stained with alum hematoxylin and washed with distilled water. The stained sections were then mounted in aqueous mounting medium and stored in room temperature until imaging. Images were captured with a Zeiss Axioscope microscope (Carl Zeiss Inc., Thornwood, N.Y.). Atherosclerotic lesion area was defined as the red area staining with Oil red O and measured with ImageJ (NIH, Bethesda, Md.). The percentage of lesion area was calculated by dividing lesion area by the total sinus area, and the average value of eight sections on each slide was presented.

Mouse Peripheral Blood Cell Isolation

Peripheral blood was drawn from the inferior vena cava or by tail bleeding from anesthetized animals. Red blood cells were lysed with Ammonium-Chloride-Potassium (ACK) lysing buffer [0.15M ammonium chloride (NH$_4$Cl), 10 mM potassium bicarbonate (KHCO$_3$), 0.1 mM EDTA] for 8 min at room temperature. The remaining cells were washed with PBS supplemented with 2% (v/v) fetal bovine serum (FBS) (GIBCO Laboratory, Grand Island, N.Y.) and stained as described below for flow cytometry analysis.

Aortic Cell Isolation and Staining

ApoE$^{-/-}$ mice and ApoE$^{-/-}$/Casp-1$^{-/-}$ mice were fed with a HF diet for 3 weeks and sacrificed at the end of the feeding period. Their vasculatures were perfused by cardiac puncture with PBS containing 20 U/mL of heparin to remove blood cells from all vessels. The aortas were collected and digested as previously described with slight modification. Briefly, the entire mouse thoracic and abdominal aortas were isolated from the surrounding fat, minced with scissors, and digested with 125 U/mL collagenase type XI, 60 U/mL hyaluronidase type I, 60 U/ml DNase1, and 450 U/mL collagenase type I in PBS containing 20 mM 4-(2-hydroxyethyl)-1-piperazineethanesulfonic acid (HEPES) (GIBCO Laboratory, Grand Island, N.Y.) at 37° C. for 45 min. Aortic cell suspensions were then washed with Hank's balanced salt solution (HBSS) (Cellgro Mediatech, Washington, D.C.) supplemented with 2% FBS and filtered through a 70 μM cell strainer (BD Falcon, San Jose, Calif.). The passed fluid containing the suspended cells was then ready for antibody staining.

Both cells from blood samples and from aortic tissues were first stained with LIVE/DEAD® Fixable Violet dye (Invitrogen, USA) for 20 min at 4° C. to exclude dead cells, washed, and were co-incubated with three monoclonal antibodies, CD11b-phycoerythrin (PE) (BD Biosciences, monocyte marker), Ly-6C-fluorescein isothiocyanate (FITC) (BD Biosciences, an inflammatory monocyte marker) and F4/80-phycoerythrin-cyanine (PE-Cy7) (eBioscience, macrophage marker) for 30 min at 4° C. The stained cells were then fixed with 2% PFA for at least 1 hour at 4° C. and analyzed on the LSR II flow cytometer (BD Biosciences, San Jose, Calif.).

Bone Marrow Transplantation

Eight week-old ApoE$^{-/-}$ mice and ApoE$^{-/-}$/Casp-1$^{-/-}$ mice were irradiated with a single dose of nine Gy using the model 30-1 Irradiator (J.L. Shepherd & Associates, San Fernando, Calif.). The donor bone marrow (BM) cells were harvested from 8 week-old enhanced green fluorescent protein (EGFP)-transgenic mice. Briefly, BM cells were flushed out from tibia and femur with HBSS supplemented with 2% FBS and filtered through a 70 μM cell strainer. The unfractionated EGFP$^+$ BM cells (5×10$^6$ cells) were administered by retro-orbital injection into the irradiated mice 2 hours after irradiation. To assess the irradiation efficiency, a group of mice without receiving BM transplantation after irradiation was used as controls. More than 80% of the non-BM recipient control mice died after irradiation while all BM transplanted mice survived. To assess hematopoietic chimerism, peripheral blood cells were collected from the recipient mice 6 weeks after BM transplantation, and the frequency of EGFP$^+$ cells among peripheral nucleated blood cells was determined by flow cytometry after hemolysis with ACK lysis buffer. The chimeric mice were then fed a HF diet for 3 weeks, and the rates of EGFP$^+$ monocyte migration into the aorta were accessed by the single cell suspension method as described previously.

Human Aortic Endothelial Cell Culture

Human aortic endothelial cells (HAECs) (Clonetics Corporation, San Diego, Calif.) were cultured as we previously described. The cells were maintained on a 0.2% gelatin-coated 75-cm$^2$ flask in M199 (Hyclone Labs., Logan, Utah) supplemented with 20% FBS, 1% Penicillin/Streptomycin (Invitrogen, Carlsbad, Calif.), 3 ng/mL EC growth supplement (ECGS) (BD Biosciences, San Jose, Calif.), and 5 U/ml heparin at 37° C. under 5% CO$_2$, 95% air until passage 8. For our experiments, HAECs (≥passage 9) were used and treated with desired stimuli for indicated time.

Mouse Endothelial Cell Isolation and Primary Culture

Mouse aorta ECs (MAECs) were isolated and cultured as previous described with modifications. Briefly, the entire mouse thoracic aorta was exposed, perfused with PBS containing 1,000 U/mL heparin, and filled with Dulbecco's modified eagle medium (DMEM) (Hyclone Labs., Logan, Utah) plus 300 U/mL collagenase type 2 (Worthington Biochemical Corp., Freehold, N.J.) with ligation at both ends. The aorta was then isolated and incubated in 20% FBS/DMEM at 37° C. for 1 hour. The fluid inside the aorta was flushed out with 20% FBS/DMEM and drained into a 15-mL tube containing 10 mL of endothelial growth medium (EGM) [50% DMEM; 40% F-12 (Invitrogen, Carlsbad, Calif.), 10% FBS; 0.3% ECGS; 10 U/mL Heparin; 1% Penicillin/Streptomycin]. After centrifugation, all cells were collected and re-suspended with fresh EGM. The cells were then transferred into collagen-coated 35-mm dishes (2 aortas/dish) and incubated for 1 hr. The non-adhered cells were then washed away with sterile Dulbecco's phosphate-buffered saline (DPBS) (Hyclone Labs., Logan, Utah), and the MAECs were cultured with EGM until 80% confluence was achieved.

The specificity of ECs was determined by Dil-Ac-LDL uptake and CD31 staining. Briefly, Dil-Ac-LDL was added to the culture medium at the final concentration of 10 μg/mL. MAECs were incubated with the dye-labeled lipoprotein for 4 hours at 37° C. The cells were then washed twice with PBS, fixed with 4% PFA for 20 min, and stained with 4', 6-diamidino-2-phenylindole (DAPI) (1 μg/mL) for 5 min. For CD31 (platelet endothelial cell adhesion molecule-1, EC marker) staining, MAECs were cultured on a sterile cover slip and fixed with 4% PFA for 20 min before staining. Rat anti-mouse CD31 antibody (BD Pharmingen, San Diego, Calif.) and FITC conjugated rabbit anti-rat secondary antibody (Jackson ImmunoResearch Laboratories, West Grove, Pa.) were used. All images were captured with a Zeiss Axioscope microscope.

Caspase-1 Activity Assay

Active caspase-1 level was determined with APO LOGIX kit (Cell Tech., Mountain View, Calif.). The kit contains a carboxyfluorescein (FAM) [Excitation/Emission (nm):490/520]-labeled peptide fluoromethyl ketone (FMK) caspase-1 inhibitor (FAM-YVAD-FMK), which irreversibly binds to active caspase-1. All procedures were performed according to the manufacturer's instruction. Briefly, HAECs (≤passage 9) were cultured in 6-well plates and serum starved overnight to quiescent the cells before treatment. Next day, HAECs were treated with indicated stimuli for 6 hr. Cells were then digested by trypsin-EDTA and suspended at $1\times10^6$ cells/ml. 150 μl of cell suspension were incubated at 37° C. with 1× FAM-YVAD-FMK for 1 hour then washed with 1× washing buffer. Unfixed caspase-1 stained cells were then incubated with 7-aminoactinomycin D (7-AAD; cell membrane integrity marker) (BD Pharmingen, San Diego, Calif.) for no more than 10 min before analysis. The Calibur flow cytometer (BD Biosciences, San Jose, Calif.) was used to determine caspase-1 active (Caspase-1$^+$) and 7-AAD$^+$ cells. Data were analyzed with the FlowJo software (Tree Star, Ashland, Oreg.).

Reactive Oxygen Species Level Detection

Dihydroethidium (DHE) was applied to detect reactive oxygen species (ROS) levels in HAECs. DHE can be oxidized by superoxide anion, which then bind with the cell's DNA and stain its nucleus a bright red fluorescent [Excitation/Emission (nm):518/605]. For staining, suspended HAECs were incubated in 150 uL culture medium containing 3 μM DHE for 40 min at 37° C. in the dark. The samples were washed with flow cytometry washing buffer (PBS/2% FBS) and immediately analyzed by flow cytometry.

Data Analysis Using the FlowJo Software

All flow cytometric data were analyzed with the FlowJo software. The uncompensated data was collected from the flow cytometer (either Calibur flow cytometer or LSRII flow cytometer). Forward and side scatter gates were used to select live cell population from clumps and debris. The positive gate was determined by its matched IgG control, and single staining was used to determine the compensation parameter.

Protein Extraction and Western Blot Analysis

Cell pellets from HAECs were collected and lysed with protein lysing buffer [0.75% SDS, 0.03M Tris-HCl stock (pH 6.8), 5.6% glycerol, 1 mM EDTA, 0.04 mg/ml phenylmethanesulfonylfluoride (PMSF), 1× protease inhibitor tablet (Roche Applied Science, Indianapolis, Ind.)]. For aorta, the fat-free aortic tissues were collected and dissected with scissors before lysing. The cells/tissues were further lysed by sonication, and the debris was centrifuged down. The supernatant was transferred into a new tube and the protein concentration was determined by the bicinchoninic acid assay (Pierce/Thermo, Rockford, Ill.). Forty μg to 100 μg protein was loaded into a 10% sodium dodecyl sulfate polyacrylamide gels and transferred onto nitrocellulose membranes (Whatman, Clifton, N.J.), and the membranes were then stained with 1% Ponceau S for loading controls. Then the blots were blocked with 5% non-fat milk in PBST (PBS+0.1% Tween 20) for 1 hr at room temperature and probed with diluted primary antibodies overnight at 4° C. Blots were then washed 4 times with PBST and incubated with horseradish peroxidase (HRP) conjugated anti-mouse, anti-rabbit, or anti-goat secondary antibodies (Santa Cruz) for 1 hr at room temperature. After another 4 washes with PBST, the blots were then incubated with enhanced chemiluminescence (ECL) substrate for horseradish peroxidase (Pierce/Thermo, Rockford, Ill.), and the ECL intensity was detected by X-ray film exposure in a dark room. The X-ray films were developed by the SRX-101A medical film processor. The expression levels of proteins as indicated by the ECL intensity were measured with ImageJ (NIH, Bethesda, Md., USA)

RNA Extraction and Real-Time PCR

Messenger RNA (mRNA) was extracted from cultured cells or tissues using TRIzol® Reagent (Invitrogen, Carlsbad, Calif.) following the manufacturer's instruction. Briefly, the cells or tissue samples were lysed with enough TRIzol® Reagent for 5 min at room temperature and then phase separated with chloroform. After high speed centrifugation, the upper aqueous phase was collected and transferred into a new tube with an equal volume of isopropanol. The mRNA was centrifuged down at high speed for 15 min, washed twice with 70% ethanol in RNAase free water (Qiagen, Valencia, Calif.), and dissolved in RNAase free water. The mRNA concentration was determined on a Nanodrop 2000 (Thermo Fisher Scientific, San Jose, Calif.). Two μg of mRNA was then reverse transcribed into complementary DNA (cDNA) using the High-Capacity cDNA Reverse Transcription Kit (Applied Biosystems, Foster City, Calif.). For real-time PCR (RT-PCR), a SYBR-green PCR system (SABiosciences, Frederick, Md.) was used, and the real-time PCR was performed on the StepOnePlus real-time PCR system (Applied Biosystems, Foster City, Calif.).

The primers used for the real-time PCR are listed below.

```
Human NLRP 1-Forward:
                                      (SEQ ID NO: 9)
5'-AAGTGACTGCTCCATTCGGAA-3';

Human NLRP-Reverse:
                                      (SEQ ID NO: 10)
5'-CTCCGAGAACAGCTGGTCTTCT-3';

Human NLRP3-Forward:
                                      (SEQ ID NO: 11)
5'-TGAAGA GGAGTGGATGGGTT-3';

Human NLRP3-Reverse:
                                      (SEQ ID NO: 12)
5'-TTCAATGCACTGGAA TCTGC-3';

Human PYCARD-Forward:
                                      (SEQ ID NO: 13)
5'-ATGGACGCCTTGGACCTCACCG-3';

Human PYCARD-Reverse:
                                      (SEQ ID NO: 14)
5'-TGGCTTGGCTGCCGACTGAGGA-3';

Human CASPASE-1-Forward:
                                      (SEQ ID NO: 15)
5'-AGCTCCTCAGGCAGTGCAGGA-3';

Human CASPASE-1-Reverse:
                                      (SEQ ID NO: 16)
5'-AGAGCAAGACGTGTGCGGCT-3';

Human IL1β-Forward:
                                      (SEQ ID NO: 17)
5'- ACAGATGAAGTGCTCCTTCCA-3';

Human IL1β-Reverse:
                                      (SEQ ID NO: 18)
5'-GTCGGAGATTCGTAGCT GGAT-3';

Human β-actin-Forward:
                                      (SEQ ID NO: 19)
5'-ACCTTCTACAAT GAGCTGCG-3';

Human β-actin-Reverse:
                                      (SEQ ID NO: 20)
5'-CCTGGATAGCAAGTACATGG-3';

Mouse Caspase-1-Forward:
                                      (SEQ ID NO: 21)
5'-CCCTCAAGTTTTGCCCTTTAGA-3';

Mouse Caspase-1-Reverse:
                                      (SEQ ID NO: 22)
5'-CCCTCGGAG AAAGATGTTGAAA -3';

Mouse ICAM-1-Forward:
                                      (SEQ ID NO: 23)
5'-GTTCTCTAATGTCTCCGAG GC-3';

Mouse ICAM-1-Reverse:
                                      (SEQ ID NO: 24)
5'-CTTCAGAGGCAGGAAACAGG-3';

Mouse VCAM-1-Forward:
                                      (SEQ ID NO: 25)
5'-GCAAAGGACACTGGAAAAGAG-3';

Mouse VCAM-1-Reverse:
                                      (SEQ ID NO: 26)
5'-TCAAAGGGATACACATTAGGGAC-3';

Mouse E-selectin-Forward:
                                      (SEQ ID NO: 27)
5'-GCTGGAGAACTTGCGTTTAAG-3';

Mouse E-selectin-Reverse:
                                      (SEQ ID NO: 28)
5'-AGATAAGGCTT CACACTGGAC-3';

Mouse GAPDH-Forward:
                                      (SEQ ID NO: 29)
5'-GAGGCCGGTGCTGAGTATGTCG TGGA-3';

Mouse GAPDH-Reverse:
                                      (SEQ ID NO: 30)
5'-CACACCCATCACAAACTGGGGGCAT-3'.
```

Cytokine Array

A mouse cytokine array (R&D Systems, Minneapolis, Minn.) was used to determine the cytokine and chemokine expression in mouse aorta as well as in stimulated MAECs following the manufacturer's instruction. Briefly, the nitrocellulose membranes pre-spotted with 40 cytokine and chemokine antibodies were first blocked with 1× blocking buffer for 1 hr. Meanwhile, protein lysates or supernatant were incubated with the detection antibody cocktail for 1 hr. The blocked membranes were incubated with the premixed protein/antibody solutions overnight at 4° C. Then membranes were washed with 1× wash buffer three times and incubated with HRP-conjugated Streptavidin for 30 min at room temperature, and followed with another three washes with 1× wash buffer. The membranes were then incubated with the chemiluminescent reagents and exposed to X-ray films for 1-10 min. The expression levels of the cytokines and chemokines were determined by the intensity of the spots measured with ImageJ software. The variations of the manufacture's designate positive control (PC) spots between each array were used to determine the confidence interval of non-specific variations between samples Static Adhesion Assay HAECs were cultured and seeded on 24-well plates. THP-1 human monocytic cells were maintained in RPMI 1640 with 10% FBS and 2 mM L-Glutamine (GIBCO Laboratory, Grand Island, N.Y.). THP-1 cells were stained with 2 μM calcein green AM for 30 min at 37° C. Then $1×10^6$/mL THP-1 cells were suspended in 1 mL of 1640 and M199 medium (1:1) and added to HAEC monolayer. After 1 hr incubation at 37° C., unattached cells were removed by PBS washes and then the plates were read in a fluorescence microplate reader.

Preparation of Nuclear Extracts

HAECs cultured in 100-mm dishes were collected and homogenized in a low-salt buffer [10 mM HEPES (pH 7.9), 1.5 mM magnesium chloride ($MgCl_2$), 10 mM KCl, 0.2 mM phenylmethylsulfonyl fluoride (PMSF), 0.5M dithiothreitol (DTT)]. The cytoplasmic fraction was removed, and the isolated nuclei were resuspended in a high-salt buffer [20 mM HEPES (pH 7.9), 25% glycerol, 1.5 mM $MgCl_2$, 420 mM NaCl, 0.2 mM EDTA, 0.2 mM PMSF, 0.5M DT] to release soluble proteins. The nuclear protein preparation was then collected and stored at −80° C. Protein concentration was determined by the bovine serum albumin (BCA) assay (Pierce) using BSA as a standard.

Generation of Cell Permeable Human Non-Casp1 Cleavable Sirt1 Polypeptide

The specific cleavage site of Human Sirt1 by Casp1 was identified by running NIH-NCBI Blast homology search between mouse Sirt1 (NIH-NCBI protein ID: NP_062786) and human Sirt1 protein sequence (NIH-NCBI protein ID: NP_036370) (FIG. 12A). After matching mouse Casp1 cleavage site of Sirt1 (D142, Asp at the amino acid 142) identified previously (Libby et al., 2011, Nature 473:317-

25), human Casp1 cleavage site of Sirt1 (D150) was predicted and confirmed using our previously published method (Mestas and Ley, 2008, Trends Cardiovasc Med 18:228-32). Human Non-Casp1 cleavable Sirt1 (NC-Sirt1) was then generated by connecting a cell membrane permeable protein transduction sequence in the N-terminal (Jiang et al., 2005, Arterioscler Thromb Vasc Biol 24:2515-21), as shown for other cell permeable peptides in the InvivoGen, Inc., to the single site mutated sequence (D150A, replacing the caspase-1 cleavage essential amino acid Asp with the amino acid Ala) of human Sirt1 140-160 position, rendering the sequence non-Casp1 cleavable (FIG. 12B). Of note, the Sirt1 amino acids 140-149 (N-terminal to the D150 cleavage site) and Sirt1 amino acids 151-160 (C-terminal to the D150 cleavage site) were designed to secure the caspase-1 specific binding to Sirt1, as we reported (Mestas and Ley, 2008, Trends Cardiovasc Med 18:228-32). Exemplary nc-Sirt1 is set forth in SEQ ID NOs 1 and 2.

Electrophoretic Mobility Shift Assay

Transcription factor interactions with DNA response elements were assessed using electrophoretic mobility shift assay (EMSA). Activator protein-1 (AP-1) and nuclear factor kappa-light-chain-enhancer of activated B cells (NF-κB) consensus oligonucleotides end-labeled with IR700 were purchased from LI-COR (Lincoln, Nebr.). The sequences of the probes are as follows: AP-1, 5'-CGCTTGATGACTCA-GCCGGAA-3' (SEQ ID NO: 31); and NF-κB, 5'-AGTT-GAGGGGACTITCCCAGGC-3'(SEQ ID NO: 32). Unlabeled probes were purchased from Santa Cruz and were used at a 30-fold excess of labeled probe. EMSA were carried out using an Odyssey Infrared EMSA kit (LI-COR) according to the manufacturer's instructions. Three μg of nuclear extracts were added to each binding reaction. The probe and nuclear proteins were incubated for 30 min at room temperature and DNA-protein complexes were resolved on a 5% non-denaturing polyacrylamide gels afterwards. Images of gel were then obtained in an Odyssey scanner (LI-COR).

Data Analysis

All experiments were performed at least three times, and results were expressed as the mean±standard error (S.E.). Statistical comparison of single parameters between 2 groups was performed by paired Student t test. The Kruskal-Wallis 1-way ANOVA was used to compare the means of multiple groups and were followed by Dunn's test. Data were considered statistically significant if p was <0.05.

The results of the experiments are now described.

Hyperlipidemia Induces the Upregulation of Caspase-1 Expression and Caspase-1 Activation in ApOE$^{-/-}$ Aorta To examine our hypothesis that early hyperlipidemia activates the caspase-1 (Yin et al., 2013, Front Biosci 18:638-49) in the aortic tissue, we performed Western blot analysis with caspase-1 antibodies on mouse aortic protein lysates collected from wild-type (WT) mice and ApoE$^{-/-}$ mice fed a HF diet for 0, 3, and 6 weeks. Plasma lipid profiling data (FIG. 1A) showed that 3-week HF diet feeding significantly increased plasma cholesterol levels and triglyceride levels in ApoE$^{-/-}$ mice, reaching hyperlipidemic conditions (>200 mg/dL). More importantly, pro-caspase-1 expression levels (FIG. 1B) were significantly upregulated in ApoE$^{-/-}$ mouse aorta after feeding a HF diet for 3 (122%) and 6 weeks (160%), respectively. Because catalytic activation of procaspase-1 (45 kDa) into 2 smaller subunits, p20 and p10, in a protein complex termed inflammasome is required for its protease activity, we also examined the expression of activated caspase-1 p20 subunit. The results (FIG. 1B) showed that activated caspase-1 was increased in ApoE$^{-/-}$ mouse aorta fed with a HF diet for 3 weeks (604%) and 6 weeks (818%), respectively. Of note, upregulation of pro-caspase-1 induced by 6 weeks of HF diet feeding in ApoE$^{-/-}$ mouse aorta was ≈2-folds higher than that of WT mouse aorta. In contrast, activated caspase-1 p20 expression in HF diet-fed ApoE$^{-/-}$ mouse aorta was >8 folds higher than that of WT mouse aorta. With the lipid profiling data, we performed regression analysis of the lipid data against expression data of p20-activated caspase-1 detected by Western blot in FIG. 1B. We found that activated caspase-1 p20 expression in ApoE$^{-/-}$ mouse aorta was correlated well with increased plasma cholesterol levels ($R^2$=0.8096; P=0.0004<0.01) and increased triglyceride levels ($R^2$=0.7469; P=0.0013<0.01; FIG. 1C), suggesting that caspase-1 activation is tightly associated with elevated cholesterol and triglycerides levels, as early as 3 weeks of hyperlipidemia. Of note, the expression of pro-caspase-1 in non-HF diet fed ApoE$^{-/-}$ mouse aorta was not significantly higher than that in non-HF diet fed WT mouse aorta, suggesting that upregulation of procaspase-1 in HF diet-fed ApoE$^{-/-}$ mouse aorta was not because of deficiency of the ApoE gene. The results showed that hyperlipidemia also upregulated the expression of caspase-1 mRNA ≈2-folds (FIG. 1D), which was similar to the upregulation of pro-caspase-1 detected by Western blots. These results suggest that upregulation of pro-caspase-1 induced by hyperlipidemia in HF diet-fed ApoE$^{-/-}$ mouse aorta results from the hyperlipidemia-induced transcriptional mechanism and the posttranslational mechanism. As the substrate of activated caspase-1, cleaved and activated IL-1β was induced after 3 weeks of HF diet in the aortas of WT and ApoE$^{-/-}$ mice. In addition, the expression of pro-IL-1β was also induced (FIG. 1E). Taken together, the results demonstrated that early hyperlipidemia induces the upregulation of caspase-1/IL-1β expression and caspase-1/IL-1β activation in mouse aorta. Because significant monocyte recruitment into ApoE$^{-/-}$ mouse aorta does not happen until 6 weeks after HF diet feeding, these results suggest that caspase-1 is activated in aortic residential cells at the early stage of atherosclerosis.

Figures 3A, 3B:
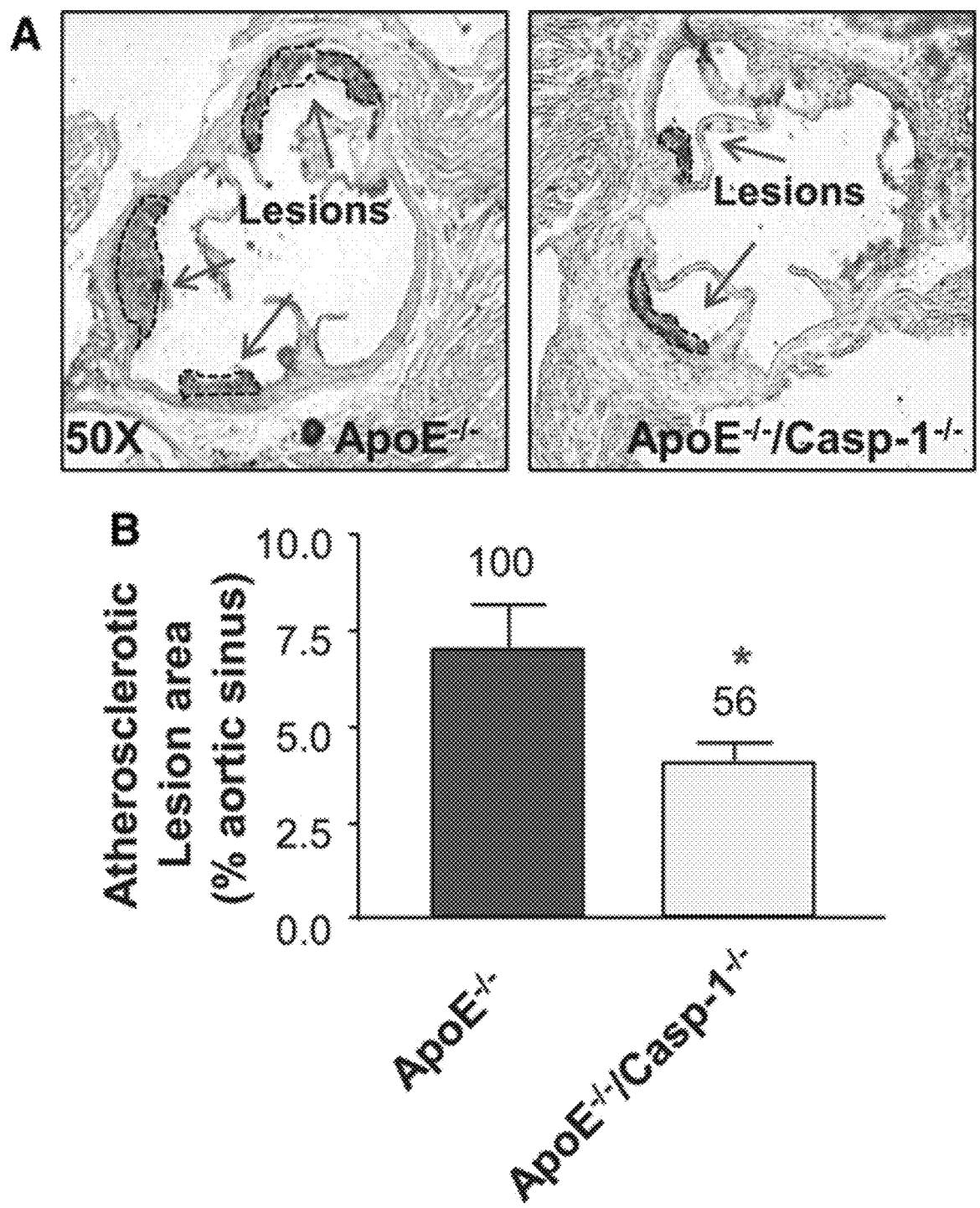
FIG. 3A and FIG. 3B, depicts experimental results showing spase-1 (casp-1) deficiency attenuates early atherosclerotic lesion formation in aortic sinus of ApoE$^{-/-}$/Casp-1$^{-/-}$ fed with a 3-week high fat (HF) diet.

Deficiency of Caspase-1 in ApoE$^{-/-}$ Background Results in Decreased Atherosclerotic Lesion in the Early Stage of Atherogenesis To examine the hypothesis that caspase-1 plays an important role in early atherogenesis, ApoE$^{-/-}$/caspase-1$^{-/-}$ double gene KO mice were generated. The protein expression of pro-caspase-1 in mouse aorta (FIG. 2A) was absent in the double KO mice, which were verified with the mouse tail genomic DNA analysis (FIG. 2A). General health, body weight, heart and spleen weights (FIG. 2B), and plasma cholesterol and triglyceride levels (FIG. 2C) of ApoE$^{-/-}$/caspase-1$^{-/-}$ mice were not significantly different from those of ApoE$^{-/-}$ mice. More importantly, after 3 weeks of HF diet, the atherosclerotic lesions in the aortic sinus area, the most sensitive atherogenic area in the aorta, of the double KO mice were significantly decreased by 44% (lesion area mean±2SD=3.92%±1.42%) compared with that of ApoE$^{-/-}$ mice (6.98/±2.67%; P=0.0147; FIGS. 3A and 3B). The results demonstrated that caspase-1 plays a critical role in promoting early atherogenesis.

Deficiency of Caspase-1 in ApoE$^{-/-}$ Background Results in Decreased Expression of Proinflammatory Cytokines and Chemokines in the Aorta Because proinflammatory cytokines and chemokines play essential roles in recruiting inflammatory cells into the aorta during atherogenesis (Hansson et al., 2011, Nat Immunol 2:204-12), to determine the molecular mechanism underlying the reduction in atherosclerotic lesion formation in ApoE$^{-/-}$/caspase-1$^{-/-}$ mice, we examined the hypothesis that the decrease in atherosclerotic lesion may be a result of the decreased generation of proinflammatory cytokines and chemokines in mouse aorta. We used an antibody array to compare simultaneously the expressions of 40 cytokines and chemokines in ApoE$^{-/-}$/caspase-1$^{-/-}$ mouse aorta and ApoE$^{-/-}$ mouse aorta (FIG. 9). The results showed that the expressions of 17 cytokines and chemokines out of 40 examined in ApoE$^{-/-}$ mouse aorta were higher than those in caspase-1$^{-/-}$/ApoE$^{-/-}$ mouse aorta. These 17 upregulated cytokines and chemokines included soluble intercellular adhesion molecule-1 (ICAM-1), chemokine (C-C motif) ligand-17 (CCL17), granulocyte-macrophage colony stimulation factor (CSF2), tissue inhibitor of metalloproteinases-1, IL-27, IL-2, CCL1, IL-23, IL-7, IL-10, IL-16, IL-1α, CCL11, CCL2, CCL4, IL-1 receptor antagonist (IL-1ra), and CCL12. Most of these cytokines and chemokines are proinflammatory except tissue inhibitor of metalloproteinases-1, IL-10, and IL-1ra, suggesting that early hyperlipidemia promotes the generation of proinflammatory cytokines and chemokines more than anti-inflammatory cytokines/chemokines, whereas caspase-1 deficiency attenuates the generation of these proinflammatory cytokines and chemokines. It has been reported previously that besides being the converting enzyme for IL-1β and IL-18 maturation, caspase-1 also serves as a regulator for the expression of IL-1α, TNF-α and IL-6 (Kuida et al., 1995, Science 267:2000-3) and for the secretion of unconventional proteins (Keller et al., 2008, Cell 132:818-31). Of note, IL-1β was not detected in ApoE$^{-/-}$ mouse aorta after 3 weeks of HF feeding, suggesting that the cytokine array used here is not sensitive enough to detect the IL-1β differences between the groups. Several proinflammatory cytokines, including IL-4, IL-5, IL-6, and IL-12, were reported to express in mouse plasma samples collected from 10-week-old HF diet fed ApoE$^{-/-}$ mice (Tabibiazar et al., 2006, Physiol Genomics 25:194-202), which was not evident in our results. This discrepancy may be because our experiments were designed to examine early hyperlipidemia (3 weeks of HF diet feeding)-induced cytokine expression. Taken together, our results suggest that deficiency of caspase-1 results in decreased expression of proinflammatory cytokines and chemokines in the aorta.

Figures 4A, 4B, 4C:
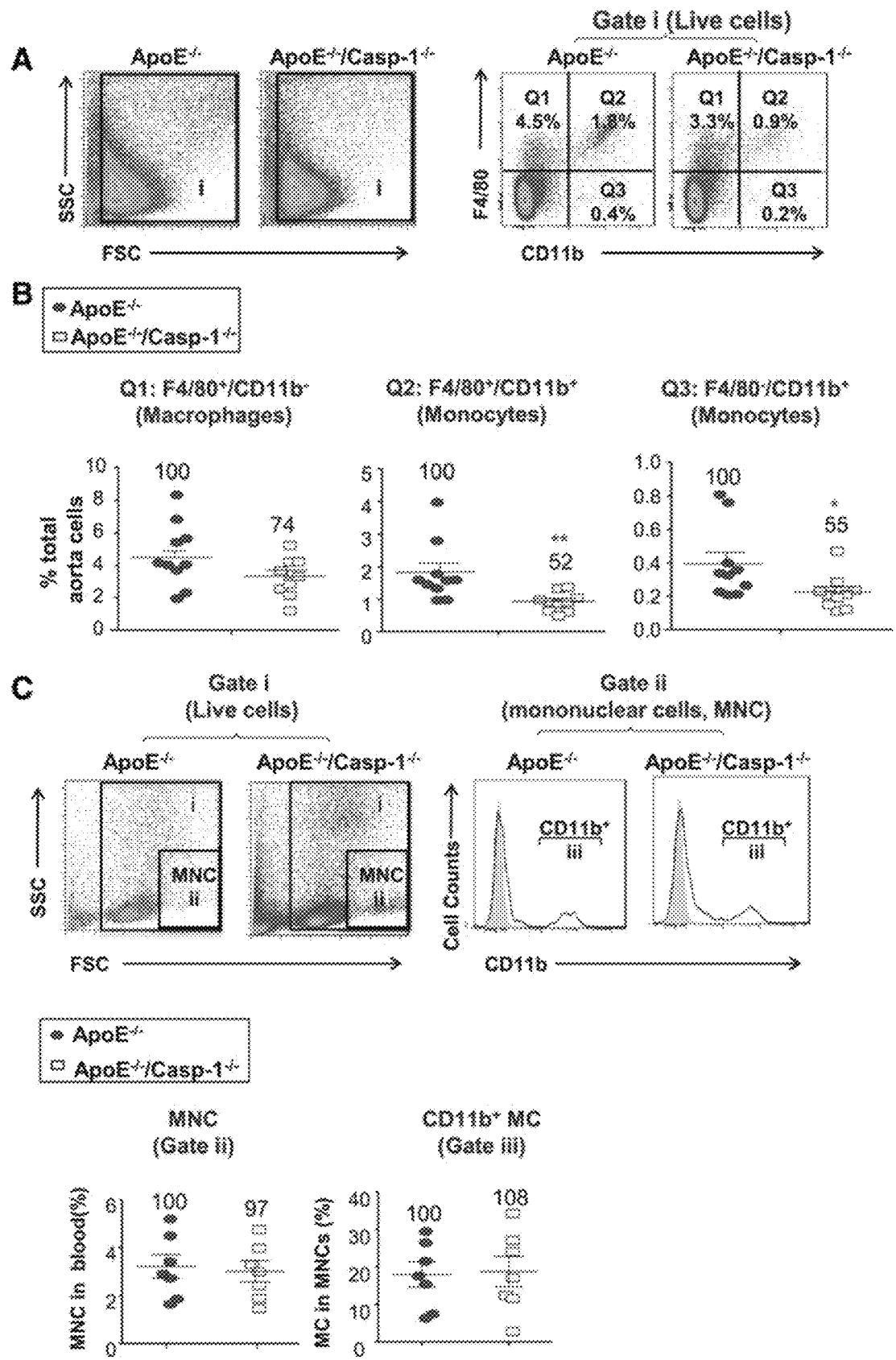
FIG. 4A through FIG. 4C, depicts experimental results showing caspase-1 (casp-1) deficiency attenuates monocyte infiltration into mouse aorta in ApoE$^{-/-}$/Casp-1$^{-/-}$ mice fed with a 3-week high fat (HF) diet.
Figure 10:
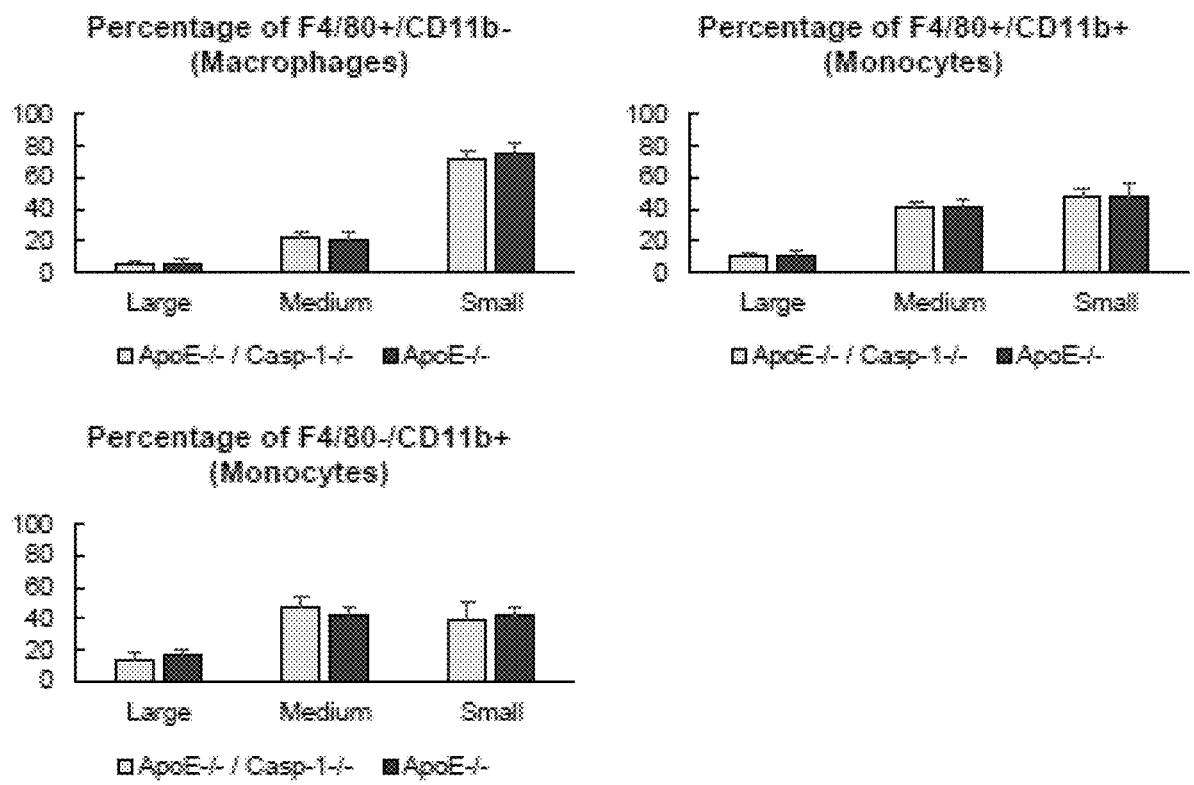
FIG. 10 depicts experimental results showing no differences are found between the proliferation of macrophages/monocytes in ApoE$^{-/-}$/Casp-1$^{-/-}$ mouse aortas and that of ApoE$^{-/-}$ mice as reflected by the cell size. Cell size is determined with the scales of forward scatter by flow cytometry as an estimate of cell proliferation status.

Deficiency of Caspase-1 in ApoE$^{-/-}$ Background Results in Decreased Recruitment of Monocytes into the Aorta Because recruitment of monocytes and other inflammatory cells into the mouse aorta and other arteries is essential for atherogenesis (Libby et al., 2011, Nature 473:317-25), based on the above results of decreased expression of inflammatory cytokines and chemokines in double KO aorta, we hypothesized that caspase-1 deficiency may result in reduced monocyte recruitment into the mouse aorta. We performed single cell analysis of mouse aortic cells with fluorescence-conjugated antibody staining for F4/80 and CD11b followed by flow cytometric analysis as reported previously (Kim et al., 2011, Immunity 34:769-80; Goncalves et al., 2011, J Exp Med 208:1253-65). The results (FIGS. 4A and 4B) showed that caspase-1 deficiency in ApoE$^{-/-}$ background decreased F4/80$^+$/CD11b$^-$ macrophage recruitment into the aorta, but the reduction did not have statistical significance (P=0.0621). In contrast, the results also showed that caspase-1 deficiency significantly decreased F4/80$^+$CD11b$^+$ monocyte recruitment into the aorta (P=0.0045) and F4/80$^-$CD11b$^+$ monocyte recruitment into the aorta (P=0.0194), respectively. In addition, we further determined whether aortic monocyte composition changes resulted from the changes in the peripheral blood. The results in FIG. 4C showed that total mononuclear cells and CD11b$^+$ monocytes in ApoE$^{-/-}$/Caspase-1$^{-/-}$ mouse blood had no statistical differences to that of ApoE$^{-/-}$ mice. Moreover, we determined whether aortic monocyte composition changes as a result of alterations in the proliferation of recruited monocytes in mouse aorta. Because cell size of cell populations detected by the forward scatter with flow cytometry could be an estimate of cell proliferation status (Böhmer et al., 2011, Cytometry A 79:646-52), the results in FIG. 10 showed that the 3 cell size fractions (large, middle, and small) in 3 cell subsets, including F4/80+CD11b$^-$ macrophages, F4/80$^+$CD11b$^+$ monocytes, and F4/80$^-$CD11b$^+$ monocytes, in ApoE$^{-/-}$/Caspase-1$^{-/-}$ mouse aortas had no statistical differences in comparison to that of ApoE$^{-/-}$ mouse aortas. Taken together, our results demonstrated that first, caspase-1 deficiency in ApoE$^{-/-}$ background decreased the recruitment of monocytes into the mouse aorta in early atherosclerosis; second, caspase-1 deficiency in ApoE$^{-/-}$ background did not significantly decrease F4/80$^+$CD11b$^-$ macrophage recruitment into the aorta in early atherosclerosis, suggesting that caspase-1 deficiency did not result in a defect of monocyte-to-macrophage differentiation in the early atherosclerosis; and third, the aortic data of caspase-1 deficiency in ApoE$^{-/-}$ background was a result of aortic recruitment of monocytes but not as a result of the percentage changes of mononuclear cell and CD11b$^+$ monocyte populations in the peripheral blood in early atherosclerosis.

Deficiency of Caspase-1 in ApoE$^{-/-}$ Background Results in Decreased Endothelial Activation, Including Reduced Cell Adhesion Molecule Expression and Attenuated Cytokine and Chemokine Secretion A significant decrease in the recruitment of monocytes into the mouse aorta without changes in the peripheral blood monocyte compositions leads to our hypothesis that caspase-1 deficiency in early atherosclerosis decreases endothelial activation rather than reducing the potency of monocyte infiltration into the mouse aorta. Endothelial activation can be examined from 2 prospective. First, we reasoned that decreased endothelial activation would result in decreased secretion of cytokines and chemokines. To examine this possibility, mouse aortic ECs (MAECs) from WT mice and caspase-1$^{-/-}$ mice were cultured and primed with 50 ng/mL lipopolysaccharide and treated with 200 μg/mL of oxidized low-density lipoprotein (oxLDL; first signals for the inflammasome activation) (Yin et al., 2009, Int J Immunopathol Pharmacol 22:311-22) for 24 hours followed with adenosine-5'-triphosphate (5 mmol/L) spike (second signal for the inflammasome activation)(Yin et al., 2013, Front Biosci 18:638-49) for 20 minutes. The antibody array results (FIG. 11) showed that caspase-1 deficiency significantly attenuated the secretion of C-X-C motif chemokine 10 (CXCL10), CCL3, CXCL2 (MIP-2) and granulocyte-macrophage colony stimulation factor levels from MAECs.

Figures 5A, 5B, 5C, 5D:
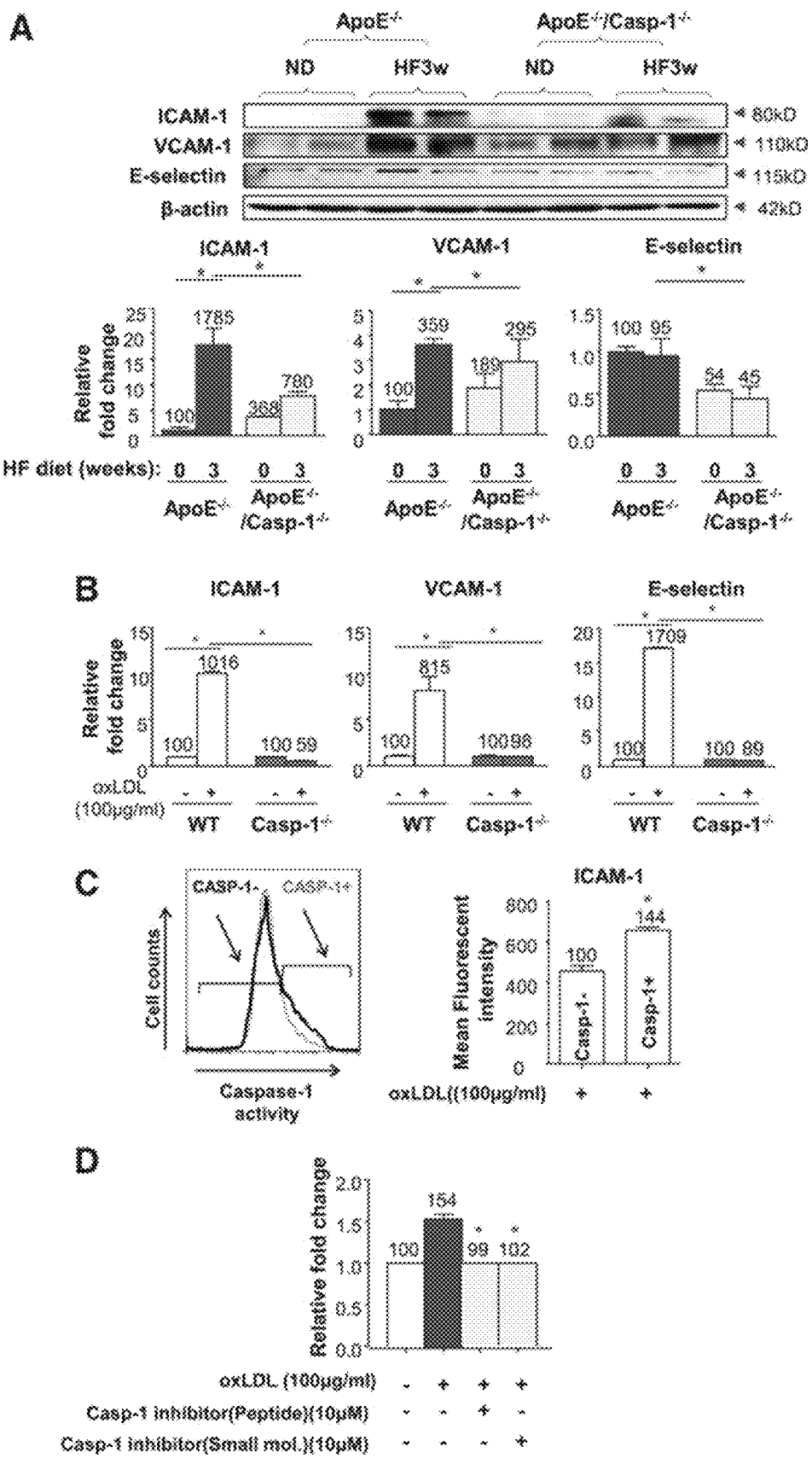
FIG. 5A through FIG. 5D, depicts experimental results showing caspase-1 (casp-1) activation regulates hyperlipidemia-induced endothelial cell (EC) activation in vivo and in vitro.

Second, we further reasoned that decreased endothelial activation in caspase-1-deficient mice would result in decreased upregulation of endothelial adhesion molecules, including ICAM-1, vascular cell adhesion molecule (VCAM)-1, and E-selectin. To examine this possibility, we first examined the adhesion molecule expression in aortas from ApoE$^{-/-}$ mice and ApoE$^{-/-}$/caspase-1$^{-/-}$ mice. The results (FIG. 5A) showed that 3 weeks of HF feeding induced upregulation of ICAM-1 (17.8-folds) and VCAM-1 (3.5-fold) protein expressions in ApoE$^{-/-}$ mouse aorta, respectively. On the contrary, HF diet feeding upregulated ICAM-1 and VCAM-1 expressions only by 2-folds and 1.5-folds, respectively, in the ApoE$^{-/-}$/caspase-1$^{-/-}$ aorta. Of note, we did not find a difference in E-selectin expression between ApoE$^{-/-}$ and ApoE$^{-/-}$/caspase$^{-/-}$ aortas. We then used RT-polymerase chain reaction to further examine the mRNA transcripts of ICAM-1, VCAM-1, and E-selectin in MAECs from WT mice and caspase-1$^{-/-}$ mice stimulated with oxLDL (100 μg/mL). The results (FIG. 5B) showed that oxLDL stimulation induced mRNA upregulation of ICAM-1, VCAM-1, and E-selectin in WT MAECs by 10-, 8-, and 17-folds, respectively. In contrast, oxLDL stimulation induced no mRNA upregulation of ICAM-1, VCAM-1, and E-selectin in caspase-1$^{-/-}$ MAECs. The differences between the protein expression of adhesion molecules in mouse aortas and their mRNA expressions in MAECs may be because in addition to ECs, some adhesion molecules are also expressed in other vascular cells, including smooth muscle cells in mouse aorta (Braun et al., 1999, Cardiovasc Res 41:395-401). Regardless of the differences between the 2 experimental systems, caspase-1 deficiency resulted in decreased induction of EC adhesion molecules ICAM-1 and VCAM-1 in mouse aorta and MAECs in response to hyperlipidemic stimulations. Because attenuation of hyperlipidemia-induced ICAM-1 upregulation by caspase-1 deficiency was most dramatic among adhesion molecules examined, we looked into the possibility that caspase-1 activity-positive ECs may have higher ICAM-1 expression than caspase-1-inactive ECs. The results (FIG. 5C) showed that ECs with active caspase-1 have higher ICAM-1 expression than caspase-1-inactive ECs, suggesting that caspase-1 activation promotes ICAM-1 upregulation and endothelial activation. Furthermore, we wanted to determine whether caspase-1 activation functionally promotes human aortic ECs (HAECs) to be more adhesive to unstimulated monocytes. Indeed, we found that oxLDL increased adhesiveness of ECs to monocytes (FIG. 5D), which were inhibited by caspase-1 inhibitors, suggesting that caspase-1 activation increases upregulation of adhesion molecules, promotes endothelial activation, and makes ECs more adhesive to monocytes.

Figures 6A, 6B, 6C, 6D, 6E, 6F, 6G:
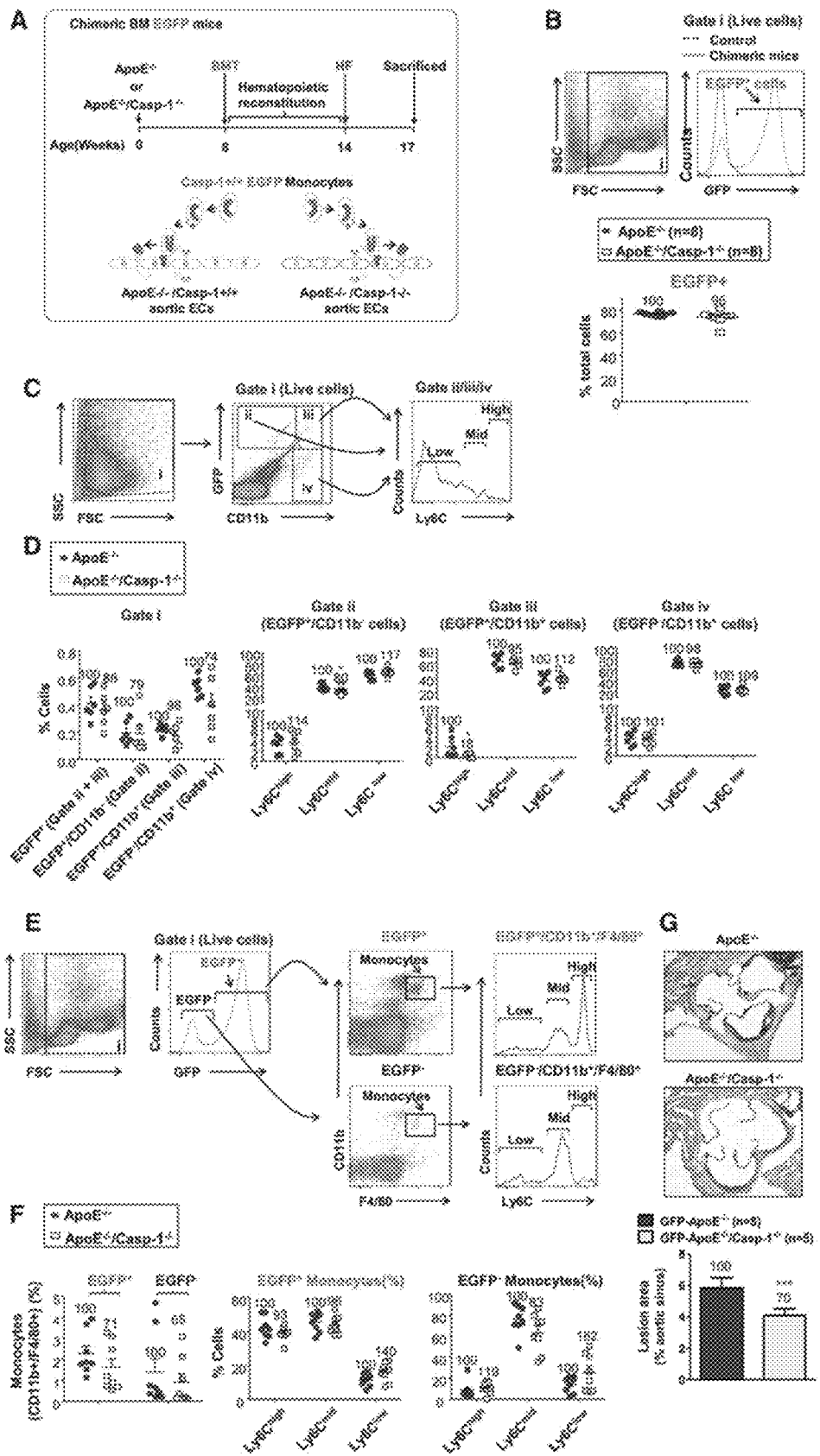
FIG. 6A through FIG. 6G, depicts experimental results showing caspase-1 (casp-1)-deficient aortas are less efficient in recruiting inflammatory monocytes during early atherogenesis.

Deficiency of Caspase-1 in the Aorta of ApoE$^{-/-}$ Mice Results in Decreased Recruitment of Transplanted Caspase-1$^{+/+}$ Bone Marrow-Derived Inflammatory Ly6C$^{middle/high}$ Monocytes into the Aorta To further consolidate our finding on the role of caspase-1 in promoting aortic endothelial activation and monocyte recruitment into the aorta, we performed chimeric bone marrow (BM) transplantation with enhanced green fluorescence protein transgenic mouse BM as the donor group and ApoE$^{-/-}$ mice and ApoE$^{-/-}$/caspase-1$^{-/-}$ mice as the 2 recipient groups (FIGS. 6A and 6B). We reasoned that if caspase-1 activation promotes endothelial activation and monocyte recruitment, then more caspase-1 activity$^+$ enhanced green fluorescence protein$^+$BM-derived Ly6C$^{middle/high}$ inflammatory monocytes should migrate into the ApoE$^{-/-}$ aorta than the ApoE$^{-/-}$/caspase-1$^{-/-}$ aorta. Indeed, we found that significantly more GFP$^+$CD11b$^-$Ly6C$^{middle}$ cells and GFP$^+$CD11b$^+$Ly6C$^{high}$ BM-derived monocytes migrated into the ApoE$^{-/-}$ aorta than the ApoE$^{-/-}$/caspase-1$^{-/-}$ aorta (FIGS. 6C and 6D; P<0.05). As control experiments, we examined the peripheral blood monocyte subsets in the 2 recipient mouse groups. In contrast, we did not find any significant difference in peripheral blood monocyte subsets between the 2 recipient groups (FIGS. 6E and 6F). In addition, after caspase-1$^{+/+}$(WT) GFP transgenic BM cell transplantation into either ApoE$^{-/-}$ recipient mice or caspase-1$^{-/-}$/ApoE$^{-/-}$ double gene KO recipient mice, caspase-1$^{-/-}$/ApoE$^{-/-}$ double gene KO recipient mice had significantly less atherosclerotic lesions than ApoE$^{-/-}$ recipient mice (FIG. 6G). Although that ECs are not the only vascular residential cells that have caspase-1 activation in response to inflammatory stimuli (Young et al., 2000, J Exp Med 191:1535-44) and that EC-specific role of caspase-1 may ultimately require the model of EC-specific deficient mice of caspase-1, the results correlated well with our previous findings and suggested that caspase-1 activation in aortic ECs promotes monocyte recruitment into the aorta.

Figures 7A, 7B, 7C, 7D:
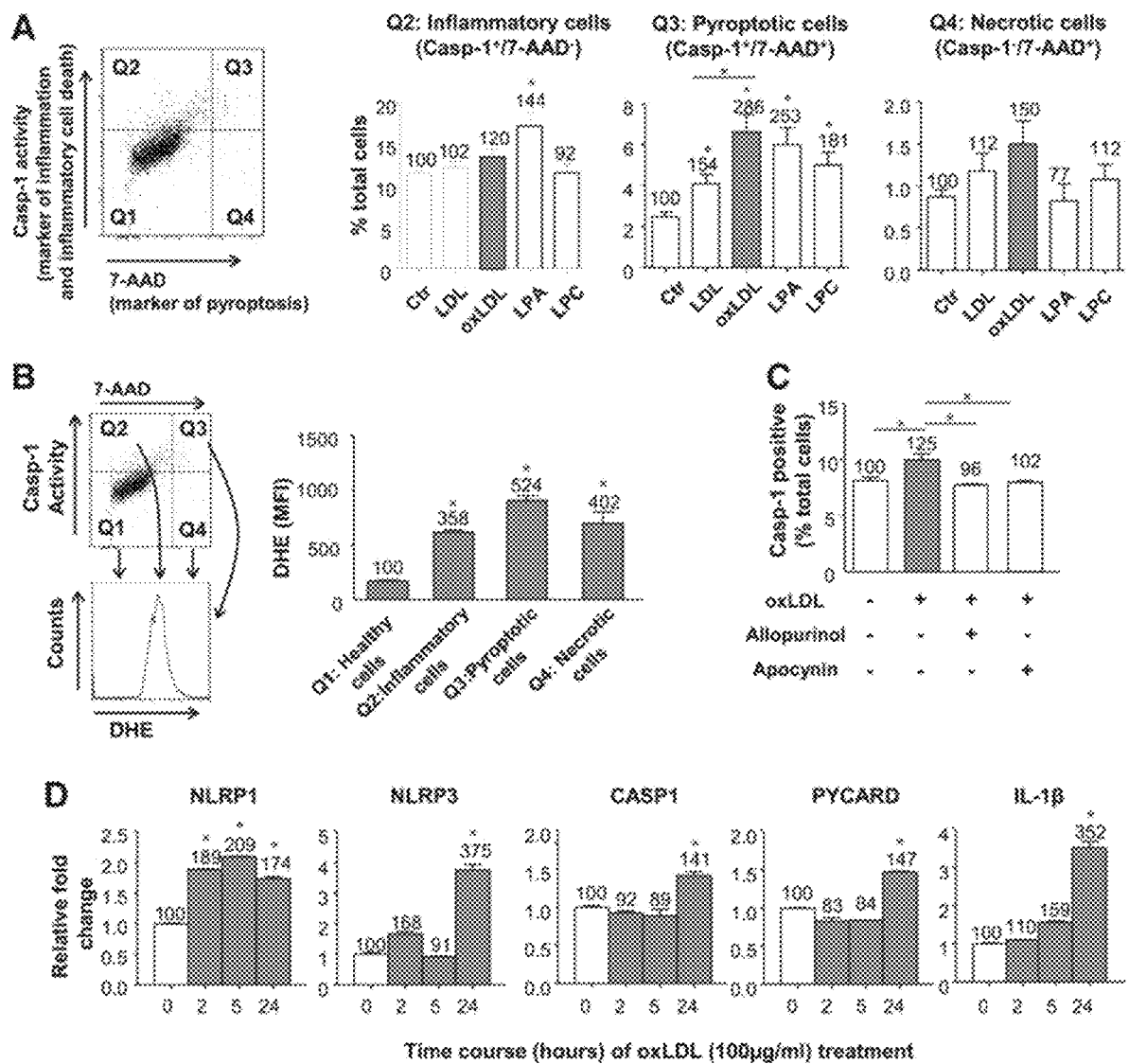
FIG. 7A through FIG. 7D, depicts experimental results showing Oxidized low-density lipoprotein (oxLDL) and its components induce caspase-1 (casp-1) activation in human aortic endothelial cells (HAECs) via a reactive oxygen species (ROS)-mediated p-athway.

Atherogenic Lipid Products Induce Caspase-1 Activation and Endothelial Inflammation Via a Reactive Oxygen Species-Dependent Pathway Our data demonstrated that caspase-1 plays a critical role in promoting EC activation and monocyte recruitment into the mouse aorta exposed to hyperlipidemia. To further determine whether atherogenic lipid products induce caspase-1 activation in ECs and whether reactive oxygen species (ROS) plays any role in caspase-1 activation in ECs, we used oxLDL and 2 oxLDL derivatives, lysophosphatidic acid (lysoPA), and lysophosphatidylcholine (lysoPC) (Zhou et al., 2011, Cell Metab 13:592-600) to stimulate HAECs. Because plasma membrane rupture and caspase-1 activation are 2 key features of the newly characterized inflammatory cell death (pyroptosis) (Miao et al., 2010, Nat Immunol 11:1136-42), in addition to using a flow cytometry-based fluorescence-labeled caspase-1 enzymatic activity assay to detect caspase-1 activation, we also used fluorescence dye 7-AAD to measure plasma membrane integrity. We classified caspase-1 enzymatically active (caspase-1$^+$) and 7AAD$^-$ (caspase-1$^+$/7-AAD$^-$) cells as inflammatory ECs, caspase-1$^+$/7-AAD$^+$ cells as pyroptotic cells, and caspase-1$^-$/7-AAD$^+$ cells as necrotic cells. We found that oxLDL, lysoPA, and lysoPC induced inflammation, inflammatory cell death (pyroptosis), and necrosis after 6-hour stimulation in HAECs (FIG. 7A). We then examined whether ROS plays any role in oxidized lipids-induced caspase-1 activation by costaining inflammatory, pyroptotic, and necrotic ECs with ROS probe dihydroethidium. Our results showed that the mean fluorescence intensities of dihydroethidium stain in ruptured cells (either pyroptotic cells or necrotic cells) were higher than that of the inflammatory cells (FIG. 7B), suggesting that oxidized lipids increased ROS-mediated caspase-1 activation and that cell death requires higher ROS levels to trigger than inflammation. We further verified the results with ROS inhibitors allopurinol (xanthine oxidase inhibitor) and apocynin (NADPH oxidase inhibitor) for inhibition of caspase-1 activation (FIG. 7C). Finally, we examined whether oxLDL induces upregulated caspase-1 and inflammasome component transcripts in ECs. The RT-polymerase chain reaction results (FIG. 7D) showed that treatment of oxLDL for 24 hours upregulated significantly NLRP1, NLRP3, caspase-1, PYCARD, and IL-1β transcripts. Because inflammasome assembly for caspase-1 activation requires NLRP, PYCARD, and procaspase-1, and effective upregulation of transcription of inflammasome and caspase-1 occurs ≈24 hours after stimulation, these results suggest that post-translational caspase-1 activation is much earlier than upregulation of caspase-1 and inflammasome transcription in ECs.

Caspase-1 Activation in the Mouse Aorta and Human Aortic Endothelial Cells Decreases the Expression of Anti-Inflammatory Protein/Histone Deacetylase Sirt1 by Cleaving Sirt1

As we detected only weak active IL-1β expression in the mouse aorta (FIG. 1E) in ApoE$^{-/-}$ mice after 3 weeks of HF diet, we hypothesized that the effect of caspase-1 activation on endothelial activation is probably contributed more by other pathways rather than the IL-1β pathway. Thus, we attempted to search for novel substrate of caspase-1 that could modulate inflammation and endothelial activation.

Figure 8A:
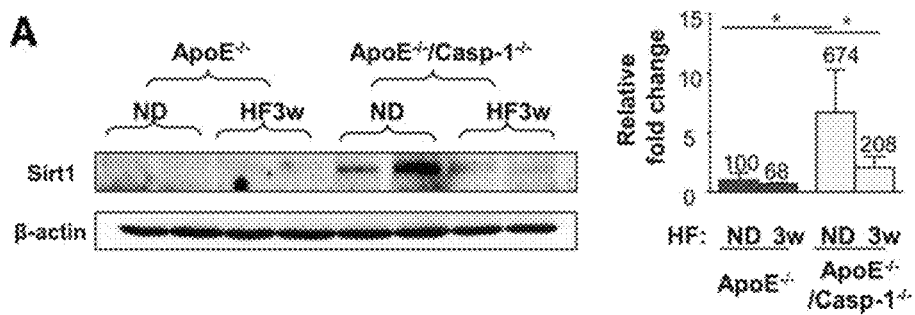
FIG. 8A through FIG. 8C, depicts experimental results showing hyperlipidemia/dyslipidemia decreases sirtuin 1 (Sirt1) expression in ApoE$^{-/-}$ mouse aorta and induces Sirt1 cleavage in human aortic endothelial cells (ECs) through caspase-1 (casp-1) activation.
Figure 8B:
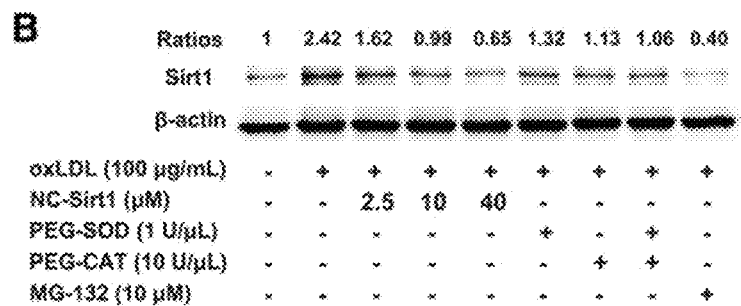

Among 24 experimentally verified caspase-1 substrates that we found in a literature search (Shen et al., 2010, Atherosclerosis 201:422-9), Sirt1 has recently been suggested to be cleaved by caspase-1 (Chalkiadaki and Guarente, 2012, Cell Metab 16:180-8). Because Sirt1 has previously been reported to regulate endothelial activation and has antiatherogenic function (Zhang et al., 2008, Cardiovasc Res 80:191-9), we then hypothesized that caspase-1-deficient mouse aorta has accumulation of noncleaved Sirt1. To test this hypothesis, we examined Sirt1 expression by Western blot with Sirt1 antibody in the following 4 groups of mice (2 mice/group): (1) ApoE$^{-/-}$ mice fed a normal chow diet; (2) ApoE$^{-/-}$ mice fed a HF diet; (3) ApoE$^{-/-}$/caspase-1$^{-/-}$ mice fed a normal chow diet; and (4) ApoE$^{-/-}$/caspase-1$^{-/-}$ mice fed a HF diet. Our results showed that compared with ApoE$^{-/-}$ aorta fed a normal chow diet, ApoE$^{-/-}$/caspase-1$^{-/-}$ aorta expressed significantly higher amount of Sirt1 (FIG. 8A). HF-fed ApoE$^{-/-}$/caspase-1$^{-/-}$ aorta had decreased Sirt1 accumulation to ⅓ of the level of ApoE$^{-/-}$/caspase-1$^{-/-}$ mice fed a normal chow diet. These results suggest that a HF diet induces other proteinase(s) activities, which participate in Sirt1 cleavage in the absence of caspase-1. Of note, plasma cholesterol levels in ApoE$^{-/-}$ mice and ApoE$^{-/-}$/caspase-1$^{-/-}$ mice (FIG. 2C) were in the range of 220 to 320 mg/dL, which were a few folds higher than those in WT mice (average 109 mg/dL; FIG. 1A). Our results suggest that caspase-1 activation induced by moderate hyperlipidemia is responsible for cleaving Sirt1 and hyperlipidemia induced by HF feeding further triggers additional uncharacterized proteinase(s) to cleave/degrade Sirt1. Then, we examined whether oxLDL decreases Sirt1 expression in HAECs by caspase-1 cleavage mechanism. The results (FIG. 8B) showed that oxLDL induced the expression of cleaved-Sirt1 by 2.4-folds in HAECs. To examine whether the induced cleavage form of Sirt1 was the result from the specific enzyme activity of Casp1, we designed a new cell permeable noncleavable Sirt1 (NC-Sirt1) by replacing the aspartate (D) in the amino acid position 150 of human Sirt1 with alanine (A), the specific cleavage site of Sirt1 recognized by Casp1 (Chalkiadaki and Guarente, 2012, Cell Metab 16:180-8) (FIG. 12). Our results showed that NC-Sirt1 dose-dependently decreases the cleavage of Sirt1 induced by oxLDL. In addition, 2 different ROS scavengers (PEG-SOD and PEG-catalase) independently and synergistically inhibit oxLDL-induced, Casp1-mediated Sirt1 cleavage. Furthermore, the proteasome inhibitor MG-132 inhibited oxLDL-induced Sirt1 cleavage, suggesting that the cleaved Sirt1 may be further subjected to a putative proteolysis by an uncharacterized proteasome-controlled proteinase. Thus, when MG-132 inhibits proteasome, the expression of this uncharacterized proteasome-controlled proteinase is increased, which leads to decreased expression of caspase-1 cleaved Sirt1. These results suggest that oxLDL first increases ROS, which promotes caspase-1 activation for cleaving Sirt1. We then used the PeptideCutter database of the Swiss Institute of Bioinformatics to analyze the potential enzymes that can cleave the human Sirt1 protein sequence. The results (Table 1) showed that caspase-1 and caspase-3 are among the enzymes that can cleave Sirt1 and are regulated by ROS, although the predicted cleavage site on Sirt1 for caspase-1 is not the same one as experimentally determined (Chalkiadaki and Guarente, 2012, Cell Metab 16:180-8). Taken together, our results suggest that caspase-1 in the mouse aorta and HAECs cleaves Sirt1 protein in response to hyperlipidemic stimuli.

TABLE 1

Predicted proteinases for humin Sirt1 protein cleavage.

| Name of Enzyme | Predicted No. of cleavages | Predicted positions of cleavage sites | Regulated by Apocynin | PMID |
| --- | --- | --- | --- | --- |
| Caspase-1 | 1 | 528 | Yes | N/A |
| Caspase-3 | 1 | 242 | Yes | 19592621 |
| Caspase-7 | 1 | 242 | Not Tested | N/A |
| Thrombin | 1 | 202 | Not Tested | N/A |
| Caspase-10 | 0 | | | N/A |
| Caspase-2 | 0 | | | N/A |
| Caspase-4 | 0 | | | N/A |
| Caspase-5 | 0 | | | N/A |
| Caspase-6 | 0 | | | N/A |
| Caspase-8 | 0 | | | N/A |
| Caspase-9 | 0 | | | N/A |
| Enterokinase | 0 | | | N/A |
| Factor Xa | 0 | | | N/A |
| Granzyme B | 0 | | | N/A |

Figure 8C:
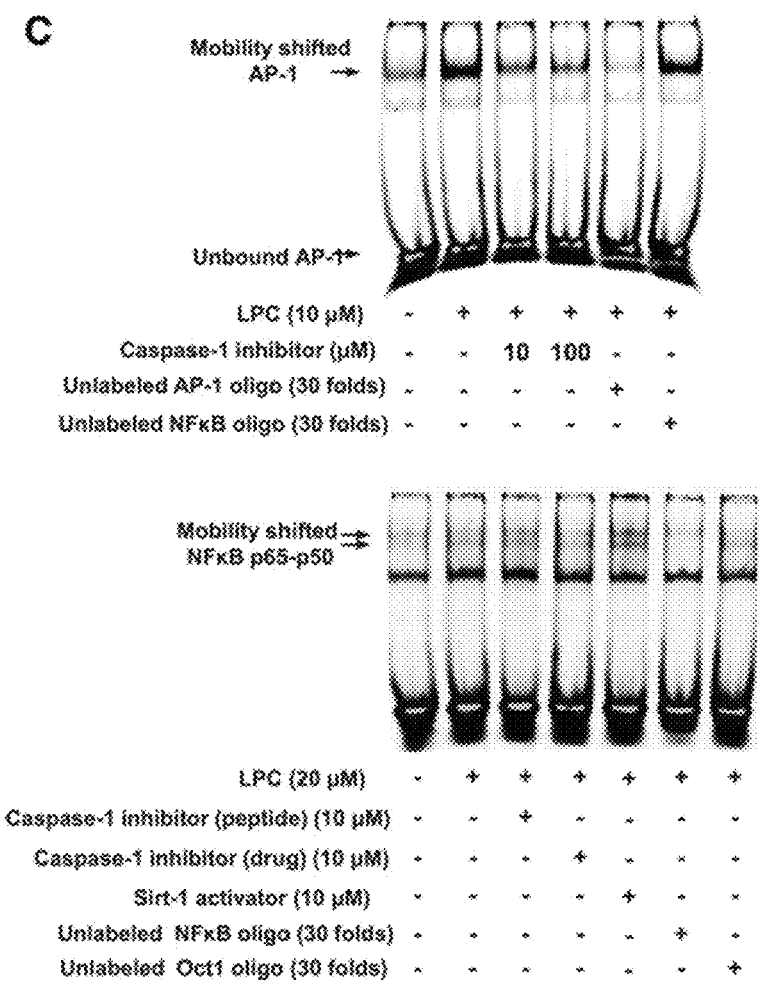

Caspase-1 Activation Induces Expression of Cytokines, Chemokines, and Adhesion Molecules Via an Sirt1-AP-1-Mediated Pathway Our data showed that caspase-1 activation induces the upregulation of several EC activation-associated cytokines, chemokines, and endothelial adhesion molecules. To further explore the mechanism underlying this caspase-1 function, we hypothesized that caspase-1 activation leads to a Sirt1-controlled transcription factor pathway to regulate these genes. Among the transcription factors that are modulated by Sirt1 are AP-1 (Zhang et al., 2010, J Biol Chem 285: 7097-10) and NF-κB (Yang et al., 2012, PLoS One 7:e46364). We examined whether lysoPC-activated AP-1 activity and NF-κB activity can be inhibited by caspase-1 inhibitors by performing electrophoretic mobility shift assay. The results (FIG. 8C) showed that lysoPC-induced AP-1 binding to AP-1 consensus nucleotides were inhibited by caspase-1 inhibitor, whereas lysoPC-activated NF-κB binding to NF-κB consensus probe was not significantly affected by caspase-1 inhibitors. We then searched for published experimental evidence that caspase-1-induced cytokines, chemokines, and adhesion molecules (FIGS. 6, 9 and 11)) are AP-1 targeted genes. The results (Table 2) showed that 11 out of 14 caspase-1-induced genes are experimentally verified AP-1 pathway-induced genes.

In addition, analysis from the microarray experimental results of Sirt1 gene-deficient mice in comparison to WT mice showed that the expression of these AP-1-targeted genes are increased in Sirt1-deficient mice (Table 2), suggesting that Sirt1 inhibits the expression of AP-1 targets. Moreover, the data-mining results (Table 3) showed that the expressions of AP-1 genes themselves, including Jun and Fos, are increased in Sirt1 1-deficient mice. Taken together, the results suggest that caspase-1-cleavable Sirt1 inhibits the expression of caspase-1-induced cytokines, chemokines, and adhesion molecules by suppressing AP-1 gene transcription and AP-1-targeted gene transcription, which further suggest that caspase-1 induces the expression of cytokines, chemokines, and adhesion molecules in ECs by cleavage and inhibition of Sirt1.

TABLE 2

| Gene ID | PMID (Ap1 Target genes) | Fold Change | p | Microarray data obtained via mining Comparison | PMID |
|---|---|---|---|---|---|
| CCL1*† | 22311973 | 1.456 | 0.0084 | Sirt1 (−/−) vs. WT | 22715468 |
| CCL2* | 8630731 | 2.364 | 0.0155 | Sirt1 (−/−) vs. WT With HFD | |
| CCL3† | 14747532 | 8.623 | 0.0000 | Sirt1 (−/−) vs. WT With HFD | 22883230 |
| CCL4* | 18789903 | 2.736 | 0.0000 | Sirt1 (−/−) vs. WT With HFD | |
| CCL17* | 14747532 | 1.591 | 0.0010 | Sirt1 (−/−) vs. WT With LFD | |
| GM-CSF*† | 9190901 | 2.265 | 0.0084 | Sirt1(−/+) vs. Sirt1(+/+) | 22006157 |
| CXCL12† | 17393416 | 1.813 | 0.0172 | Sirt1 (−/−) vs. WT | 22169038 |
| | | 1.184 | 0.0469 | Sirt1 (−/−) vs. WT With LFD | 22883230 |
| IL2* | 1737937 | 1.339 | 0.0258 | Sirt1 (−/−) vs. WT | 22715468 |
| | | 1.372 | 0.0024 | Sirt1 (−/−) vs. WT | |
| EBI3* | 15728491 | 1.484 | 0.0032 | Sirt1 (−/−) vs. WT With HFD | |
| (IL27)* | | 2.014 | 0.0004 | Sirt1 (−/−) vs. WT With LFD | |
| | | 3.018 | 0.0021 | Sirt1 (−/−) vs. WT With HFD | |
| TIMP1* | 10051488 | 1.435 | 0.0068 | Sirt1 (−/−) vs. WT With LFD | 22883230 |
| | | 1.638 | 0.0003 | Sirt1 (−/−) vs. WT With HFD | |
| VCAM1‡ | 1379595 | 1.169 | 0.0445 | Sirt1 (−/−) vs. WT With LFD | |
| | | 1.824 | 0.0285 | Sirt1 (−/−) vs. WT | 22169038 |
| IL16* | 9990060 | 1.433 | 0.0213 | Sirt1 (−/−) vs. WT | |
| | | 1.306 | 0.0055 | Sirt1 (−/−) vs. WT With LFD | |
| CCL12* | Not found | 3.764 | 0.0054 | Sirt1 (−/−) vs. WT With LFD | 22883230 |
| | | 1.317 | 0.0248 | Sirt1 (−/−) vs. WT With LFD | |
| IL7* | Not found | | | | |
| | | 2.262 | 0.0115 | Sirt1(−/+) vs. Sirt1(+/+) | 22006157 |

TABLE 3

| Gene | Fold Change | p | Compares | PMID |
|---|---|---|---|---|
| Jun | 1.778 | 0.000495 | Sirt1 KO vs. WT with LFD | 22883230 |
| Fos | 3.523 | 0.017899 | Sirt1 KO vs. WT with LFD | 22883230 |
| Fosl1 | 3.022 | 0.000628 | Sirt1 KO vs. WT with HFD | 22883230 |

Hyperlipidemia Induces Endothelial Activation

Although the role of caspase-1 in atherogenesis remains controversial (Menu et al., 2011, Cell Death Dis 2:e137), the prevailing concept is that caspase-1 plays a proatherogenic role, which is supported by results collected from ApoE$^{-/-}$/caspase-1$^{-/-}$ mice (Gage et al., 2012, Can J Cardiol 28:222-9; Usi et al., 2012, Biochem Biophys Res Commun 425:162-8), inflammasome sensor NLRP3 KO BM cells in LDL receptor (LDLR)$^{-/-}$ mice (Duewell et al., 2010, Nature 464:1357-61), ApoE$^{-/-}$/IL-1β$^{-/-}$ mice (Kirii et al., 2003, Arterioscler Thromb Vasc Biol 23:656-60), and ApoE$^{-/-}$/IL-18$^{-/-}$ mice (Elhage et al., 2003, Cardiovasc res 59:234-40). Of note, Gage et al (Gage et al., 2012, Can J Cardiol 28:222-9) and Usui et al (Usi et al., 2012, Biochem Biophys Res Commun 425:162-8) studied the role of caspase-1 deficiency in full-blown atherosclerosis in ApoE$^{-/-}$ mice after HF feeding for 8 weeks (Gage et al., 2012, Can J Cardiol 28:222-9) and 12 weeks (Usi et al., 2012, Biochem Biophys Res Commun 425:162-8). In addition, it has been reported that NLRP3 mediates hemodynamic-induced EC activation (Xiao et al., 2013, Circulation 128:632-42) and that the IL-1β mRNA/protein as well as NLRP3 mRNA are upregulated in 30 week HF feeding-induced atherosclerotic lesion and endothelium of diabetic pigs (Li et al., 2013, PLoS One 8:e67532). Along the line, we further asked whether in the early atherogenesis associated with early hyperlipidemia induced by only 3 week HF feeding, caspase-1 activation, as metabolic stress-related danger signal-associated molecular pattern-sensing pathway (Yin et al., 2013, Front Biosci 18:638-49), could be involved in endothelial activation. Using biochemical, immunologic, and pathological approaches and our newly generated ApoE$^{-/-}$/caspase-1$^{-/-}$ mice, we addressed this question and have the following results: (1) early hyperlipidemia induces the upregulation of caspase-1 expression and caspase-1 activation in ApoE$^{-/-}$ aorta, which supports our previously proposed 3-tier/inflammation privilege model for determining tissue readiness to caspase-1 activation and inflammation initiation (Yin et al., 2009, Int J Immunopathol Pharmacol 22:311-22); (2) caspase-1 deficiency in ApoE$^{-/-}$ background results in decreased early atherosclerotic lesion formation, suggesting that caspase-1 activation in ECs promotes early atherogenesis; and (3) caspase-1 deficiency in ApoE$^{-/-}$ background results in decreased expression of proinflammatory cytokines and chemokines in the aorta. Of note, the expression of 2 anti-inflammatory cytokines IL-10 and IL-1ra were also decreased in caspase-1-deficient aorta. However, the decreased expressions of as many as 15 proinflammatory cytokines in caspase-1-deficient aorta outweigh concomitant reduction of 2 anti-inflammatory cytokines, suggesting that caspase-1 activation promotes an inflammatory environment and a chemokine gradient more than anti-inflammatory environment for the recruitment of monocytes and other inflammatory cells into the aorta; (4) caspase-1 deficiency in ApoE$^{-/-}$ background results in decreased recruitment of monocytes into the aorta but has no significant role in monocyte composition in the peripheral blood in the early stage of atherosclerosis, suggesting that caspase-1 activation promotes monocyte recruitment into the aorta presumably via promoting endothelial activation and not via increasing monocyte compositions in the peripheral blood; (5) caspase-1 deficiency in ApoE$^{-/-}$ background results in decreased endothelial activation, including reduced cell adhesion molecule expression and attenuated cytokine and chemokine secretion, suggesting that increased caspase-1 activities promote endothelial activation; (6) caspase-1 deficiency in ApoE$^{-/-}$ mice results in decreased recruitment of transplanted caspase-1$^+$ BM-derived inflammatory Ly6C$^{middle/high}$ monocytes into the caspase-1$^{-/-}$ aorta, suggesting that caspase-1 activation can lead to endothelial activation, which subsequently recruits more monocyte into the aorta. Decreased recruitment of caspase- 1+ BM-derived inflammatory Ly6C$^{middle/high}$ monocytes into the caspase-1$^{-/-}$ aorta results in less atherosclerosis than caspase-1$^{+/+}$ aorta. To further determine the underlying molecular signaling mechanisms, we found (7) atherogenic lipid products induce caspase-1 activation and endothelial inflammation via a ROS-dependent pathway; (8) caspase-1 deficiency in ApoE$^{-/-}$/caspase-1$^{-/-}$ aorta and inhibition of caspase-1 in ECs result in accumulation of anti-inflammatory protein/histone deacetylase Sirt1, which is a substrate of caspase-1, suggesting that caspase-1 activation in early atherogenesis promotes endothelial activation via a Sirt1 pathway; and (9) caspase-1 activation induces the upregulation of cytokines, chemokines, and adhesion molecules in ECs via a Sirt1-AP-1-mediated pathway.

Although our previous report showed that caspase-1 can cleave numerous protein substrates (Shen et al., 2010, Atherosclerosis 201:422-9), it is generally considered that caspase-1 fulfills its proinflammatory functions predominately by cleaving pro-IL-1β and pro-IL-18 into mature IL-1β and IL-18, respectively. Although the role of proinflammatory cytokines IL-1β (Kirii et al., 2003, Arterioscler Thromb Vasc Biol 23:656-60) and IL-18 (Elhage et al., 2003, Cardiovasc res 59:234-40), as the classical substrates of caspase-1, in the promotion of atherosclerosis has been reported, the role of caspase-1, IL-1β, and IL-18 in promoting EC activation in the early stage of atherogenesis remained unknown. As defined by Ross' laboratory in ApoE$^{-/-}$ mice (Nakashima et al., 1994, Arterioscler Thromb 14:133-40), early atherosclerosis is the initiative stage precedent the occurrence of a large number of monocyte recruitment before 6 weeks of HF feeding in ApoE$^{-/-}$ mice. Our results were well correlated with a previous report that IL-1β secretion from human ECs are 70.6-folds lower than that secreted from human monocytes (Wilson et al., 2007, Br J Pharmacol 151:115-27), suggesting that IL-1β role in ECs may not be as significant as that in monocytes. These results indicate that caspase-1 may not only act through an IL-1β- or IL-18-dependent pathway to promote endothelial activation. Instead, we found that caspase-1 activation in mouse aorta in early atherogenesis and in human aortic ECs stimulated by oxLDL promotes endothelial activation via a Sirt1-inhibitable pathway. It was reported that Sirt1 reduces endothelial activation (Stein et al., 2010 Aging 2:353-60), and overexpression of Sirt1 in ECs inhibits atherosclerosis (Zhang et al., 2008, Cardiovasc Res 80:191-9). Mechanistically, adenovirus-mediated overexpression of Sirt1 significantly inhibits PMA (phorbol 12-myristate 13-acetate)/ionomycin-induced ICAM-1 expression in human umbilical vein ECs, whereas knockdown of Sirt1 by RNA interference results in increased expression of ICAM-1 and increases NF-κB p65 binding ability to the ICAM-1 promoter by Chip assays in human umbilical vein endothelial cells (Jia et al., 2013, Sci China Life Sci 56:19-25). However, the issue of whether caspase-1 in aortic ECs senses hyperlipidemia to initiate vascular inflammation via inhibiting Sirt1 was not examined until this report. Taken together, our results demonstrate a novel mechanism in early atherosclerosis: caspase-1 promotes EC activation and monocyte recruitment via decreasing Sirt1 expression and activating AP-1 pathway. The novel caspase-1-Sirt1-AP-1 pathway and the classical caspase-1-IL-1β-IL-18 are not mutually exclusive. HF diet feeding for >6 weeks promoted monocyte recruitment into the aorta (Nakashima et al., 1994, Arterioscler Thromb 14:133-40), thus, the classical caspase-1-IL-1β and Il-18 pathway in recruited monocytes and macrophages may interplay with caspase-1-Sirt1-AP-1 pathway in ECs during later stages of atherosclerosis.

Endothelial activation is the first and essential step for atherogenesis, which includes 2 molecular events-upregulation of cell surface adhesion molecules to make ECs more adhesive and increased secretion of proinflammatory cytokines and chemokines to attract monocytes and other inflammatory cells for transendothelial recruitment (Yang et al., 2008, Drug Discov Today Ther Strateg 5:125-420). Monocytes and macrophages play an essential role in promoting atherogenesis; however, we reason that if ECs are not activated during the initiation of atherogenesis, then no monocytes in the peripheral blood can be recruited into the aorta. Our results showed that caspase-1 deficiency did not alter the composition of peripheral blood monocytes and macrophages in early hyperlipidemia but instead significantly decreased aortic monocyte recruitment, suggesting that caspase-1-deficient ECs are less activated for recruitment of monocytes into the aorta. These findings were further supported by our BM transplantation results, as well as the decreased ICAM-1 and VCAM-1 and proinflammatory cytokine and chemokine expressions/secretion in HAECs and in caspase-1-deficient mouse aorta. A recent report showed that suppression of monocyte recruitment results in removal of macrophage from atherosclerotic plaques of ApoE$^{-/-}$ mice (Potteaux et al., 2011, J Clin Invest 121:2025-36), which echoes the importance of our finding. It has been reported that chemokine CXCL16 and its receptor CXCR6 play a critical role in mediating T cell migration into aorta during atherogenesis (Sheikine and Sirsjö, 2008, Atherosclerosis, 197:487-95). To determine whether CXCL16 and CXCR6 expressions are regulated by caspase-1 pathway, we searched extensively the National Institute of Health-GeoProfile microarray database and found that both CXCL16 and its receptor CXCR6 expressions are downregulated in caspase-1 KO mice microarray in comparison to that in WT control microarray (Geo-data set GDS3925), suggesting that caspase-1 activation promotes CXCL16 and CXCR6 expression and presumably T cell migration into aorta during atherogenesis. Thus, T cell migration into caspase-1$^{-/-}$/ApoE$^{-/-}$ mouse aortas may be decreased.

Figure 13:
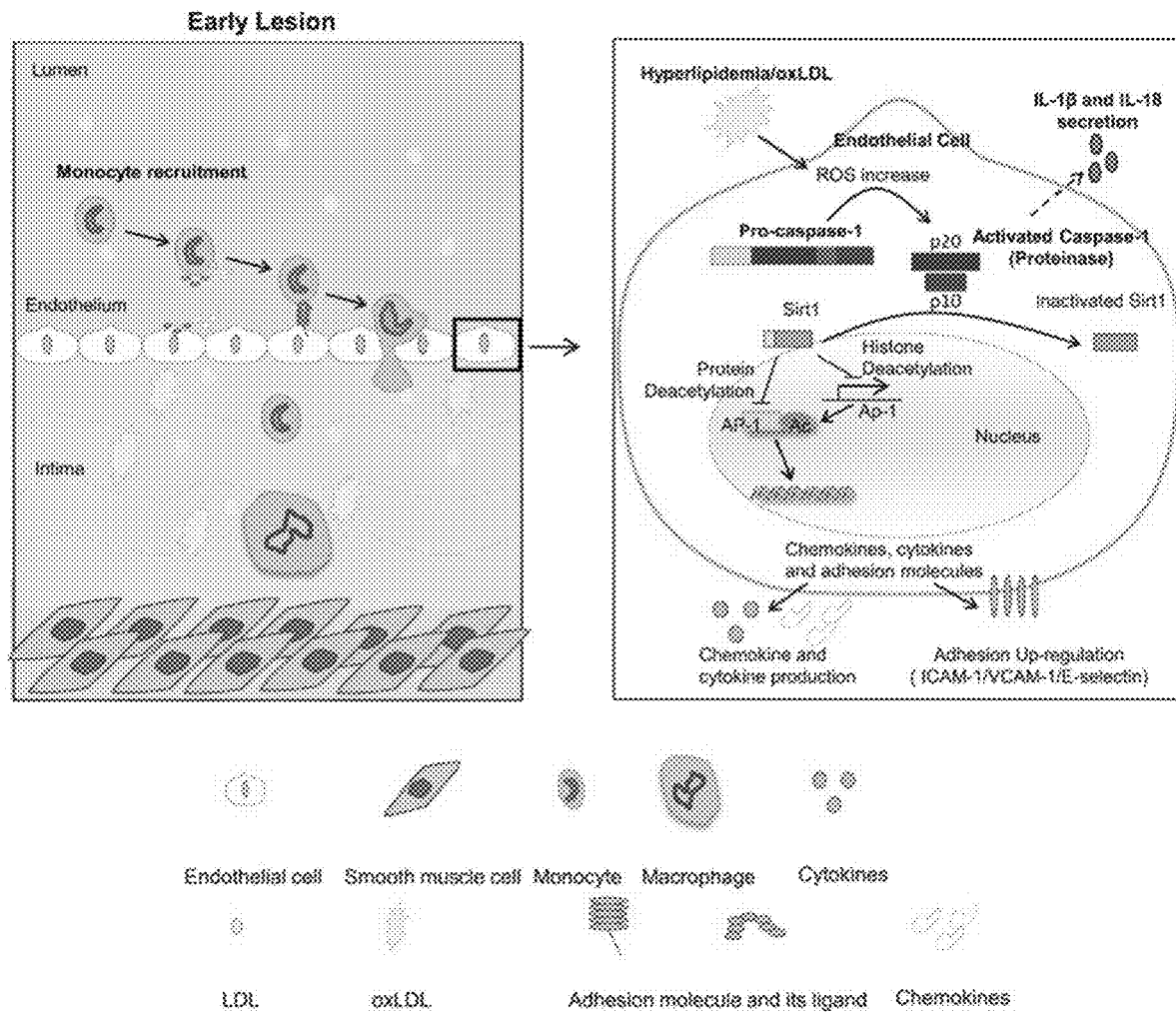
FIG. 13 depicts a schematic representation of a new model for the role of caspase-1 (casp-1) activation in endothelial cells (ECs) during early atherogenesis.

In our newly proposed working model, we summarize our findings and highlight current understanding (FIG. 13): (1) hyperlipidemia induces elevation of ROS via NADPH oxidase-dependent pathway; (2) increased ROS levels induce caspase-1 activation, EC inflammation, and endothelial pyroptosis (inflammatory cell death); (3) activated caspase-1 decreases anti-inflammatory protein/histone deacetylase Sirt1 expression by cleaving Sirt1; (4) Sirt1 is a high hierarchy gene that can deacetylate and inhibit proinflammatory transcription factors, including AP-1; and (5) the caspase-1-Sirt1-AP-1 pathway can promote endothelial activation, inflammation, and atherogenesis. Our results have demonstrated for the first time how hyperlipidemia, one of the most important metabolic risk factors, induces endothelial activation, which provides an important insight for future development of novel therapeutics for early intervention of cardiovascular diseases and other inflammatory diseases.

Example 2: Inhibition of Caspase-1 Activation in Endothelial Cells Improves Angiogenesis Deficient angiogenesis may contribute to worsen the prognosis of myocardial ischemia, peripheral arterial disease, ischemic stroke, etc. Dyslipidemic and inflammatory environments attenuate endothelial cell (EC) proliferation and angiogenesis, worsening the prognosis of ischemia.

Under these dyslipidemic and inflammatory environments, EC-caspase-1 becomes activated and induces inflammatory cell death that is defined as pyroptosis. However, the underlying mechanism that correlates caspase-1 activation with angiogenic impairment and the prognosis of ischemia remains poorly defined. By using flow cytometric analysis, enzyme and receptor inhibitors, and hind limb ischemia model in caspase-1 knock-out (KO) mice, we examined our novel hypothesis, i.e. inhibition of caspase-1 in ECs under dyslipidemic and inflammatory environments attenuates EC pyroptosis, improves EC survival mediated by vascular endothelial growth factor receptor 2 (VEGFR-2), angiogenesis, and the prognosis of ischemia. We have made the following findings. Proatherogenic lipids induce higher caspase-1 activation in larger sizes of human aortic endothelial cells (HAECs) than in smaller sizes of HAECs. Proatherogenic lipids increase pyroptosis significantly more in smaller sizes of HAECs than in larger sizes of the cells. VEGFR-2 inhibition increases caspase-1 activation in HAECs induced by lysophosphatidylcholine treatment. Caspase-1 activation inhibits VEGFR-2 expression. Caspase-1 inhibition improves the tube formation of lysophosphatidylcholine-treated HAECs. Finally, caspase-1 depletion improves angiogenesis and blood flow in mouse hind limb ischemic tissues. Our results have demonstrated for the first time that inhibition of proatherogenic caspase-1 activation in ECs improves angiogenesis and the prognosis of ischemia.

Our novel hypothesis in this study is that the inhibition of caspase-1 attenuates pyroptosis (inflammatory cell death) in ECs, improves EC survival mediated by VEGFR-2 signaling, angiogenesis, and ischemia's prognosis under dyslipidemic and inflammatory environments. To examine this hypothesis, we used the hind limb ischemia model in caspase-1 KO mice and stimulated HAECs with proatherogenic lipids, oxidized low density lipoprotein (oxLDL), carbamylated LDL, oxLDL-derived lipids, lysophosphatidylcholine (LPC), and lysophosphatidic acid (LPA) (Limbourg et al., 2009 Nat. Protoc. 4, 1737-1746). Our results showed that caspase-1 inhibition improves the tube formation of LPC-treated HAECs and that caspase-1 depletion improves angiogenesis and blood flow in mouse hind limb ischemic tissues. Our results have demonstrated for the first time that inhibition of proatherogenic caspase-1 activation in ECs improves angiogenesis and the prognosis of ischemia.

The materials and methods employed in this example are now described.

Reagents

The oxLDL and carbamylated LDL were purchased from Biomedical Technologies (Stoughton, Mass.). LPC and LPA were purchased from Avanti Polar Lipids (Alabaster, Ala.). Hydrogen peroxide ($H_2O_2$) was purchased from Sigma Vascular endothelial growth factor receptor II inhibitor (SU1498) was purchased from EMD Millipore (Billerica, Mass.).

Human Aortic Endothelial Cell Culture

Human aortic endothelial cells (HAECs) were purchased at Clonetics Corp. (San Diego). The cells were cultured in a 2% gelatin-coated 75-cm$^2$ flask in M199 (Hyclone Labs., Logan, Utah) with 20% fetal bovine serum (FBS), 1% penicillin/streptomycin (Invitrogen), 3 ng/ml EC growth supplement (BD Biosciences), and 5 units/ml heparin (Sigma) at 37° C. under 5% $CO_2$, 95% air until passage 8. For experiments, HAECs (≤passage 9) were used and treated with the desired stimuli for the indicated time.

Caspase-1 Activity Assay

Active caspase-1 levels were determined with an APO LOGIX kit (Cell Technology, Mountain View, Calif.). The kit contained a carboxyfluorescein (FAM) (excitation/emission (nm): 490/520)-labeled peptide fluoromethyl ketone (FMK) caspase-1 inhibitor (FAM-YVAD-FMK), which irreversibly binds to active caspase-1. The procedures were performed according to the manufacturer's instructions. HAECs were cultured in 6-well dishes and serum-starved overnight to ensure quiescence of the cells before treatment. The next day, HAECs were treated with the indicated stimuli for 6 h. Cells were harvested and suspended at 1×10$^6$ cells/ml. The cell suspension (150 µl) was incubated in 37° C. with 1× FAM-YVAD-FMK for 1 h. After being washed with 1× washing buffer, the cells were fixed with fixative buffer and stored in 4° C. for up to 24 h. To determine the cell membrane integrity, the unfixed cells were stained with 7-AAD (Pharmingen) (0.25 µg/test) and incubated for no more than 10 min before analysis.

Flow Cytometer

The FACSCalibur flow cytometer (BD Biosciences) was used to determine FAM$^+$ staining (caspase-1 activity marker, FL-1 channel), 7-AAD$^+$ staining (cell membrane integrity marker, FL-4 channel), and ICAM-1 staining (adhesion molecule marker, FL-4 channel).

Data Analysis Using FlowJo Software

All flow cytometric data were analyzed by using the FlowJo software (Tree Star, Ashland, Oreg.). The uncompensated data were collected from the flow cytometer (either FACSCalibur flow cytometer or LSRII flow cytometer; BD Biosciences). Forward and side scatter gates were used to select live cell populations from clumps and debris. The positive gating was determined by its matched IgG control, and single staining was used to determine the compensation parameter. Different gates were established to analyze the data according to cell size as described in our figures.

Mice

Wild-type mice were obtained from The Jackson Laboratory (Bar Harbor, Me.). Caspase-1$^{-/-}$ (Casp-1$^{-/-}$) mice in a C57BL/6J background were obtained. Mice were housed in a specific pathogen-free environment. Mice were maintained on a normal chow diet (5% fat, Lab diet 5001).

Murine Hind Limb Ischemia Model

Age-matched 8-week-old male mice were used to create the mouse model of hind limb ischemia as reported previously (Limbourg et al., 2009 Nat. Protoc. 4, 1737-1746). An incision was made in the skin at the mid-portion of the right hind limb. The femoral artery and vein were then dissected free from nerve. Proximal and distal portions of the femoral artery were ligated followed by complete excision from the hind limb.

Laser Doppler Perfusion Imaging

Blood perfusion in the hind limb was monitored by using laser Doppler perfusion imaging (Lisca, North Brunswick, N.J.). The mice were anesthetized before initiating the image scanning. For each time point, the laser Doppler image obtained was analyzed by averaging the perfusion and expressed as the relative unit of flux, as determined by Moor Instruments, over the surface of the ischemic and nonischemic foot.

Tube Formation Assay

The Matrigel matrix (Bedford, Mass.) was used to coat the 96-well plates. Human aortic endothelial cells were cultured. The cells were treated with caspase-1 inhibitor (Anaspec, Fremont, Calif.) and proatherogenic stimulus LPC for 24 h. HAECs were harvested and suspended. Cell concentration was determined and added to each Matrigel-coated well and incubated for 16-18 h. Images were collected using the inverted microscope.

Data Analysis

The experiments were performed at least three times, and results were expressed as the means±S.E. Statistical comparison of single parameters between two groups was performed by paired Student's t test, and multiple group comparisons were performed by one-way analysis of variance. Data were considered statistically significant if p was <0.05.

The results of the experiments are now described.

Figures 14A, 14B, 14C:
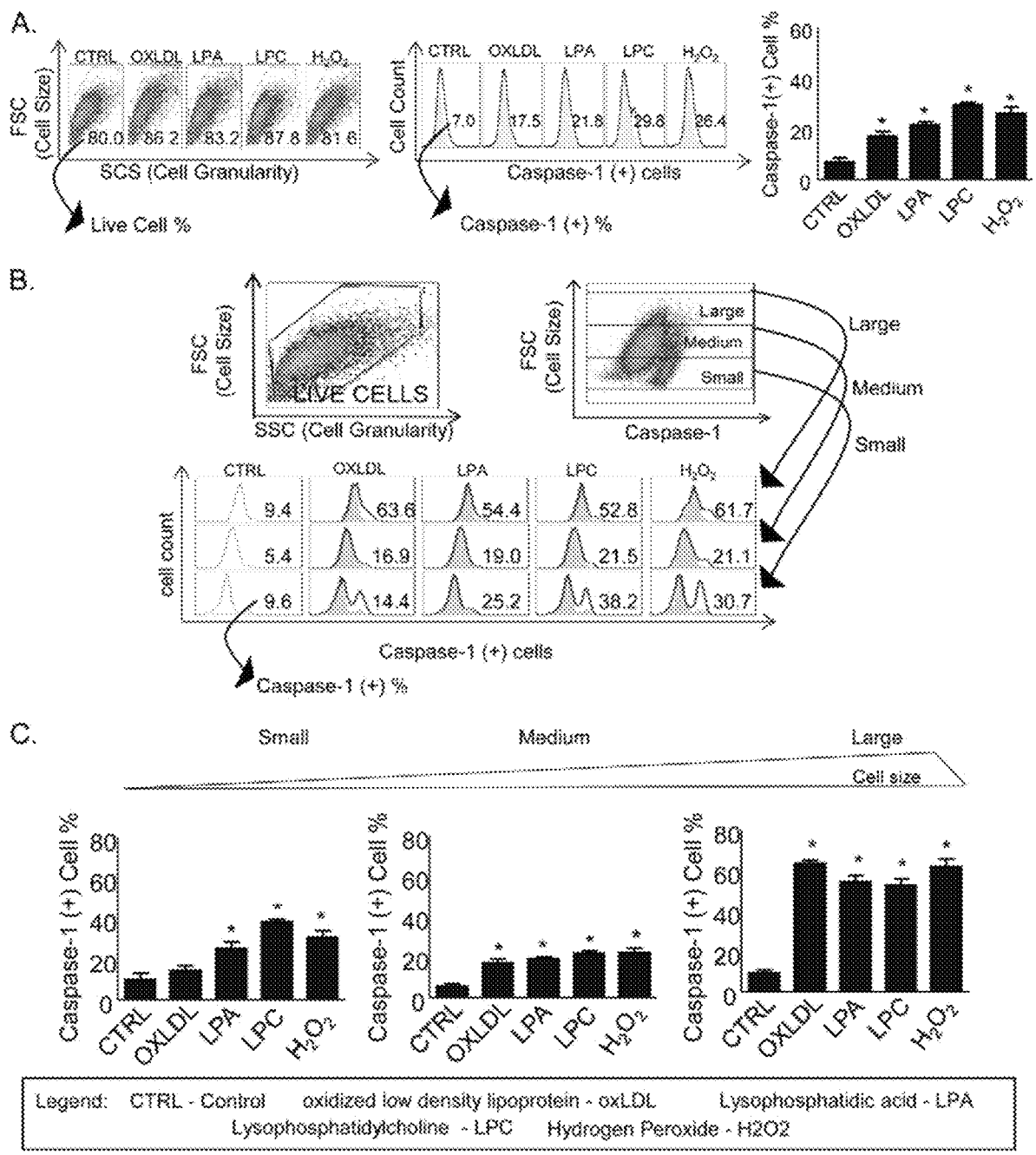
FIG. 14A through FIG. 14C, depicts experimental results showing proatherogenic oxidized lipids induce higher caspase-1 activation in the larger sizes of HAECs than in smaller sizes of HAECs.

Proatherogenic Oxidized Lipids Induce Higher Caspase-1 Activation in the Larger Sizes of HAECs than in Smaller Sizes of HAECs To examine our hypothesis that the size and growth status of endothelial cells regulate caspase-1 activation induced by proatherogenic lipids, we performed the stimulation of HAECs followed by flow cytometric analysis, and we determined the caspase-1 activation in the five groups of HAECs, including untreated control, oxLDL-treated, LPA-treated, LPC-treated, and $H_2O_2$-treated control. The results showed that proatherogenic lipids significantly activate caspase-1 (FIG. 14A). To determine whether caspase-1 is activated differently in various cell sizes of HAECs in response to proatherogenic lipid stimulation, we used the forward scatter (FSC) function in the y axis to establish the cell size and caspase-1 activation in the x axis to determine the activation of HAECs during the analysis of the FACS data using the FlowJo software. The results in the dot plot (FIG. 14B, upper panel) showed that caspase-1-positive population spreads in a slightly diagonal manner along the forward scatter (y axis) and caspase-1 activity (x axis), suggesting a possibility that larger sizes of cells have higher caspase-1 activity than smaller sizes of HAECs. After gating out HAECs into three populations, large, medium, and small using FSC in the y axis, we examined caspase-1 activation in the x axis in these three cell size populations as we described previously. The results showed that oxLDL, LPA, and LPC induce caspase-1 activation in a larger size of HAECs by 63.6, 54.4, and 52.8%, respectively, higher than that in the smaller size of HAECs (14.4, 25.2, and 38.2%) (FIGS. 14, B and C), suggesting that caspase-1 activation is associated with high cell growth status in larger cell sizes and that various lipid stimuli show no significant differences in activating caspase-1 in various sizes of HAECs. Here, we found the new results on the effects of other proatherogenic lipids in promoting caspase-1 activation. Taken together, the results demonstrated that proatherogenic lipids induce caspase-1 activation in HAECs, which may promote EC activation in a larger size of cells and inflammatory cell death in a smaller size of cells.

Figure 15:
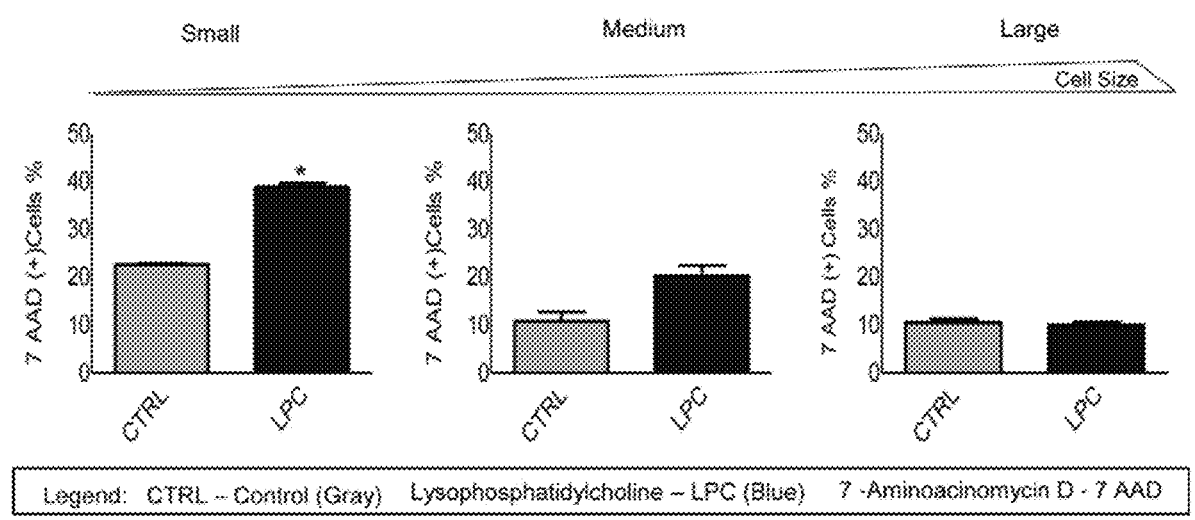
FIG. 15 depicts experimental results showing proatherogenic stimuli significantly Proatherogenic oxidized lipids induce higher caspase-1 activation in the larger sizes of HAECs than in smaller sizes of HAECs. HAECs were treated with different proatherogenic stimuli as follows: oxLDL (100 µM), LPA (30 µM), LPC (30 µM), and $H_2O_2$ (500 µM) for 6 h. Caspase-1(+) cell percentage was measured, and the results showed an increase in caspase-1 activation after proatherogenic lipid treatments. Three different sizes of cell populations after caspase-1 activation were identified using FSC, which is widely used to define the cell size in flow cytometry. The gates were established as small, medium, and large according to the cell size (FSC, y axis) and caspase-1 activation (x axis) to analyze the differential caspase-1 activation percentage according to the cell size. Analysis of three gates showed an increase in caspase-1 activation percentage in larger HAECs. C *, $p<0.05$. increase more pyroptosis in smaller sizes of HAECs than in larger sizes of the cells. The pyroptotic rates in LPC-treated caspase-1(+) HAECs were increased as the cell sizes became smaller. The FACS results demonstrated an increase in 7AAD$^+$ pyroptotic percentage in smaller sizes of caspase-1(+) HAECs when compared with medium size and larger size caspase-1(+) cells. The bar graphs show the quantitation data of 7AAD$^+$ percentages in caspase-1(+) cells. *, $p<0.05$.

Proatherogenic Lipids Significantly Increase Pyroptosis in Smaller Sizes of Human Aortic Endothelial Cells than in Larger Sizes of the Cells Inflammatory cell death (pyroptosis) is a newly characterized form of cell death with the features of caspase-1 activation, plasma membrane rupture, and release of inflammatory factors (Miao et al., 2010 Nat. Immunol. 11, 1136-1142). In FIGS. 14, B and C, we noticed that caspase-1 activities in LPC-treated HAECs and $H_2O_2$-treated positive control HAECs are lower in the medium sizes of HAECs than in the smaller sizes of cells, suggesting that increased caspase-1 activities in the smaller sizes of cells result in poorer survival and decreased sizes of cells. To examine the hypothesis that proatherogenic lipids promote caspase-1 activation and promote higher EC pyroptosis in the smaller size of HAECs compared with the larger size of HAECs, we stimulated HAECs with LPC and co-stained them with the caspase-1 fluorescence probe to analyze the activation of caspase-1 and the viable fluorescence dye 7-AAD to determine the plasma membrane integrity, viability, and pyroptosis. We first analyzed the activation of caspase-1 in HAECs, and we established the y axis as FSC, which evaluates the cell size, and the x axis to measure the activation of caspase-1. Using these parameters, we analyzed caspase-1 activation in three sizes of cell populations. After that, we analyzed the 7-AAD staining that determines HAEC pyroptosis in different sizes of caspase-1(+) HAECs. The results showed that in LPC-treated HAECs, the smaller size of caspase-1(+) cells has an increase in pyroptosis (38.77%) compared with that in medium size (20.17%) and that in the large size of caspase-1(+) HAECs (9.93%). The bar graphs results in FIG. 15 showed that LPC stimulation significantly induced 7-AAD$^+$ pyroptosis from 22.50 to 38.77% in smaller size of caspase-1(+) HAECs (p<0.01). However, LPC stimulation did not induce significant pyroptosis in the medium and larger size of caspase-1(+) HAECs from 10 to 12% (p>0.05). It should be noted that in unstimulated cells, the percentage of 7-AAD$^+$ cells in the smaller sizes of HAECs (22.50%) was much higher than that in both the medium size (10.71%) and larger size of HAECs (10.49%), suggesting that the membrane integrity in the medium and larger sizes of caspase-1(+) HAECs is significantly better preserved than that of the smaller sizes of caspase-1(+) HAECs. The results demonstrated that caspase-1 activation induced by LPC in the larger sizes of HAECs may promote EC activation but not significant pyroptosis and that as HAECs become smaller in size, LPC-induced caspase-1 activation promotes measurable pyroptosis.

Figures 16A, 16B:
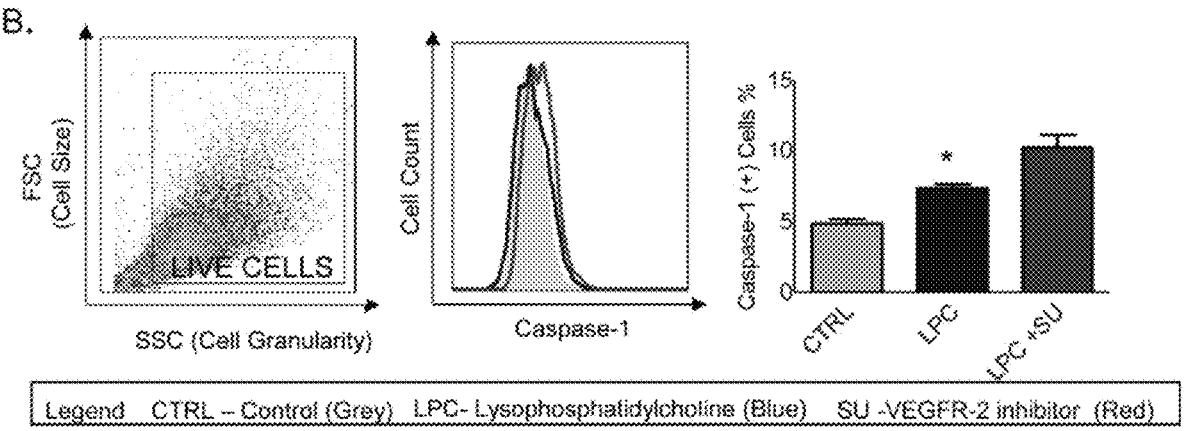
FIG. 16A and FIG. 16B, depicts experimental results showing caspase-1 activation is increased after the inhibition of VEGFR-2 in LPC-treated HAECs.

VEGFR-2 Inhibition Increases Caspase-1 Activation in HAECs Induced with LPC Treatment Our data suggest that as cell growth status improves, endothelial cell size becomes larger and less pyroptotic than smaller cell sizes. These results lead us to hypothesize that vascular endothelial growth factor signaling may inhibit caspase-1 activation and pyroptosis. To examine this possibility, we searched for supporting evidence with unpublished microarray data deposited in the National Institutes of Health NCBI-Geo-Profile database. The experimental data of a microarray analysis with vegfr2 gene knockdown (KD) samples, compared with wild-type control samples in two different time courses (84 and 95 h after gene knockdown), showed that the expressions of caspase-1 and inflammasome component apoptosis-associated speck-like protein containing a caspase recruitment domain (ASC) were increased at a ratio of 1.48 and 2.45, respectively (p=0.00014–0.06443) (FIG. 16A). The expression of two caspase-1 substrates, such as IL-1β and IL-18, and two housekeeping genes was not significantly changed. To further consolidate the conclusion, we then stimulated HAECs with LPC in the presence or absence of the VEGFR-2 inhibitor SU1498, followed by co-stained HAECs with a caspase-1 activity probe. The results showed that VEGFR-2 inhibition increases caspase-1 activation in HAECs (FIG. 16B). These results suggest that VEGFR-2 cell growth signaling inhibits caspase-1 activation and cell death.

Caspase-1 Activation Inhibits VEGFR-2 Expression

As indicated above, our results give rise to the following question. How can caspase-1 promote HAEC activation in larger cell sizes and simultaneously enhance pyroptosis in the smaller size of HAECs? One possibility is that caspase-1 activation and VEGFR-2 signaling interplay each other in their functions. To examine this possibility, we analyzed the National Institutes of Health NCBI-Geo-Profile database. The experimental data of a microarray analysis showed that the ratio of VEGFR-2 expression levels in the wild-type control samples versus caspase-1 gene-deficient (KO) samples was 0.62 (FIG. 17A), suggesting that VEGFR-2 expression is increased in caspase-1 gene depletion samples and that caspase-1 activation inhibits VEGFR-2 signaling. The caspase-1 expression level was 22.23-fold higher in wild-type samples than in caspase-1 KO samples, justifying the bona fide comparison of wild-type samples and caspase-1 KO samples.

In addition, the expression levels of three housekeeping genes were within the range of 1.04 to 0.99, suggesting the high quality of the microarray experimental datasets. To gain further support for our conclusion, we then stimulated HAECs with LPC in the presence or absence of caspase-1 inhibitor followed by the analysis of the FACS data, which showed that after the inhibition of caspase-1 in LPC-treated HAECs, VEGFR-2 expression was increased (FIG. 17B). We further determined the expression of VEGFR-2 after caspase-1 inhibition in LPC-treated HAECs in different cell sizes. Three gates were established according to the cell size using FSC in the y axis to analyze the cell sizes and VEGFR-2 expression in the x axis. The results showed that pretreatment with caspase-1 inhibitor in LPC-treated HAECs increased the expression of VEGFR-2 when compared with LPC-treated HAECs from 11.3 to 22.1% in the smaller size of HAECs, from 22.1 to 50.0% in the medium size of HAECs, and from 34.3 to 64.4% in the larger size of HAECs (FIGS. 17, C and D). It has been demonstrated in our recent report that caspase-1 deficiency in apolipoprotein E (apoE)−/−/caspase-1−/− mouse aorta and the inhibition of caspase-1 in ECs result in accumulation of anti-inflammatory protein/histone deacetylase sirtuin 1 (Sirt1), which is a proteolytic substrate of caspase-1, suggesting that caspase-1 activation in early atherogenesis promotes endothelial activation via a Sirt1 degradation pathway. To determine whether activation of Sirt1 has the same effect as inhibition of caspase-1 in promoting VEGFR-2 expression, we performed the same experiment as previous ones using Sirt1 activator pretreatment in LPC-treated HAECs. We used the same method to analyze the data according to cell sizes and VEGFR-2 expression. The VEGFR-2 expression was increased in LPC-treated HAECs pretreated with Sirt-1 activator compared with LPC-treated HAECs. The VEGFR-2 expression in the above-mentioned groups increased from 11.3 to 21.0% in the smaller size of HAECs, from 22.1 to 52.5% in the medium size of HAECs, and from 34.3 to 70.2% in the larger size of HAECs. Taken together, the results suggest that LPC-induced caspase-1 activation decreases VEGFR-2 expression levels in HAECs, whereas the inhibition of caspase-1 and activation of Sirt-1 rescue VEGFR-2 expression levels in LPC-treated HAECs.

Figures 18A, 18B:
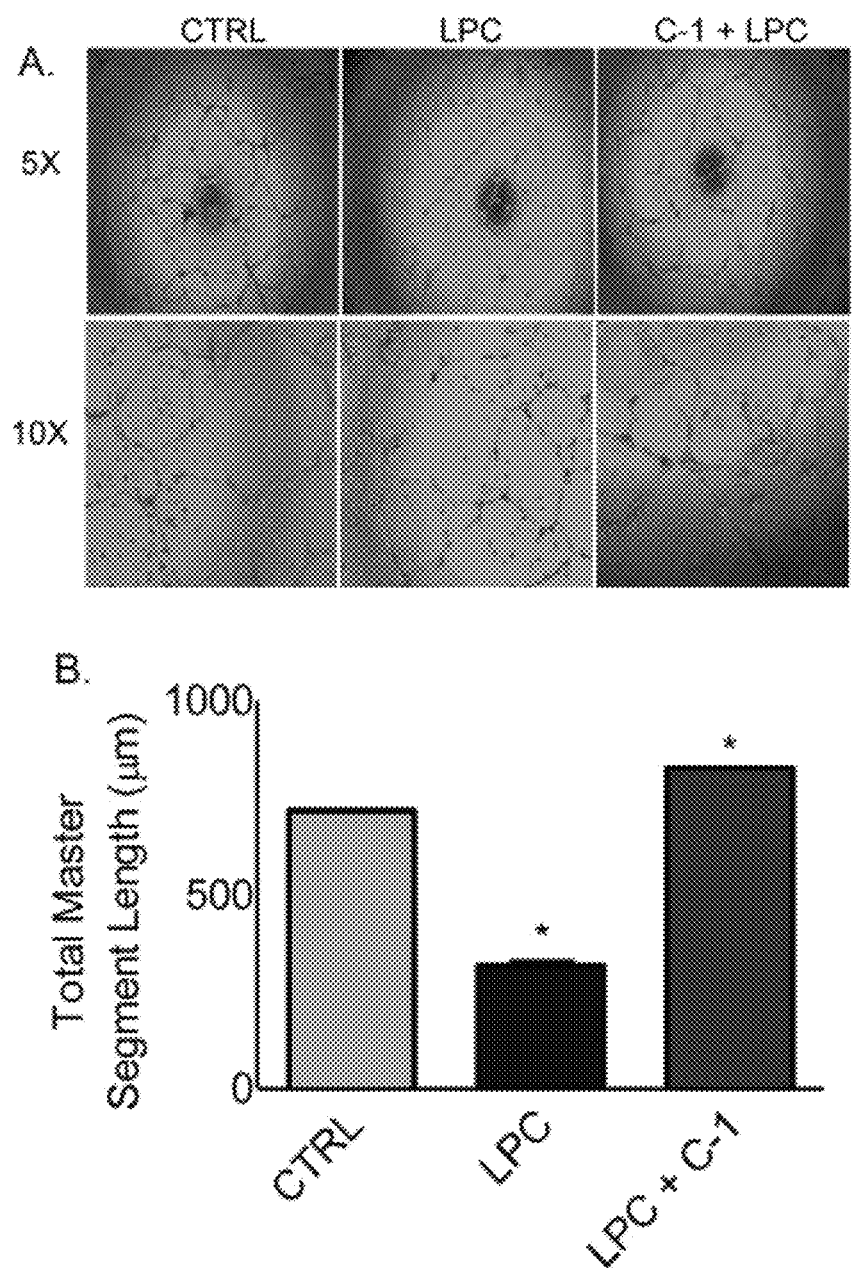
FIG. 18A and FIG. 18B, depicts experimental results showing tube formation, as an in vitro model of angiogenesis, is improved after caspase-1 inhibition in LPC-treated cells.

Caspase-1 Inhibition Improves Tube Formation of LPC-Treated Human Aortic Endothelial Cells Because EC tube formation assay has been widely used in determining VEGFR-2-mediated angiogenesis (27), we used the EC tube formation assay in the Matrigel to test the hypothesis that caspase-1 inhibition improves VEGFR-2-mediated HAEC tube formation. To test this hypothesis, we performed tube formation assays with untreated HAECs, LPC-treated HAECs, and LPC plus caspase-1 inhibitor co-treated HAECs. The results showed that the lengths of the total master segment length (in micrometers) of tube formation in LPC-treated HAECs were significantly lower (317 μm) than in untreated HAEC controls (718 μm). In addition, LPC plus caspase-1 inhibitor co-treated HAECs have restored the EC tube formation (827 μm) (FIG. 18). The results suggest that caspase-1 inhibition not only increases VEGFR-2 expression levels but also functionally improves VEGFR-2-mediated EC tube formation.

Figures 19A, 19B, 19C:
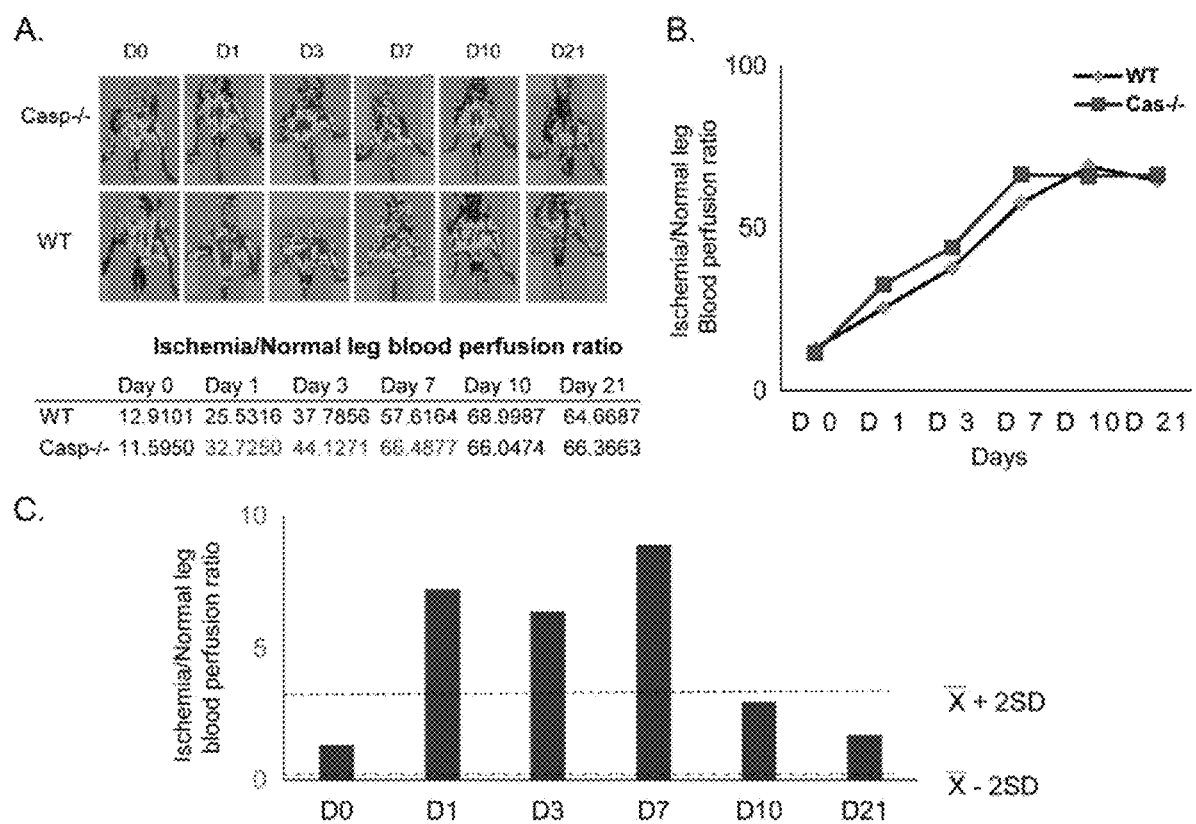
FIG. 19A through FIG. 19C, depicts experimental results showing caspase-1 KO mice have an increase in blood flow after hind limb ischemia compared with wild-type mice.

Caspase-1 Depletion Improves Angiogenesis and Ischemia/Normal Blood Perfusion Ratio in Hind Limb Ischemic Mouse Tissues Because the mouse model of hind limb ischemia has been widely used in determining the gene effect on hind limb ischemia-triggered angiogenesis (25), we performed the hind limb ischemia model on wild-type mice and caspase-1 KO mice followed by the blood flow measurement with the LDSII Doppler at days 0-3, 7, 10, and 21. The results showed that caspase-1 depletion increased the ischemia/normal leg blood perfusion ratios from 25.5 to 32.7% on day 1, from 37.8 to 44.1% on day 3, and from 57.62 to 66.49% on day 7, respectively, in hind limb ischemia-affected tissues in caspase-1 KO mice in comparison with that in wild-type mice at the same time points ($p > \bar{X} \pm 2SD$) (FIG. 19). The results suggest that caspase-1 depletion improves angiogenesis and blood supply in hind limb ischemic mouse tissues.

A Novel Therapeutic for Ischemia

Our results have addressed the issue about the mechanism in the interplay between inflammatory environment, initiation of EC activation, inflammatory cell death (pyroptosis) in ECs, angiogenesis impairment in ECs, and ischemia in animal tissue. We examined caspase-1 activation in ECs, EC pyroptosis, the microarray data, EC tube formation, and hind limb ischemia mouse model, and we investigated our novel hypothesis that the inhibition of caspase-1 in ECs attenuates EC pyroptosis, improves VEGFR-2-mediated ECs survival, angiogenesis, and ischemia's prognosis under inflammatory and dyslipidemic environment. We have made the important finding that dyslipidemic environment induces higher caspase-1 activation in the larger sizes of HAECs than in smaller sizes of HAECs. Moreover, the smaller HAECs have higher pyroptosis rates than larger HAECs after stimulation with proatherogenic lipids. The activation of caspase-1 after stimulation with proatherogenic lipids promotes ECs activation as judged by increased intercellular adhesion molecule-1 expression in HAECs as demonstrated elsewhere herein. Our results show that the inhibition of VEGFR-2 increases caspase-1 activation in HAECs induced by LPC treatment and that the activation of caspase-1 inhibits VEGFR-2 expression in HAECs. The molecular data were further consolidated with the evidence in functional angiogenesis models that caspase-1 inhibition improves tube formation of LPC-treated HAECs and the depletion of caspase-1 improves angiogenesis and blood supply in the hind limb of ischemic mouse tissues.

Although microvascular endothelial cells are often involved in angiogenesis, aortic endothelial cells are also used as experimental models for angiogenesis such as the aortic ring angiogenesis model (Blacher et al., 2001 Angiogenesis 4, 133-142). In addition, neovessel formation was recently found in the human thoracic aneurysm of the ascending aorta (Kessler et al., 2014 Cardiovasc. Res. 104, 147-159) and revascularization in atherosclerotic aorta (Luttun et al., 2002 Nat. Med. 8, 831-840). The use of aortic endothelial cells in the commonly used experimental angiogenesis model and the involvement of aortic endothelial cells in pathological angiogenesis and atherosclerosis justified our use of aortic endothelial cells in this study.

Our recent review summarized that there are 11 endogenous metabolic stress-related danger signals, including oxLDL and cholesterol crystals that induce caspase-1 activation (Yin et al., 2013 Front. Biosci. 18, 638-649). However, the issue of whether several oxLDL-derived lipids, such as LPC and LPA (Zhou et al., 2011 Cell Metab. 13, 592-600), can induce caspase-1 activation was not clear. Our results reported here have demonstrated for the first time that LPC and LPA, small non-crystal lipids, can induce caspase-1 activation, presumably not via particle-lysosome pathway (Yin et al., 2013 Front. Biosci. 18, 638-649). Because LPA acts on the LPC receptors, including LPA1-6 G protein-coupled receptors (Haas et al., 1997 Microvasc. Res. 53, 113-120), and LPC acts on the LPC receptor, GPCR-G2A (Schmitz et al., 2010 Atherosclerosis 208, 10-18), the signals from these receptors to activate caspase-1 have been intensely studied in our investigation.

It was reported that lipopolysaccharide induces a caspase-3/caspase-1-dependent EC apoptosis, which can be inhibited by VEGF (Munshi et al., 2002 J. Immunol. 168, 5860-5866). However, we showed for the first time that VEGFR-2 signaling inhibits caspase-1-dependent pyroptosis, which is demonstrated by positive 7-AAD staining. Of note, 7-AAD staining is not a feature of apoptosis (Miao et al., 2010 Nat. Immunol. 11, 1136-1142). In addition, the detailed molecular mechanisms underlying caspase-1 inhibition of VEGFR-2 transcript expression remain unknown. It was reported that caspase-1 generated proatherogenic cytokine IL-1β, which counteracts mechanical signals that induced VEGFR-2 signaling and inhibits EC proliferation (Liu et al., 2010 J. Immunol. 185, 1215-1221). Our results showed that caspase-1 has an IL-1β, IL-18, and sirtuin 1-independent transcription regulatory effect.

Figure 20:
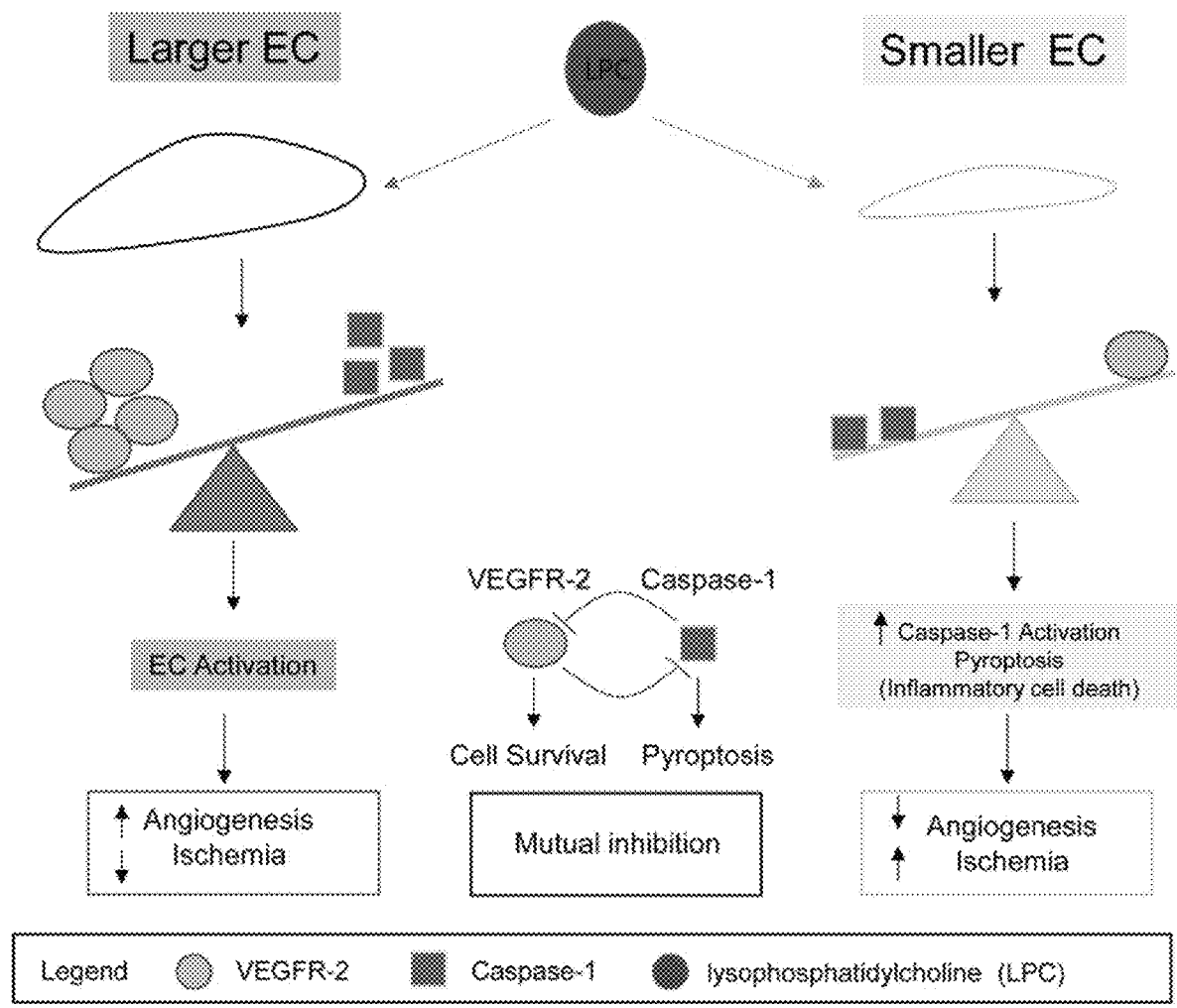
FIG. 20 depicts a schematic representation of the working model. The larger HAECs have higher vascular endothelial growth factor receptor 2 (VEGFR-2) and less caspase-1(+) pyroptosis induction after dyslipidemic stimuli, which promotes angiogenesis and improves ischemia's prognosis. However, after dyslipidemic stimuli, the smaller HAECs have an increase in caspase-1(+) induction of pyroptosis and less VEGFR-2 expression, which decrease the angiogenesis and worsen ischemia's prognosis. In summary, there is a mutual inhibition between the VEGFR-2 signaling pathway and caspase-1 activation in endothelial cells.

In our newly proposed working model (FIG. 20), we summarize our findings and highlight the current understanding that the larger size of HAECs has higher VEGFR-2 expression and less caspase-1(+) induction of pyroptosis than the smaller cells under the dyslipidemic and inflammatory environment, which promotes cell survival and angiogenesis and improves the prognosis of the ischemia. In contrast, under dyslipidemic and inflammatory environments, the smaller size of HAECs has an increase in caspase-1(+) induction of pyroptosis and less VEGFR-2 expression than the larger cells that decrease the angiogenesis and cell survival and worsen ischemia's prognosis. In summary, there is a mutual inhibition between the VEGFR-2 signaling pathway and caspase-1 activation in endothelial cells. Our novel results provide important insight on the future development of a novel therapeutic approach, based on the inhibition of caspase-1 for suppression of vascular inflammation and improvement of angiogenesis and ischemia prognosis under inflammatory environments (Annex et al., 2013 Nat. Rev. Cardiol. 10, 387-396).

Example 3: Caspase-1 Mediates Hyperlipidemia-Weakened Progenitor Cell Vessel Repair Caspase-1 activation senses metabolic danger-associated molecular patterns (DAMPs) and mediates the initiation of inflammation in endothelial cells. Here, we examined whether the caspase-1 pathway is responsible for sensing hyperlipidemia as a DAMP in bone marrow (BM)-derived Stem cell antigen-1 positive (Sca-1$^+$) stem/progenitor cells and weakening their angiogenic ability. Using biochemical methods, gene knockout, cell therapy and myocardial infarction (MI) models, we had the following findings: 1) Hyperlipidemia induces caspase-1 activity in mouse Sca-1$^+$ progenitor cells in vivo; 2) Caspase-1 contributes to hyperlipidemia-induced modulation of vascular cell death-related gene expression in vivo; 3) Injection of Sca-1$^+$ progenitor cells from caspase-1$^{-/-}$ mice improves endothelial capillary density in heart and decreases cardiomyocyte death in a mouse model of MI; and 4) Caspase-1$^{-/-}$ Sca-1$^+$ progenitor cell therapy improves mouse cardiac function after MI. Our results provide insight on how hyperlipidemia activates caspase-1 in Sca-1$^+$ progenitor cells, which subsequently weakens Sca-1$^+$ progenitor cell repair of vasculature injury. These results demonstrate the therapeutic potential of caspase-1 inhibition in improving progenitor cell therapy for MI.

In this study, we examined the hypothesis that the caspase-1 pathway in BM-derived Sca-1+ progenitor cells can sense dyslipidemia and that caspase-1 activation in Sca-1+ progenitor cell impairs their angiogenic ability during ischemic injury. To examine this hypothesis, we examined caspase-1 activity in mouse Sca-1+ progenitor cells in atherogenic apolipoprotein E deficient (ApoE−/−) mice after high fat (HF) diet feeding in vivo. We also performed cDNA microarray analysis to determine the downstream effects of hyperlipidemia-induced caspase-1 activation in vivo. In addition, we utilized a mouse model of myocardial infarction (MI) to determine whether caspase-1 gene depletion could enhance the therapeutic efficacy of progenitor cell therapy in ischemic myocardium. Our results demonstrate that caspase-1 activation is responsible for hyperlipidemia-induced vascular dysfunction by impairing vessel repair of Sca-1+ progenitor cells.

The material and methods employed in these experiments are now described.

Reagents

EGM-2 Medium was purchased from Lonza corporation (CC-3202). Histopaque®-1083 was from Sigma-Aldrich (10831). FAM-YVAD-FMK caspase-1 detection kit was from Cell Technology (FAM600-2). Anti-APC MultiSort kit and MicroBeads were from MACS (130-091-255/130-048-801). Rat IgG2a K Isotype control APC was from eBioscience (17-4321-81). Biotinylated Griffonia simplicifolia lectin I (isolectin B4) from Vector (B-1205), Biotin-XX conjugate was from Invitrogen (I21414). APC anti-mouse Ly-6A/E (Sca-1) antibody were from Biolegend (121906/108112). All other reagents were purchased from Sigma-Aldrich (St. Louis, Mo.).

Mice and Diets

All mice were in a C57B/L6 strain background. Wild-type (WT) and ApoE−/− mice were purchased from the Jackson Laboratories (Bar Harbor, Me.). Caspase 1−/− mice were obtained (17). ApoE/caspase-1 double gene deficient (ApoE−/−/caspase-1−/−) mice were generated by crossing caspase-1−/− mice into ApoE−/− mice as we reported (4). Male mice were fed either standard rodent chow diet (catalog #8640; Harlan Teklad, Madison, Wis.) or HF diet (catalog #88137, Harlan Teklad) starting from 8 weeks to induce dietary dyslipidemia as we reported (4).

Transcriptome Microarray Analysis

Total RNA was extracted from the aortas of mice using the RNeasy Kit (Qiagen, Valencia, Calif.). RNA quantity was determined by the NanoDrop ND-2000 (Thermo Scientific, Wilmington, Del.). The RNA integrity was determined by the RNA 28S/18S ratio using the Agilent 2100 Bioanalyzer (Agilent Technologies, Santa Clara, Calif.). Then samples were labeled and hybridized to the Affymetrix Genechip Mouse Gene 2.0.ST Arrays (Santa Clara, Calif.) following the manufacturer's instructions. Scanned microarray images were analyzed using the Affymetrix Gene Expression Console with Robust Multiarray Average normalization algorithm.

Microarray Data Analysis

Our affymetrix data analysis was done in the R statistical environment using "oligo" and "limma" packages. Venn diagram analysis was performed in the R statistical environment using the package "VennDiagram". Heat map and scatter plot were performed using the statistical tools provided by the R and Bioconductor projects.

Ingenuity Pathway Analysis

In order to categorize clinical functions and molecular and cellular functions related to the identified genes in our microarray analysis, the Ingenuity Pathway Analysis (IPA, Ingenuity Systems) was used. The differentially expressed genes were identified and uploaded into IPA for analysis. The IPA Tox analysis was used for clinical pathology functions and the Core analysis was used for molecular and cellular pathways.

Flow Cytometry Analysis of Sca-1+ Cells

After mouse BM was harvested from the femurs and tibiae, the collected cells were added with ACK buffer to lysis red blood cells and homogenized into a single cell suspension afterwards by mixing and filtering through a 70 micron filter. After centrifugation, cells were washed and resuspended in EGM-2 medium. Active caspase-1 levels were determined with APO LOGIX kit (Cell Tech., Mountain View, Calif.). The kit contains a carboxyfluorescein (FAM)(Excitation/Emission (nm):490/520)-labeled peptide fluoromethyl ketone (FMK) caspase-1 inhibitor (FAMY-VADFMK), which enters the cell and irreversibly binds to activated caspase-1 but not pro-caspase-1. All procedures were performed according to the manufacturer's instruction. Briefly, cell suspension were incubated at 37° C. with 1× FAM-YVAD-FMK for 1 hour and then washed with 1× washing buffer. For the cell surface marker Sca-1 staining, cells were incubated for 30 minutes with monoclonal antibody against mouse Sca-1 or isotype control. Cells were washed afterwards and fixed in 2% paraformaldehyde before flow cytometry analysis. The data were analyzed by LSR II flow cytometer (BD Biosciences, San Jose, Calif.) and the FlowJo software (Tree Star, Ashland, Oreg.).

Magnetic Cell Sorting and Cell Trace of Sca-1+ Cells

BM-derived mononuclear cells were isolated from the BM of WT mice or caspase-1-/- mice by density gradient using Histopaque-1083. Sca-1+ cells were purified by an autoMACS separator (Miltenyi Biotec), using magnetic beads-coated mouse APC anti-mouse Ly-6A/E (Sca-1) antibody and an Anti-APC MultiSort Kit according to the manufacturer's instructions. To evaluate the homing of injected cells to infarcted heart, purified Sca-1+ cells were labeled with CellVueR NIR (near infrared) 780 (Excitation max: 745 nm/Emission max: 776 nm, Mol. Targeting Tech. Inc. West Chester, Pa.) and injected peri-orbitally into C57/B6 mice, 6 hours before MI procedure. Images for tracing CellVueR NIR-labelled Sca-1+ cells were performed using the Multispectral FX Pro (Fixed Lens) Image Station (Carestream Health, Woodbridge, Conn.) for near-infrared fluorescence (NIRF) signals both prior to and at 0, 21, 24 and 45 hours post-CellVueR and post-PSVue injection.

Experimental MI and Cell Therapy

Experiments were performed in 14-16 weeks old male WT mice fed a HF diet for 6 weeks. Acute MI was induced by permanent left anterior descending coronary artery ligation as previously described (Gao et al., 2010, Circ Res, 107(12), 1445-53). Briefly, mice were anesthetized with 2% isoflurane. A skin incision was made over the left thorax, and the pectoral muscles were retracted to expose the ribs. At the level of the fourth intercostal space, the heart was exposed and pumped out through an expanded space between ribs. After a permanent knot was made around the left anterior descending coronary artery (LAD) at 2-3 mm from its origin with 6-0 silk suture, the heart was immediately placed back into the intrathoracic space, followed by manual evacuation of pneumothoraces and closure of the incision. Sham-operated animals were subjected to the same surgical procedures except that the suture was passed under the LAD but was not tied. After full recovery from cardiac surgery (four hours after MI), animals were randomized into two cell therapy groups. Purified Sca-1+ cells were injected peri-orbitally into those mice.

Measurement of Cardiac Function

Mouse cardiac function was measured with echocardiography (ECHO). ECHO was performed with VisualSonics Velvo 770 high-resolution in vivo microimaging system (FUJIFILM VisualSonics, Toronto, Canada). Mice were anesthetized with 2% isoflurane initially and then 1% during the ECHO procedure. Hearts were examined in the short-axis between the two papillary muscles of the left ventricle (LV) and analyzed in M-mode. The parameters of cardiac function were measured offline with the Velvo 770 software including LV end diastolic diameter (EDD), end-systolic diameter (ESD), posterior wall thickness (PWT), and septal wall thickness (SWT) to determine cardiac morphological changes and ejection fraction (EF), heart rate and fractional shortening (FS). The EF and FS were calculated as reported (Rottman et al., 2007, Echocardiography, 24(1), 83-9).

TUNEL Assay

Apoptotic cells were detected by terminal deoxynucleotidyl transferase-mediated nick-end labeling (TUNEL) using the APO-BrdU TUNEL Assay Kit (Millipore) as per the manufacturer's protocol. Briefly, Hearts were embedded in OCT media (Sakura Finetechnical Co., Ltd. Japan). Frozen ventricular sections (5 µm) were fixed in 4% (w/v) paraformaldehyde for 15 min on ice, permeabilized with 70% ethanol for 30 min on ice, and incubated with 50 µL DNA-labeling solution containing TdT enzyme and Br-dUTP at 37° C. for 60 min. After the labeling reaction, the sections were washed and stained with fluorescein-labeled anti-BrdU antibody for 30 min. Before mounting, the cells were stained with 4', 6-diamidino-2-phenylindole (DAPI) and Alexa Fluor 594-labeled phalloidin (Invitrogen). Images were captured using a Zeiss 710 confocal microscope, 63× oil objective, 1.4.× digital zoom with excitations at 405, 488, and 594 for nuclei, TUNEL, and phalloidin, respectively. The percentage of TUNEL positive cells was quantitated using Image J (NIH) from 4-5 regions per heart, and an area of at least 100 cardiac myocytes.

Capillary Density Assay

Mouse hearts were removed at two weeks after MI and kept at −80° C. until histological analysis. Frozen heart tissues were cut into 5 µm thick slices. Adjacent sections (taken at the midpoint between LAD ligation site and apex) were stained with Biotinylated Griffonia simplicifolia lectin I (isolectin B4) to stain endothelial cells in neovasculature from the mouse myocardial infarcted heart section (Chavakis et al., 2005, J Exp Med, 201(1), 63-72). Images were captured using a Zeiss 710 confocal microscope using a 63× oil objective and 1.4.× digital zoom with excitations at 405 and 594 for nuclei and IB4, respectively. Capillary density was expressed as IB4+ endothelial cells per field.

Data Analysis

All the experiments were performed at least twice, and results were expressed as the mean±standard error (S.E.). Statistical comparison of single parameters between two groups was performed by paired Student t test. One-way ANOVA was used to compare the means of multiple groups. Data were considered statistically significant if p was <0.0.5.

The results of the experiments are now described.

Hyperlipidemia Increases Caspase-1 Activity in Sca-1+ Progenitor Cells

Figures 21A, 21B, 21C:
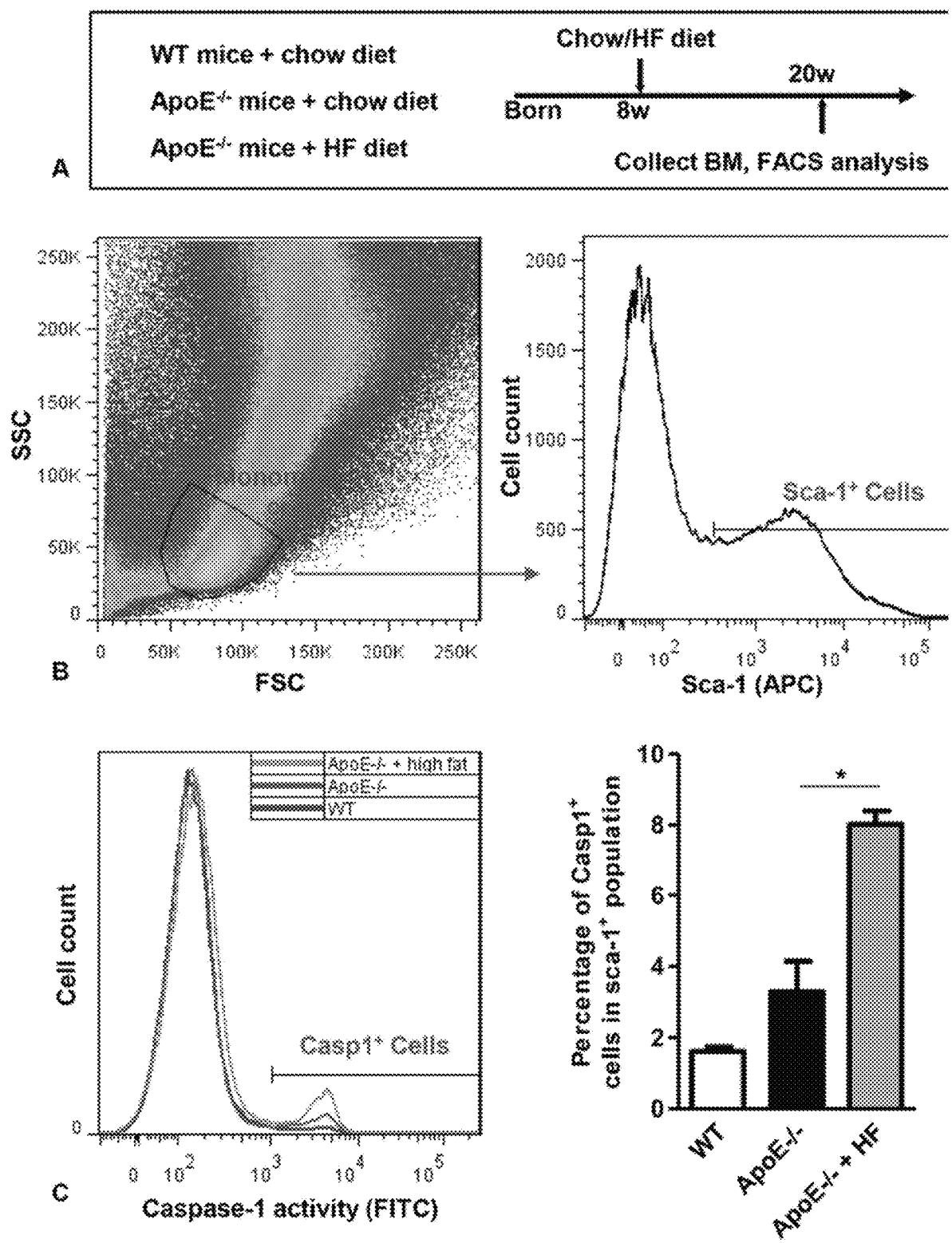
FIG. 21A through FIG. 21C, depicts experimental results showing hyperlipidemia increases caspase-1 activity in Sca-1$^+$ progenitor cells.

We and the others have shown previously that caspase-1 activation is responsible for hyperlipidemia-induced endothelial cell activation and macrophage inflammation (Yin et al., 2015, Arterioscler Thromb Vasc Biol; Duewell et al., 2010, Nature, 464(7293), 1357-61; Rajamaki et al, 2010, PLoS One, 5(7), e11765). However, the question of whether caspase-1 is activated in Sca-1+ progenitor cells in response to hyperlipidemia remained unknown. We hypothesized that Sca-1+ progenitor cells also had a functional inflammasome pathway, which could sense hyperlipidemia and activate caspase-1. To test this hypothesis, we measured caspase-1 activity in BM-derived Sca-1+ progenitor cells after hyperlipidemia challenge. We collected BM cells from WT mice and ApoE−/− mice fed with either chow diet or HF diet for 12 weeks and prepared single cell suspensions for flow cytometry analysis (FIG. 21A). Within the mononuclear cell populations of BM, we gated Sca-1+ progenitor cells to measure their caspase-1 activity (FIG. 21B). We found that when compared with either ApoE−/− mice or WT mice fed with chow diet, HF diet feeding significantly increased caspase-1 activity in mouse Sca-1+ progenitor cells ($p<0.0.5$) (FIG. 21C), suggesting that at least one type of NLR inflammasomes and caspase-1 are fully expressed/functional in progenitor cells and could be post-translationally activated by hyperlipidemia stimuli.

Figure 22:
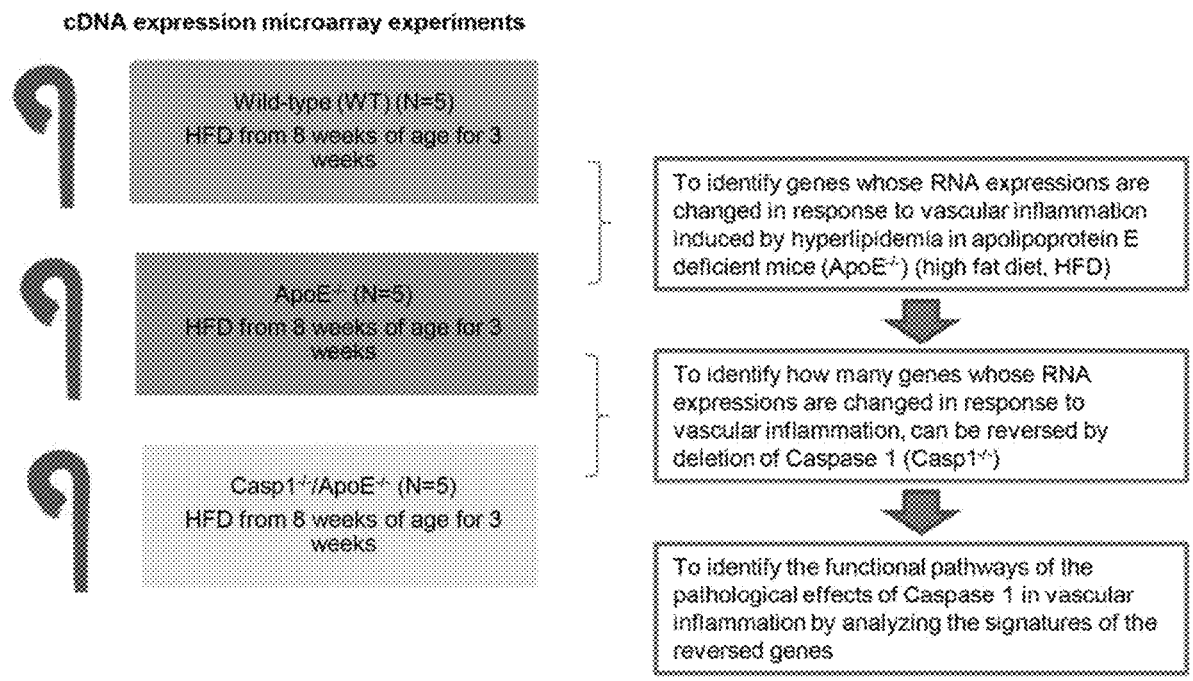
FIG. 22 depicts a flow chart of experiment design that was used for cDNA microarray analysis.
Figures 23A, 23B, 23C, 23D, 23E, 23F:
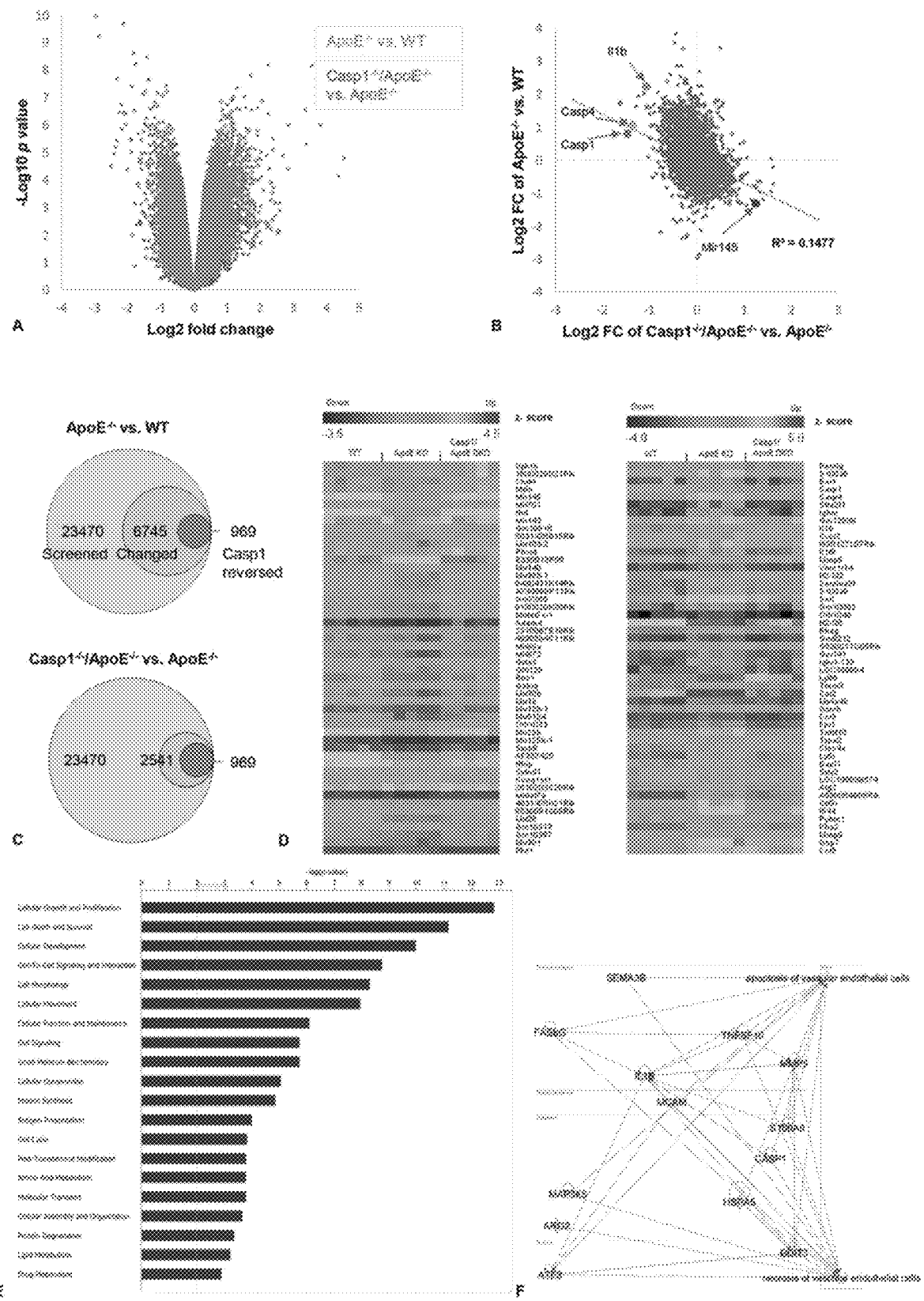
FIG. 23A through FIG. 23F, depicts experimental results showing caspase-1 contributes to hyperlipidemia-induced gene changes related to vascular cell death.

Caspase-1 Contributes to Hyperlipidemia-Induced Modulation of Vascular Cell Death Gene Expression A recent report showed that stem cells/endothelial progenitor cells were present at low levels in mouse organs with the highest levels in adipose and aorta (Russell and Brown, 2014, Mol Cancer, 13, 177). To determine the functional effects of hyperlipidemia-induced caspase-1 activation in Sca-1+ progenitor cells in mouse aortic context related to hyperlipidemia diseases, we performed cDNA microarray analysis in WT mice, ApoE−/− mice, and ApoE−/−Caspase-1−/− mice fed with 3 weeks of HF diet. Since we have found that caspase-1 serves as a hyperlipidemia sensor during early hyperlipidemia (Yin et al., 2015, Arterioscler Thromb Vasc Biol, 35(4), 804-16), use of three-week HF diet feeding is justified. Of note, at this age of mice, plasma cholesterol triples in both ApoE−/− and ApoE−/−Caspase-1−/− mice when compared with that in WT mice (Yin et al., 2015, Arterioscler Thromb Vasc Biol, 35(4), 804-16; Plump et al., 1992, Cell, 71(2), 343-53; Nakashima et al., 1994, Arterioscler Thromb, 14(1), 133-40). This allows us to identify genes whose RNA expressions are changed in response to hyperlipidemia (ApoE−/− mice compared with WT mice) and identify how many genes whose RNA expressions are changed in response to hyperlipidemia can be reversed by caspase-1 gene deletion (ApoE−/−Caspase-1−/− mice compared with ApoE−/− mice) (FIG. 22). We found that among 23,470 genes that could be detected by the microarray analysis, 6,745 genes were significantly changed in response to hyperlipidemia, while 2,541 genes were significantly changed in response to caspase-1 gene deletion (FIG. 23A and FIG. 23C). More importantly, most of the genes that were induced by hyperlipidemia could be significantly down-regulated by caspase-1 deficiency (FIG. 23B). Moreover, among 6,745 differentially expressed genes induced by hyperlipidemia, 969 genes could be reversed by caspase-1 deficiency (FIG. 23C). Interestingly, IL-1β, the proteolytic substrate of caspase-1, was among the most significantly decreased genes besides caspase-1 after caspase-1 deficiency (FIG. 23D). This result suggested that caspase-1 could also transcriptionally up-regulate IL-1β gene expression independent from its well-characterized enzymatic cleavage activity. In addition, we found that apoptosis-related gene caspase-4 was among the genes that decreased the most after caspase-1 deficiency, suggesting that caspase-1 also promotes apoptosis (programmed cell death) besides its ability to induce pyroptosis (inflammatory cell death). Moreover, a group of different microRNAs (Mir) such as Mir 145 and Mir 143 were among the most significantly increased genes after caspase-1 gene deficiency instead, which suggested that caspase-1 could negatively affect regulatory noncoding RNA gene expressions, thereby contributing to epigenetic regulation of gene expression changes.

Figure 24:
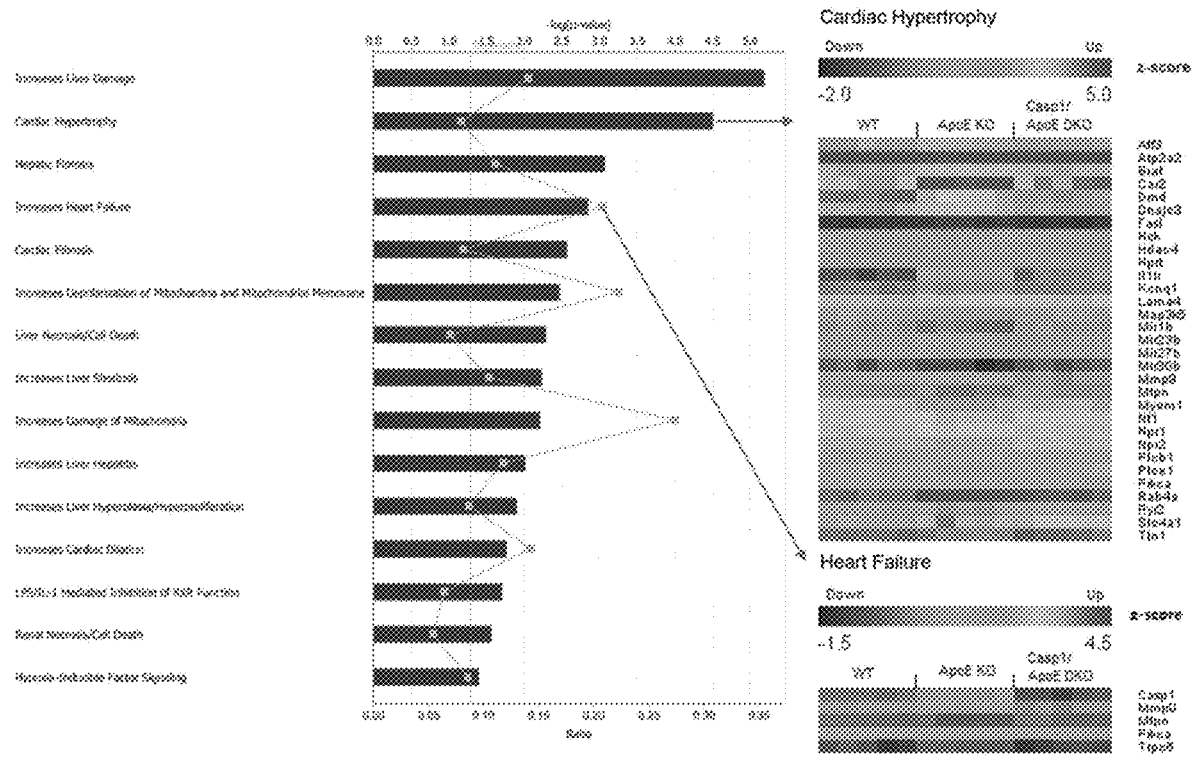
FIG. 24 depicts experimental results showing caspase-1 contributes to hyperlipidemia-induced gene changes related to heart dysfunction. Tox analysis with Ingenuity pathway analysis (IPA) shows that the clinical pathology endpoints of these reversed genes. Heart hypertrophy and heart failure are the top endpoints associated with cardiovascular disease. Heat-maps showing the expression level of the involved genes in each endpoint are listed in the right.

To identify the functional pathways of the pathological effects of Caspase 1 in hyperlipidemia, we analyzed the signatures of the 969 genes regulated by caspase-1 deficiency using IPA software. When we examined top molecular pathways that were regulated by caspase-1 in hyperlipidemia condition, "Cellular Growth and Proliferation", "Cell Death and Survival" were the top two pathways identified, suggesting that hyperlipidemia-induced caspase-1 regulates vascular cell death (FIG. 23E). In addition, we identified 13 genes associated with apoptosis and necrosis of endothelial cells that are regulated by hyperlipidemia-induced caspase-1 activation, such as tumor necrosis factor (TNF) super family members including tumor necrosis factor (ligand) superfamily member 10 (TNFSF 10) and Fas ligand (FASLG), matrix degradation enzyme metallopeptidase 9 (MMP9), and mitogen-activated protein kinase (MAPK) family member MAP3K5 (FIG. 23F). When we chose clinical endpoints as the readouts in our IPA analysis, we found that "Cardiac Hypertrophy" and "Increase Heart Failure" were among the top pathways that are regulated by hyperlipidemia-induced caspase-1 activation (FIG. 24). Although mouse aortas instead of heart were used in our analysis, caspase-1 might mediate hyperlipidemia-induced cardiac dysfunction and hypoxia-triggered damage by inducing vascular cell death in these tissues.

Caspase-1−/− Sca-1+ Progenitor Cell Therapy Improves Cardiac Function after MI

Based on our results above that that dyslipidemia increases caspase-1 activity in Sca-1+ progenitor cells; and that caspase-1 contributes to the regulation of hyperlipidemia-induced vascular cell death, we hypothesized hyperlipidemia-induced caspase-1 activation in Sca-1+ progenitor cells leads to vascular cell damage by impairing their vessel repair capacity. To test this hypothesis, we compared the angiogenesis capacity of purified Sca-1+ cells from WT mice and those purified from caspase-1 deficient mice in a mouse model of MI (Iwasaki et al., 2006, Circulation, 113(10), 1311-25). We used four groups of mice, (i) the mock-MI control group (n=13), (ii) the MI with no cell therapy control group (n=4), (iii) the MI with WT Sca-1+ progenitor cell therapy group (n=5), and (iv) the MI with caspase-1−/− Sca-1+ progenitor cell therapy group (n=5). As shown in FIG. 25A, we first pre-conditioned the mice with a six week HF diet feeding (from day −42 to day 0). Sca-1+ progenitor cells were purified using a magnetic Sca-1+ cell purification column, and Sca-1+ cells were enriched from 35.5.% to as high as 85.4.% after the purification (FIG. 25A). Then, we performed experimental acute MI procedures at the day 0 (18), to the three groups of the recipient mice, followed by Sca-1+ progenitor cell therapy ($2\times10^6$ cells/mouse). The numbers of transferred Sca-1+ progenitor cells were similar to $1\times10^6$ BM-derived cells per mouse in a previous report (Chen et al., 2009, Am J Pathol, 174(2), 701-11). After MI, the control mice received purified WT Sca-1+ progenitor cells and the experimental mice received caspase-1−/− Sca-1+ purified progenitor cells. To ensure that Sca-1+ progenitor cells migrate to the acute MI lesion site, we used CellVue® NIR780-labelled Sca-1+ progenitor cells ($2\times10^6$ cells/mouse, n=4) to perform adoptive transfer to trace the Sca-1+ progenitor cell migration. 45 hours after the injection, we found that the CellVue® NIR780 near-infrared labeled Sca-1+ progenitor cells mostly migrated to the infarcted heart (FIG. 25B). To examine whether caspase-1−/− Sca-1+ progenitor cell therapy has an enhanced therapeutic effects, we performed cardiac function analysis one day before MI and 14 days after MI using the M-mode echocardiography. The M-mode tracings presented in FIG. 25C were obtained from WT mice without MI (control) and with MI using a 13 MHz transducer with the depth from 0 to −1 cm for 500 milliseconds as reported (Scherrer-Crosbie and Thibault, 2008, J Am Soc Echocardiogr, 21(10), 1083-92). The ejection fraction (EF) and fractional shortening (FS) are two commonly examined cardiac functions assayed by the M-mode echocardiography. As shown in FIG. 25D left panel, the ejection fraction in the mouse group receiving caspase-1−/− Sca-1+ progenitor cell therapy was increased to 39.9.% from 23% in the mouse group receiving WT Sca-1+ progenitor cell therapy control ($p<0.0.5$). Similarly, the faction shorten index (FIG. 25D right panel) in the mouse group receiving caspase-1−/− Sca-1+ progenitor cell therapy was also increased to 19.5% from 10.4.% in the mouse group receiving WT Sca-1+ progenitor cell therapy control ($p<0.0.5$). These results suggest that caspase-1−/− Sca-1+ progenitor cell therapy significantly improves cardiac function compared to WT Sca-1+ progenitor cell therapy. In addition, we also examined weight ratios and liver weight/body weight ratios in the three MI groups. As shown in FIG. 25E, the heart weight/body weight ratios and liver weight/body weight ratios were not significantly changed among three MI groups. In contrast, the lung weight/body weight ratios in the caspase-1−/− Sca-1+ progenitor cell therapy group were significantly decreased to 0.0.075 from 0.0.119 (WT Sca-1+ cell therapy) and 0.0.094 (no cell therapy control)($p<0.0.5$). The results suggest that the improved cardiac function in caspase-1−/− Sca-1+ progenitor cell therapy group may have relieved lung congestion and edema. Taken together, our results suggest that caspase-1−/− Sca-1+ progenitor cell therapy significantly improves cardiac function.

Figures 26A, 26B:
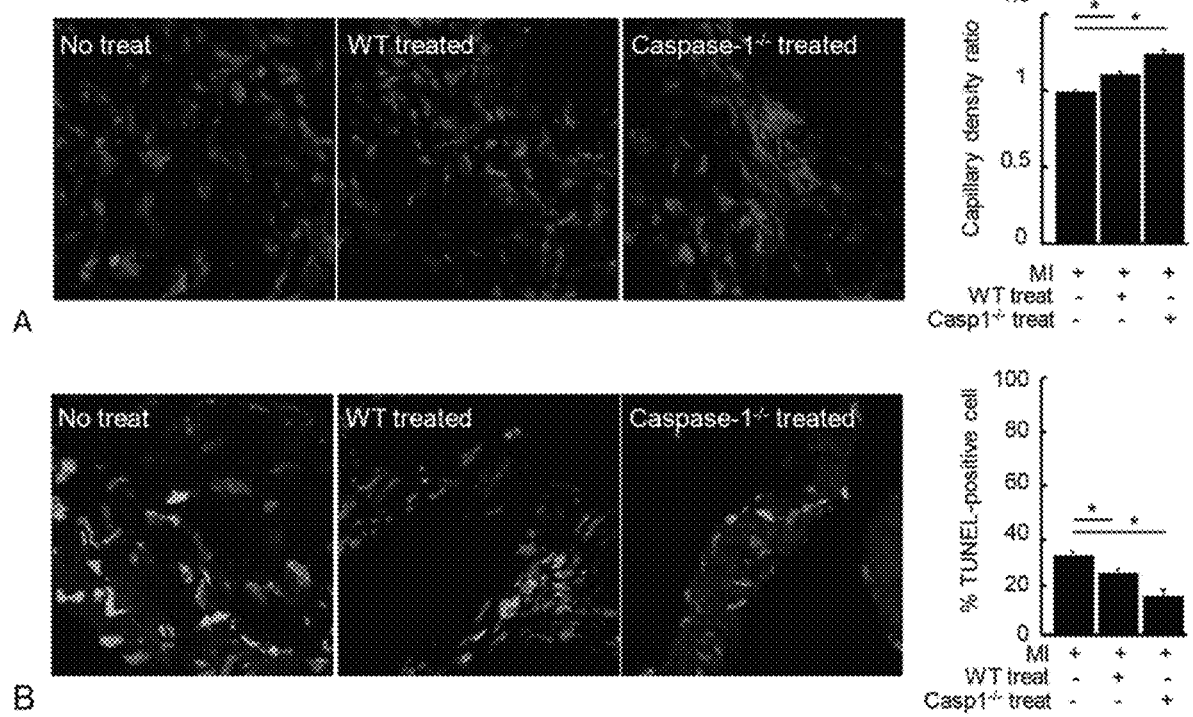
FIG. 26A and FIG. 26B, depicts experimental results showing caspase-1$^{-/-}$ Sca-1$^+$ progenitor cell therapy increases IB4$^+$ capillary density and decreases TUNEL$^+$ cardiomyocytes.

Caspase-1−/− Sca-1+ Progenitor Cell Therapy Improves Endothelial Capillary Density and Decreases Cardiomyocyte Cell Death in the Infarcted Heart Zone after MI To determine the mechanisms underlying the beneficial effects of caspase-1−/− Sca-1+ progenitor cell therapy, we then hypothesized that the enhanced regenerative capacity of caspase-1−/− Sca-1+ progenitor cell therapy resulted from improved neovasculature formation and reduced cardiac myocyte cell death in comparison to the mice receiving WT Sca-1+ progenitor cells. To test this hypothesis, we examined whether mouse hearts receiving caspase-1−/− progenitor cell therapy have higher endothelial capillary density after MI than mouse hearts receiving WT Sca-1+ cell therapy using IB4 to stain endothelial cells in neovasculature from the infarcted heart sections (Chavakis et al., 2005, J Exp Med, 201(1), 63-72). The immunohistochemistry results in FIG. 26A showed that the infarcted heart section from the mice receiving caspase-1−/− Sca-1+ progenitor cell therapy have higher numbers of IB4+ endothelial cells than that of untreated MI hearts and that of the MI mice receiving WT Sca-1+ progenitor cell therapy. The fold change of IB4+ endothelial cell numbers in caspase-1−/− Sca-1+ progenitor cell therapy group over no treatment MI group is 1.3.1 ($p<0.0.5$). Then, we examined whether the enhanced angiogenesis in the MI lesion area of mice receiving caspase-1−/− Sca-1+ progenitor cell therapy leads to the reduction of cardiomyocyte cell death using TUNEL assay. The results in FIG. 26B showed that the infarcted heart sections from the mice receiving caspase-1−/− Sca-1+ progenitor cell therapy have lower numbers of TUNEL+ cardiomyocytes (14.9.%) than that of untreated MI hearts (30.8.%) and that of the MI mouse hearts receiving WT Sca-1+ progenitor cell therapy (25.1.%)($p<0.0.5$). Taken together, our results suggest that caspase-1−/− Sca-1+ progenitor cell therapy improves cardiac function from enhanced angiogenesis and reduction of cardiomyocyte cell death after MI.

Caspase-1 Inhibitory Progenitor Cell Therapy

Stem cell based therapies for the prevention and treatment of CVDs such as myocardial infarction have attracted considerable interest since it was reported in 2001 that BM-derived stem cells could repair myocardial infarcts in mice (Orlic et al., 2001, Ann N Y Acad Sci, 938, 221-9; discussion 229-30). Originally it was considered that stem cell therapies reverses myocardial remodeling by directly incorporate into the myocardium for de novo myocardiogenesis, it is believed today that the beneficial effects of stem cell therapy on ischemic myocardium are mainly due to neovascularization and paracrine effects (Kinnaird et al., 2004, Circulation, 109(12), 1543-9). The results from clinical trials suggest that stem cell therapy for the prevention and treatment of cardiac dysfunction is safe and potentially efficacious, but the therapeutic efficacy of stem cell therapy is greatly hampered by poor survival, proliferation, engraftment, and differentiation of the grafted stem cells due to the hostile microenvironment of ischemic tissue such as hyperlipidemia, hypoxia, and inflammation (Penn and Mangi, 2008, Circ Res, 102(12), 1471-82; Yang, 2007, Cell Mol Immunol, 4(3), 161-71). To overcome these limitations, a number of studies utilized genetic engineering and pharmacological approaches to empower stem cells for myocardial regeneration (Mohsin et al., 2011, Circ Res, 109(12), 1415-28). However, three important questions remained poorly determined: first, whether progenitor cells have a functional caspase-1 pathway in sensing dyslipidemia/hyperlipidemia; second, whether caspase-1 induced cell death pathways including pyroptosis, apoptosis, and necrosis weaken angiogenesis and vascular repair function of progenitor cells after hyperlipidemia stimulation; and third, whether inhibition of caspase-1 in progenitor cells improves their angiogenesis capacity after MI. In this report, by using various techniques including immunological, biochemical, microarray analysis followed by bioinformatics analysis, gene deficient mice, cell therapy, experimental MI model, and mouse cardiac function assessment, we have made the following important findings: 1) Dyslipidemia increases caspase-1 activity in Sca-1+ progenitor cells; 2) Caspase-1 gene deficiency significantly reversed hyperlipidemia-induced gene changes in mouse aortas including progenitor cells, some of which are involved in vascular cell death; 3) Caspase-1−/− Sca-1+ progenitor cell therapy significantly improves mouse cardiac functions after MI compared to the Sca-1+ progenitor cell treatment; and 4) Caspase-1−/− Sca-1+ progenitor cell therapy improves capillary endothelial cell density and decrease cardiomyocyte cell death after MI. Taken together, our novel findings have provided the first insight on the role of dyslipidemia as DAMP in promoting caspase-1 dependent impairment of progenitor cell repairing capacity after MI.

As we pointed out in our recent review, several types of inflammasomes involved in activating caspase-1 have been characterized including NLRP1, NLRP3, NLRC4 (IPAF), NFLRP6 and NLRP12 (Yin et al., 2013, Front Biosci (Landmark Ed), 18, 638-49). Among these, the NLRP3 inflammasome is the only one found to activate caspase-1 in response to endogenous metabolic danger signals (DAMPs) including lipid metabolites. Nevertheless, future work is needed to verify the role of NLRP3 inflammasome in activating caspase-1 in Sca-1+ progenitor cells. A previous report showed that inhibition of caspase-1 in BM-derived progenitor cells from patients and mice with systemic lupus erythematosus improves their differentiation ability (Kahlenberg et al., 2011, J Immunol, 187(11), 6143-56). However, the questions related to caspase-1 activation in progenitor cells in response to dyslipidemia and its effects on angiogenesis and vascular repair after MI have not been examined until this study.

Figure 27:
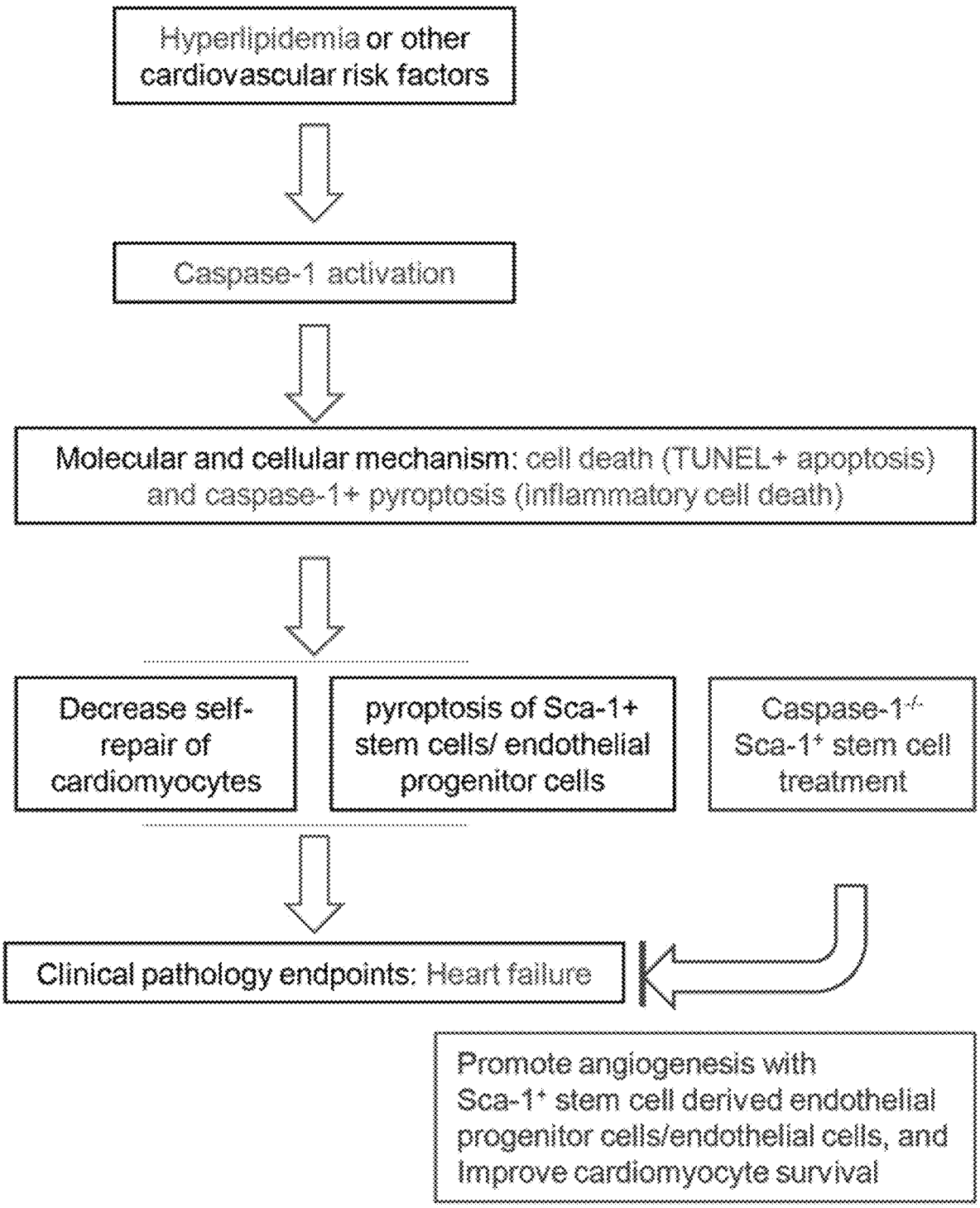
FIG. 27 depicts a new working model that caspase-1 inhibition improves Sca-1+ stem cell therapy for myocardial infarction. Hyperlipidemia activates caspase-1 activation in Sca-1+ stem cells and vascular cells in aorta. Activation of caspase-1 upregulates proinflammatory gene expression and promotes pyroptosis and apoptosis presumably in Sca-1+ stem cells, endothelial cells and cardiomyocytes and causes cardiac dysfunction. Inhibition/depletion of caspase-1 improves survival of Sca-1+ stem cells/progenitor cells, and cardiomyocytes, promotes angiogenesis, and improves cardiac function after myocardial infarction.

In addition to the phenotypic characterization of caspase-1-/- Sca-1+ progenitor cell therapy for MI, we have also made the findings that after MI, caspase-1-/- Sca-1+ progenitor cells improved capillary density and enhanced cardiomyocyte survival after MI, which are the mechanisms underlying the better efficiencies of caspase-1-/- Sca-+ progenitor cell therapy and better cardiac function in comparison to that of WT Sca-1+ progenitor cells. Since that caspase-1 is the converting enzyme responsible for the maturation of pro-interleukin-1β (pro-IL-1β) and pro-IL-18 into IL-1β and IL-18, respectively (Shen et al., 2010, Atherosclerosis, 210(2), 422-9); and that caspase-1 deficiency results in deficiency of functional IL-1β and IL-18 and decreased secretion of tumor necrosis factor-α (TNF-α) (Yin et al., 2013, Front Biosci (Landmark Ed), 18, 638-49), there might be less proinflammatory cytokines IL-1β, IL-18 and TNF-α in the downstream of caspase-1 activation, resulting in improved vessel repair ability in the caspase-1-/- Sca-1+ progenitor cells. Finally, we and others have reported previously that Sirtuin 1 (Sirt1), an inhibitory NAD+-dependent histone deacetylase, is cleaved by caspase-1 after hyperlipidemia stimulation (Yin et al., 2015, Arterioscler Thromb Vasc Biol, 35(4), 804-16; Chalkiadaki and Guarente, 2012, Cell Metab, 16(2), 180-8). Disruption of Sirt1 gene results in defective blood vessel formation and inhibits ischemia-induced neovascularization (Potente et al., 2007, Genes Dev, 21(20), 2644-58). Thus, caspase-1-/- Sca-1+ progenitor cells might retain the Sirt1 function, which may also benefit ischemia-induced neovascularization during MI. Based on these analyses, we have proposed a new working model to integrate our findings (FIG. 27). In summary, our results hold a promise for the future development of caspase-1 inhibitory progenitor cell therapy for inflammatory diseases, ischemic diseases, and cancers.

Example 4: Caspase-1 Plays a Critical Role in Accelerating Chronic Kidney Disease-Promoted Neointimal Hyperplasia Chronic kidney disease (CKD) affects over 15% of the adult population (Levey et al., 2003, Ann Intern Med 139: 137-47; Basnakian et al., 2010, Adv Clin Chem 51:25-52) and is a significant contributor to morbidity and mortality in the general population. CKD results from a progressive loss in renal function and is identified by pathological high levels of plasma creatinine, which results from a lower glomerular filtration rate (GFR, <60 ml/min/1.73 sq. meters) (Foundation, 2002, Am J Kidney Dis 39:S1-266). Thus, due to a decrease in kidney function, CKD results in an accumulation of metabolic wastes such as urea and other uremic toxins (Moradi et al., 2013, Am J Nephrol 38:136-48). When the kidney function drops to 10-15% of normal kidney function, the hemodialysis procedure is indicated for the patient survival (Feldmen et al., 1996, J Am Soc Nephrol 7:523-35). Moreover, it has been demonstrated that the CKD patients have a significantly increased incidence in the development of cardiovascular disease (CVD) and patient's mortality (Go et al., 2004, N Engl J Med 351:1296-305). Several vascular disorders in CKD patients, such as atherosclerosis, arteriovenous fistula (AVF) stenosis in CKD-dialysis patients and allograft vasculopathy, are associated with the development of neointima hyperplasia (NH) and stenosis of the vessel lumen. Recent reports have shown that the uremic's state in CKD accelerates the development of NH in CKD patients with AVF (Langer et al., 2010, Kidney Int 78:1312-21; Kokubo et al., 2009, J Am Soc Nephrol 20:1236-45). In addition, previous data also suggested that NH is present prior the AVF creation in CKD patients (Wasse et al., 2012, J Vasc Access 13:168-74). Moreover, other studies demonstrated that humans and pigs fed with high fat diet develop atherosclerosis at site of preexisting NH (Kim et al., 1987, Atherosclerosis 64:321-42; Schwartz et al., 1995, Circ Res 77:445-65; Stary et al., 1992, Arterioscler Thromb 12:120-34; Virmani et al., 2000, Arterioscler Thromb Vasc Biol 20:1262-75). Therefore, it is urgent to identify novel therapies to inhibit the initiation and progression of NH in CKD patients.

The Neointimal Hyperplasia refers to inward proliferation and migration of vascular smooth muscle cells (VSMC) primarily in the tunica intima, resulting in the thickening of arterial walls and decreased arterial lumen space. Fully differentiated VSMC are associated with high expression of several specific contractile proteins that include smooth muscle α-actin, smooth muscle myosin heavy chain, SM22 and calponin (Alexander and Owens, 2012, Annu Rev Physiol 74:13-40) in a healthy kidney-controlled plasmic and artery environment. In contrast, VSMC exhibit a "contractile" to a "synthetic" phenotypic change by the down-regulation of VSMC contractile gene expression in response to vascular injury induced by CKD, uremia and mechanic stress as we recently reported (Monroy et al., 2014, Front Biosci (Landmark Ed) 20:784-95). This "synthetic" phenotype is characterized by the loss of contractility, abnormal proliferation, as well as migration and matrix secretion that is an important step in the formation of NH. The VSMC "synthetic" phenotype can induce inward remodeling, significantly narrow the vessel lumen, and accelerate the development of various vascular pathologies such as atherosclerosis, hypertension and post-angioplasty restenosis (Regan et al., 2000, J Cin Invest 106:1139-47; Owens et al., 2004, Physiol Rev 84:767-801). However, the sensing molecular mechanism which bridges elevated metabolic wastes and uremic toxins in plasma and increases the mechanic stress on the initiation and development of NH in CKD patients remains unknown.

The Toll-like receptors (TLR) are located in the plasma membrane and recognize a variety of conserved microbial pathogen-associated molecular patterns (PAMP) and danger signal-associated molecular patterns (DAMP) as well as promote proinflammatory gene transcription. As we described previously (Yin et al., 2009, Int J Immunopathol Pharmacol 22:311-22), for tissues in which receptors for DAMP are not constitutively expressed, TLR also work in synergy with cytosolic sensing receptor families, which include NLR [NOD (nucleotide binding and oligomerization domain)-like receptors], to recognize endogenous DAMP and mediate the upregulation and activation of a range of inflammatory genes (Yin et al., 2013, Front Biosci 18:638-49). Caspase-1 is a member of the cysteine protease family of caspases that requires the posttranslational cleavage and assembly of a NLR family member-containing protein complex called "inflammasome" for activation and is present in the cell cytosol as an inactive zymogen pro-caspase-1. Activated caspase-1 is required for the cleaving and processing of pro-interleukin-1β (pro-IL-1β) and pro-IL-18 into functional mature pro-inflammatory cytokines IL-1β and IL-18, respectively, as well as the activation of other inflammatory pathways. Although caspase-1 inflammasome activation has been reported in the pathogenesis of kidney disease (Anders and Muruve, 2011, J Am Soc Nephrol 22:1007-18), an important issue of whether caspase-1 plays any role in CKD-accelerated NH and VSMC phenotypic change from a "contractile" to a "synthetic" phenotype remains unknown.

In this study, we examined a novel hypothesis that caspase-1 promotes the CKD-induced VSMC switch from a "contractile" to "synthetic" phenotype and the NH development. We applied a carotid artery ligation mouse model reported previously (Kumar et al., 1997, Cirulcation 96:4333-42) on the CKD model we developed (Kokubo et al., 2009, J Am Soc Nephrol 20:1236-45) for the development of neointimal hyperplasia in wild-type (WT) and caspase-1 gene deficient (caspase-1−/−) mice (Kuida et al., 1995, Science 267:2000-3). Our data has demonstrated that caspase-1 plays a critical role in the downregulation of VSMC contractile marker gene expression and promotion of neointimal hyperplasia formation in CKD mouse models.

The materials and methods employed in this example are now described.

Human Vascular Smooth Muscle Cell Culture and Uremic Serum Collection

Blood samples were obtained from 6 healthy donors with normal kidney function and 20 patients with end stage renal disease who were on hemodialysis. In HD, blood was collected prior to the routine HD session as we reported (Lee et al., 2010, Nephrol Dial Transplant 27:4166-72). Blood samples were centrifuged at 3,000 revolutions per minute (rpm), and the serum was aliquoted and incubated at −80° C. Human aortic smooth muscle cells (HAVSMC) were obtained from Lonza (CC-2571, Allendale, N.J.) and cultured in smooth muscle basal media (SmBM) supplemented with growth factors and 5% fetal bovine serum (FBS) (CC-3182, Lonza), according to the manufacturer's guidelines. Cells from passage 4-8 were used in the described studies. For experimental conditions, growth medium was supplemented with 10% vol./vol. normal or uremic serum. We used pooled serum from (3-5) maintenance hemodialysis patients in each experiment. Experiments were repeated using serum from different hemodialysis patients. Normal serum pooled from healthy donors was used for comparison in the different assays. The human aortic vascular smooth muscles cells were serum starved for 48-72 hours followed by serum treatment for 24 hours. The cells were then treated with serum, patient CKD serum and caspase-1 inhibitor (Z-YVAD-FMK, BioVision, Inc., Milpitas, Calif.) and CKD serum. Untreated serum starved cells were used as a control.

RNA Extraction and Quantitative Real-Time PCR

Total RNA from cultured cells was extracted using the RNeasy kit (Qiagen, Valencia, Calif.), and cDNA was synthesized with the VILO first-strand synthesis system (Invitrogen, Grand Island, N.Y.). In real time PCR, cDNA was amplified with inventoried gene assay products containing two human gene specific primers (ACTA2 (SMA), Hs00909449_m1; CNN1 (calponin), Hs00923894_m1; Applied Biosystems, Grand Island, N.Y.), four mouse gene specific primers (Acta2, Mm725412_sl; Cnnl, Mm00487032_m1; Sm22 (Tagln), Mm00441661_g1; and Smtn, Mm00449973_m1; Applied Biosystems) and one FAM dye labeled Taq Man MGB probe all using the 7500 Real Time PCR System (Applied Biosystems). Relative gene expression levels were calculated after normalization with the internal control eukaryotic 18S gene using the $2^{-deltadeltaCt}$ method, where Ct is the threshold value.

Mouse carotid arteries from five WT and five Caspase−/− mice were collected and frozen. Total RNA was later extracted using Trizol (Invitrogen). For arrays, 1 g of RNA was reversed transcribed using the RT Kit Qiagen. A genomic DNA elimination step is employed before the reverse transcription step. cDNAs were then used for gene expression analysis using the mouse inflammasome array (Qiagen). For vascular smooth muscle cell gene expression, cDNA was assayed using gene specific Taq Man probes as described above.

Mice

All animal studies were conducted in accordance with the principles and procedures outlined in the National Institute of Health Guide for the Care and Use of Animals. Mice were housed in veterinarian-supervised AALAC-accredited facilities. The proposed experiments were approved by the Animal Care and Use Committee Institutional Review Board of Temple University School of Medicine. We purchased WT (C57BL/6) mice from the Jackson Laboratory (Bar Harbor, Me.). Caspase-1−/− (background, C57BL/6) mice animals were generously provided by Dr. Richard Flavell from Yale University (Kuida et al., 1995, Science 267:2000-3). For CKD experiments, we used 9- to 16-week-old male mice in the study. The mice were housed in polycarbonate cages in a pathogen-free, temperature-controlled environment with free access to a standard chow diet and water.

Creation of CKD and Sham Mice

A two-step process was used in the creation of a chronic kidney disease state in mice by the wide-used 5/6 nephrectomy as reported (Eddy et al., 2012, Pediatr Nephrol 27:1233-47). The left kidneys of 9-week old male mice were ablated through a 2 cm flank incision using electrocautery (Surgistat B Electrosurgical Generator, Valleylab, Covidien, Mansfield, Mass.). One week after this first procedure we performed a contralateral nephrectomy using a 2 cm flank incision. Again, one week post nephrectomy we performed a BUN analysis using reagents a kit from STANBIO Laboratory (Issaquah, Wash.). Sham control animals received sham operations that included the de-capsulation of both kidneys during the same time periods as the CKD mice. One week later after these initial steps, WT CKD, caspase-1−/− CKD, and WT sham-surviving mice underwent carotid ligation.

Creation of Carotid Ligation

The WT CKD, caspase-1−/− CKD and WT sham-surviving mice underwent common left carotid ligation as reported (Kokubo et al., 2009, J Am Soc Nephrol 20:1236-45). Under sterile conditions, a vertical incision was made in the left neck with the left common carotid artery and carefully dissected out. The carotid bifurcation was identified and a 7-0 prolene suture (Ethicon, Somerville, N.J.) was used to ligate the common carotid artery at the level of the bifurcation. Three weeks after the creation of the arterial injury, we euthanized the mice and perfusion-fixed the left common carotid via a left ventricle puncture and perfusion of formalin at 100 mmHg for 15 minutes.

Histomorphometry

Figure 28:
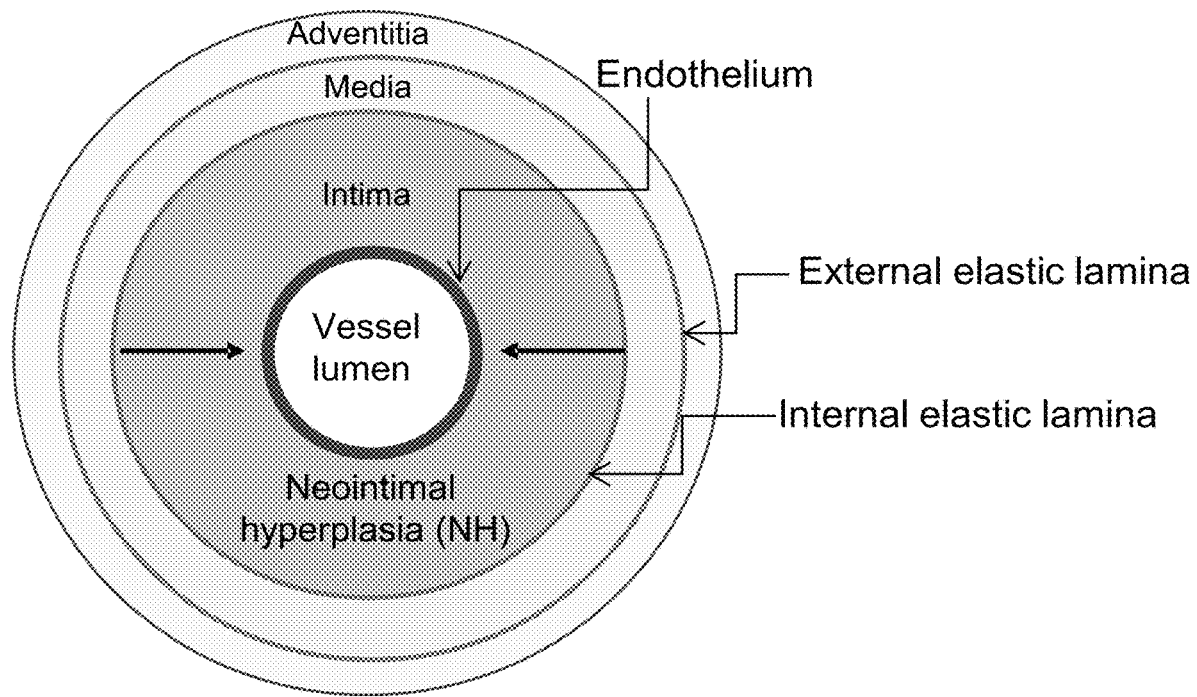
FIG. 28 is a schematic representation of the neointimal hyperplasia (NH) development. The area enclosed by the black arrows is the intima. The black arrows show the direction of inward remodeling.

The left common carotid artery distal to the ligation extending all the way to the ostia at the level of the aortic arch was harvested at the time of sacrifice. Samples were processed and embedded in paraffin. Serial sections of 5 μm thickness every 100 μm were obtained throughout the entire left common carotid artery including the ligation injury, and Artery sections were stained with the Verhoeff elastic-van Gieson (VvG), hematoxylin and eosin (H&E) (Polysciences, Warrington, Pa.). For immunohistochemistry, adjacent sections were stained for vascular smooth muscle cells (SM alpha-actin, 1:500 dilution; Sigma-Aldrich, St. Louis, Mo.). Volumetric measurements for NH lesion and thrombus were performed on digitizing images using Image J software (National Institutes of Health). As described in FIG. 28, measurements were made of the vessel lumen area, neointimal area (enclosed by the black arrows), medial area and the adventitia. The percentage of luminal stenosis was calculated using the formula (1−A/C)×100. The ratio of intimal (I) area to medial area (M) was calculated using the formula I area/M area=(B−A)/(C−B). The results of these parameters from each mouse group were averaged to obtain the mean values for luminal stenosis.

Statistics

The results were shown as the mean±2 standard deviations (SD). Excel statistical package was used for the quantitative analysis. The results were analyzed for statistical variance using an unpaired t test. The results were considered statistically significant at values of $p<0.05$.

The results of the experiments are now described.

Figure 29:
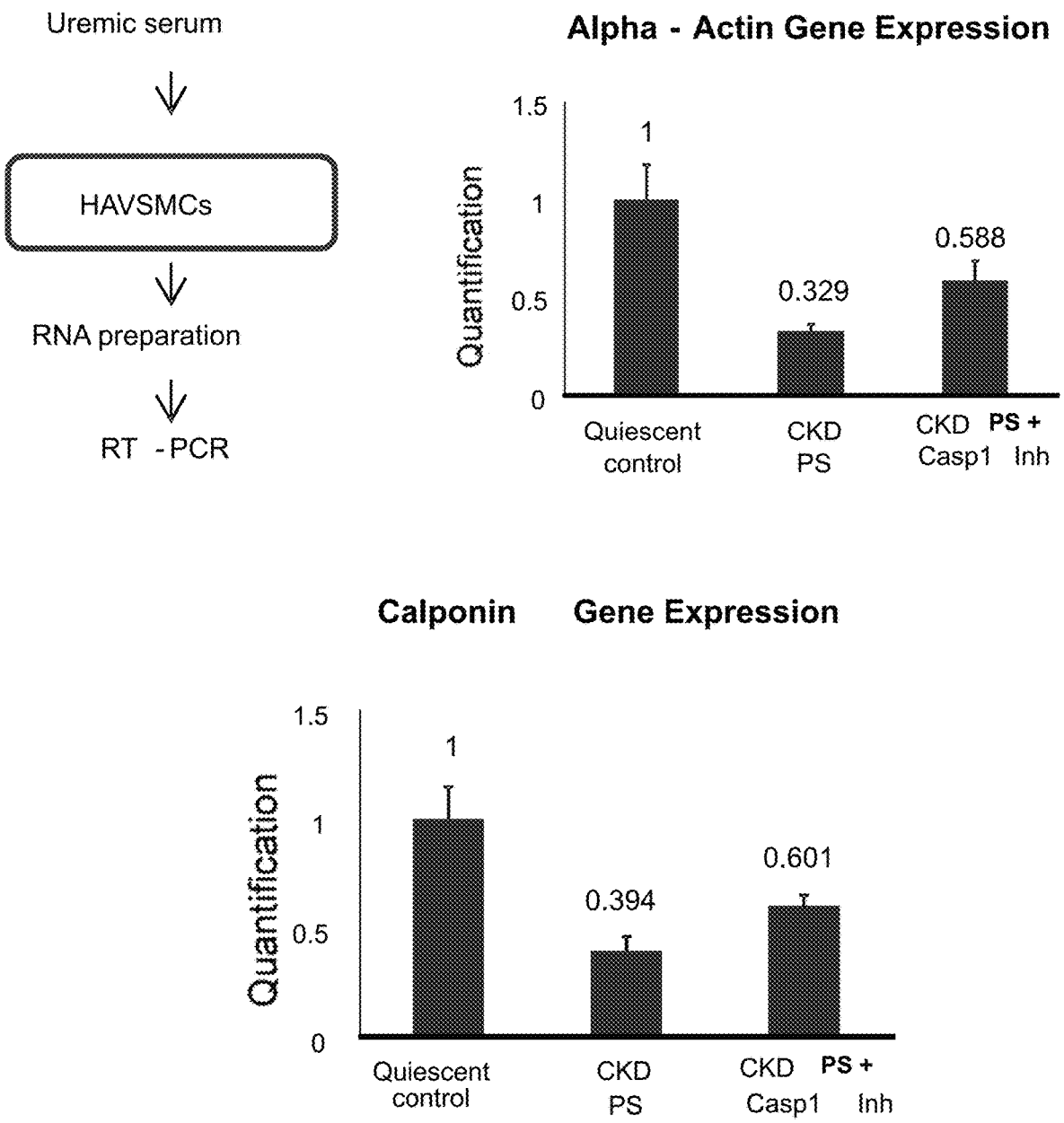
FIG. 29 depicts experimental results showing the exposure of human aortic vascular smooth muscle cells (HAVSMCs) to uremic serum decreases the expression of contractile marker RNA transcripts, which is reversed by the inhibition of caspase-1. HAVSMCs were grown to sub-confluence and were serum starved for 24 hours and exposed to 10% pooled uremic sera from CKD patients (CKD PS) with and without Caspase-1 Inhibitor (Casp1 inh) for another 24 hours. The RNA was extracted, was reverse transcribed into cDNA, and the expression of smooth muscle contractile marker RNA transcripts (alpha actin and calponin) was measured by quantitative RT-PCR using the Applied Biosystems 7500, Taqman primers and probes. The relative quantification of gene RNA expression is presented after being normalized with the expression of a house-keeping gene. *P value<0.005.

Caspase-1 Inhibition Partially Corrects CKD Patients' Serum-Induced Downregulation of VSMC Contractile Gene Markers We hypothesized that the caspase-1 activation pathway in VSMC may be able to sense elevated uremic metabolic waste in CKD patients' serum and make VSMC undergo the phenotypic change from "contractile" to "synthetic" based on the newly identified role of the caspase-1 inflammasome pathway as a major sensor for endogenous metabolic waste-related DAMP (Yin et al., 2013, Front Biosci 18:638-49). To examine this novel hypothesis, we adopted an in vitro cultured human primary aortic VSMC (HAVSMC) treated with CKD patients' serum and focused on the detection of VSMC contractile gene marker downregulation. The results showed that the exposure of HAVSMC to pooled CKD patient sera significantly decreased the expression of contractile muscle markers to a relative quantification of 0.329 for alpha-actin and 0.394 for calponin compared to non-treated controls, which suggested that the in vitro model was valid. In addition, caspase-1 inhibition partially rescued the downregulation of CKD patient sera-induced contractile muscle markers and increased the relative quantification to 0.588 for alpha-actin and 0.601 for calponin, when compared to that of the non-treated controls (FIG. 29). These results suggest that the caspase-1 activation pathway in VSMC may be able to sense elevated uremic metabolic wastes in CKD patients' serum and make VSMC undergo the phenotypic change from "contractile" to "synthetic"; and that inhibition of caspase-1 activity in VSMC partially corrects the downregulation of CKD patients' serum-reduced VSMC contractile markers.

Figures 30A, 30B:
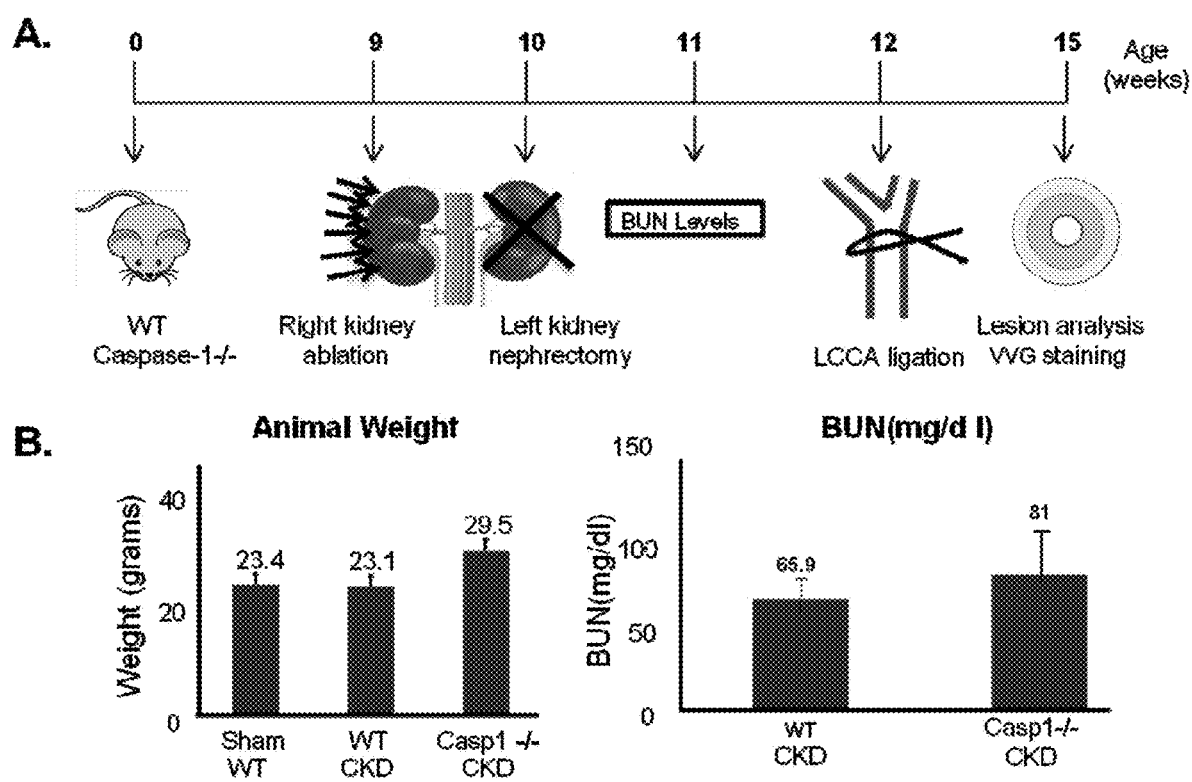
FIG. 30A and FIG. 30B, depicts experimental results showing that the 5/6 nephrectomy CKD model is established in wild-type (WT) mice and caspase-1−/− mice, and is followed by creation of the neointimal hyperplasia (NH) model with left common carotid ligation in CDK mice.

BUN Level is not Significantly Different in Wild-Type CKD Mice Versus Caspase-1−/− CKD Mice In order to determine the role of caspase-1 in the development of neointimal hyperplasia in the carotid artery, the murine CKD model (FIG. 30A) was established in 10 WT mice and 10 caspase-1−/− mice. In addition, 10 WT mice were used to create a Sham-surgery model as controls. After the creation of the CKD model, the mice underwent serum biological analysis. The results showed that there were no significant differences in the tested biological measurement between the WT and caspase-1−/− CKD mice (FIG. 30B). Although the blood urea nitrogen (BUN) level in WT CKD mice was significantly higher than that reported for the WT mice (24.60±2.62) (Lichtnekert et al., 2011, PLoS One 6:e26778), the BUN level did not show significant differences between WT CKD mice and caspase-1−/− CKD mice (65.9±11.64 mg/dL versus 71.43±35.5 mg/dL; p<0.18), and the BUN levels in WT CKD mice were similar to that of what we reported previously (Kokubo et al., 2009, J Am Soc Nephrol 20:1236-45), suggesting that the CKD model was established successfully. Moreover, there were no significant differences in body weight between the groups at the time of left common carotid artery (LCCA) ligation, and the body weights were in the reported range (Kokubo et al., 2009, J Am Soc Nephrol 20:1236-45). Of note, a previous report showed that neither inflammasome components NLRP3-, ASC- nor caspase-1-deficiency had any significant effect on renal histopathology nor the proteinuria of serum nephritis (Lichtnekert et al., 2011, PLoS One 6:e26778), which were all well correlated with our results that no significant change was found in the BUN level of WT CKD mice and caspase-1−/− CKD mice. Taken all together, these analyses suggest that the caspase-1 inflammasome pathway may not play a significant role in the kidney pathogenesis caused by the trauma in the CKD model nor does it have a direct adaptive immune response in the serum/antibody-triggered nephritis model (Lichtnekert et al., 2011, PLoS One 6:e26778).

Figures 31A, 31B, 31C, 31D, 31E:
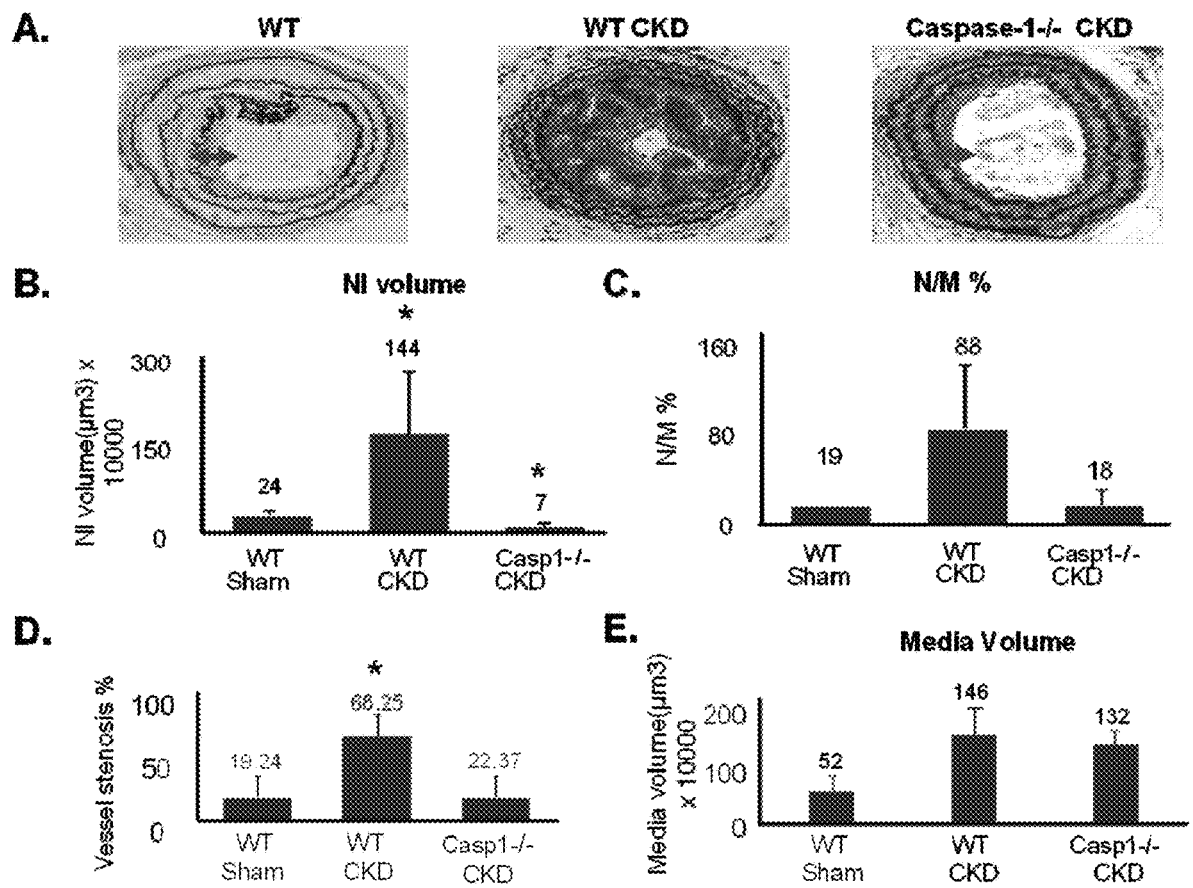
FIG. 31A and FIG. 31E, depicts experimental results showing the deficiency of caspase-1 reduces the CKD-induced carotid neointimal hyperplasia development in mice.
FIG. 31B depicts results showing the neointimal (NI) volume is significantly increased in WT CKD mice compared with that in WT sham; the NI is diminished in caspase-1−/− CKD mice compared with that of WT CKD mice.
FIG. 31C depicts results showing the NI/Media (NI/M) ratio (%) is significantly increased in WT CKD mice compared with that in WT sham; the NI/M ratio is diminished in caspase-1−/− CKD mice compared with that in WT CKD mice.
FIG. 31D depicts results showing vessel lumen stenosis is increased in WT CKD mice compared with WT sham; the vessel stenosis is decreased in caspase-1−/− CKD mice compared with that of WT CKD mice.

Caspase-1 Deficiency Significantly Decreases CKD-Promoted Neointimal Hyperplasia of the Carotid Artery Based on our results that inhibition of caspase-1 activity in VSMC partially corrects CKD patients' serum-induced downregulation of VSMC contractile markers, we hypothesized that caspase-1 activation in VSMC may decrease the VSMC "contractile" phenotype, promote VSMC migration and accelerate neointima hyperplasia of the artery. In order to test this hypothesis, we established a mouse carotid ligation model as previously reported (Kokubo et al., 2009, J Am Soc Nephrol 20:1236-45). Six WT CKD mice, eight caspase-1−/− CKD mice and seven WT sham mice underwent carotid ligation procedure, and were kept three weeks for histophotometric analysis. After preparing and staining the histological samples with the Verhoeff-Van Gieson staining (elastic fibers), the neointimal hyperplasia in each of these sections was analyzed. The results showed that the neointimal hyperplasia volumes are increased significantly in WT CKD mice from 239,775.07 μm$^3$ to 1,440,023.70 μm$^3$ in the sham surgery mice (p=0.0196) (FIG. 31A). In addition, the results showed that the neointimal hyperplasia volumes are significantly reduced by 5 folds in caspase-1−/− CKD mice to 71,069.97 μm$^3$ from 1,440,023.70 μm$^3$ in WT CKD mice (p=0.035) (FIG. 31B). Moreover, no differences were found in the neointimal hyperplasia volumes between WT sham mice and CKD caspase-1−/− mice. In order to consider the potential variations caused by the process of histological slides, we also calculated the neointimal hyperplasia to media ratio for each group of mice (FIG. 31C). The results showed that the neointimal hyperplasia/media volume ratio of the WT sham mice was 18.50 while that of the WT type CKD mice was 88.03. There were statistical differences between the ratios of WT sham and WT CKD mice; p=0.025. The neointimal hyperplasia/media volume ratio of the caspase-1−/− CKD mice was 17.98. Furthermore, there are statistical differences between WT CKD and caspase-1−/− CKD; p=0.023. In addition, the percentages of stenosis in carotid arteries were also examined (FIG. 31D). The results showed that WT sham mice were found to have lumen stenosis percentages of 19.24%. By comparison, WT CKD mice were found to have the lumen stenosis of 68.25 (p<0.001). In contrast to that of WT CKD mice, the lumen stenosis percentage of caspase-1−/− CKD mice was 22.37% (p<0.001). As the controls, no significant differences were found between the media volumes of WT CKD and that of caspase 1−/− CKD groups (FIG. 31E). These results demonstrated that caspase-1 deficiency significantly decreases CKD-promoted neointimal hyperplasia of the carotid artery, which suggests that caspase-1 plays a critical role in accelerating CKD-promoted neointima hyperplasia of the carotid artery.

Figure 32:
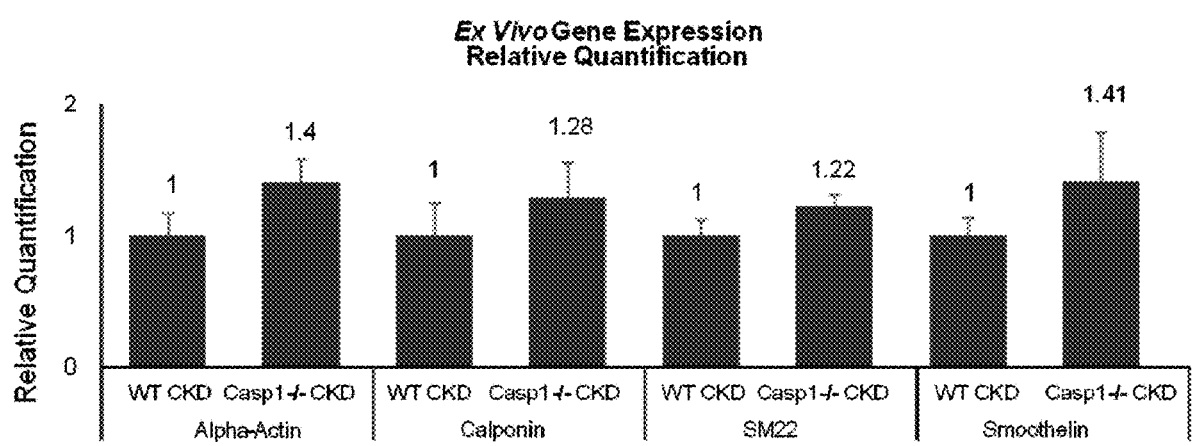
FIG. 32 depicts experimental results showing CKD decreases the expression of vascular smooth muscle cell contractile marker RNA transcripts in carotid artery in vivo, which is reversed by the deletion of caspase-1−/−. RNA was extracted from the carotid arteries of WT CKD mice and caspase-1−/− CKD mice. After reverse transcription, cDNA was subjected to analysis by quantitative PCR The expression of vascular smooth muscle contractile marker RNA transcripts such as alpha actin, calponin, SM22, and smoothelin was measured by quantitative RT-PCR using the Applied Biosystems 7500, Taqman primers and probes. The expression of smooth muscle contractile markers was increased in the carotid arteries of caspase-1−/− CKD mice in comparison to that of WT CKD mice.

Caspase-1 Deficiency Rescues CKD-Decreased Expression of Contractile Vascular Smooth Muscle Markers in NH Lesion In order to determine the molecular mechanism underlying the phenomenon we hypothesized that caspase-1 deficiency inhibits neointima hyperplasia by preserving the expression of contractile smooth muscle marker genes of VSMC based on our results that caspase-1 deficiency significantly decreases CKD-promoted neointimal hyperplasia of the carotid artery (FIG. 31), and that caspase-1 inhibition partially corrects the CKD patients' sera-induced downregulation of VSMC contractile gene markers (FIG. 29). To examine this hypothesis, we extracted RNAs from carotid samples and performed reverse transcription followed by quantitative PCR to measure the expressions of contractile smooth muscle markers that include alpha actin, calponin, SM22, and smoothelin (FIG. 32). The results showed that the relative quantification of alpha actin in caspase-1−/− CKD mice was 1.4 fold when compared to that of WT CKD mice. The relative expressions of calponin (1.28 folds), SM22 (1.22 folds), and smoothelin (1.41 folds) were all elevated in caspase-1−/− CKD mice when compared to that of the carotid artery samples of WT CKD mice. The results suggest that caspase-1 deficiency inhibits neointima hyperplasia via the preservation of the contractile VSMC marker genes expression.

Caspase-1 Deficiency Decreases $\alpha v \beta 3$ Integrin Expression

Figures 33A, 33B:
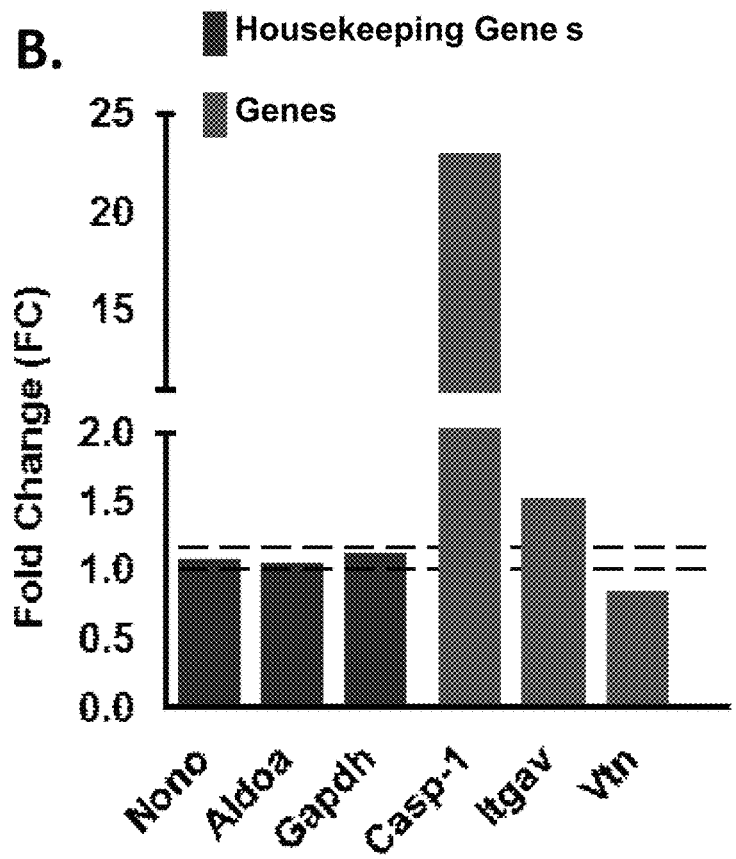
FIG. 33A and FIG. 33B, depicts experimental results showing Integrin alpha V mRNA is higher in WT mice than caspase-1−/− mice after feeding with high fat diet for 16 weeks.

As we pointed out in our previous review, $\alpha v \beta 3$ integrin blockade led to a significant reduction in neointimal lesion formation (Kokubo et al., 2007, J Vasc Surg, 45:A33-8), which suggested that $\alpha v \beta 3$ integrin and its ligand vitronectin mediate VSMC migration in NH formation. We hypothesized that caspase-1 promotes the expression of $\alpha v \beta 3$ integrin, the vitronectin receptor, in order to determine a mechanism underlying VSMC migration into the neointima. To test this hypothesis, we wanted to determine whether the expression of $\alpha v \beta 3$ integrin is decreased in any caspase-1 deficient tissues. By the analysis of the microarray data deposited in the NIH-GEO Profile database, we found that caspase-1 expression in WT mouse tissues is 22 folds higher than that of caspase-1 gene knock-out tissue (p<0.01) (FIG. 33), which suggests that 1) the tissue mRNA sample preparations of caspase-1−/− mice and WT control mice are correct; 2) the expressions of the three housekeeping genes (gapdh, aldoa, and nono) in the microarrays of caspase-1−/− mice versus WT control mice are very similar with a confidence interval (x±2 standard deviations) of 1.07±0.08 that further suggests that the tissue mRNA sample preparations of caspase-1−/− mice and WT control mice are of high quality; and 3) the expression of $\alpha v$ integrin in WT mouse tissue is 1.53 folds higher than that in caspase-1−/− mouse tissues (p<0.0247) whereas the expression of the $\alpha v \beta 3$ integrin ligand vitronectin in WT tissue is −1.19 folds higher than that in caspase-1−/− mouse tissues (p<0.1910). Importantly, $\alpha v \beta 3$ integrin is a heterodimer of $\alpha v$ and $\beta 3$ subunits (Desgrosellier et al., 2010, Nat Rev Vancer 10:9-22). We did not find significant changes of 33 integrin expression induced by caspase-1 depletion. However, when we analyzed the DNA sequence data in the NIH/NCBI-UniGene database, we found that 33 integrin RNA transcripts are expressed at a relative high level in human vessels (not shown). This finding suggests the possibility that highly expressed 33 integrin can associate with caspase-1 promoted $\alpha v$ integrin in order to upregulate the functional $\alpha v \beta 3$ integrin to mediate VSMC migration. In addition, $\alpha v$ integrin is a ubiquitously expressed protein in most tissues (see the RNA transcript expression profile at the NIH-NCBI-UniGene database Hs.436873). Thus, $\alpha v$ integrin expression is not significantly regulated by tissue differentiation signals but may possibly be regulated by pathological inflammatory signals. Since there are no microarray data sets from vessels available, our database mining results of $\alpha v \beta 3$ integrin RNA transcript expression with the microarray data set of GSE25205 from epidydimal white adipose tissue in the NIH-Geo Database were justified based on these considerations and manipulations. The results suggest that caspase-1 may promote the expression of $\alpha v \beta 3$ integrin, but the effect of caspase-1 on the expression of the $\alpha v \beta 3$ integrin ligand vitronectin is not statistically significant. These results suggest that caspase-1 potentially promotes neointima hyperplasia by enhancing the expression of the VSMC migration driving molecule $\alpha v \beta 3$ integrin.

Caspase-1 Pathway Plays a Critical Role in NH Formation and Serves as a Novel Therapeutic Target for the Suppression of CKD-Promoted NH It was reported that the bone marrow-derived inflammasome adaptor protein apoptosis-associated speck-like protein containing CARD (ASC) is critical for neointima formation after vascular injury (Yajima et al., 2008, Circulation 117:3079-87), which, however, did not report the role of vascular residential cell (for example, VSMC) expressed ASC. It has also been reported that caspase-1 inflammasome plays an important role in pulmonary vascular remodeling (Villegas et al., 2013, Antioxid Redox Signal 18:1753-64), atherosclerosis (Duewell et al., 2010, Nature 464:1357-61) and the pathogenesis of kidney disease (Kumar et al., 1997, Cirulcation 96:4333-42). However, an important question remains to be addressed: whether caspase-1 plays a critical role in promoting CKD-induced VSMC phenotypic switch from "contractile" to "synthetic" and the development of NH. The combination of CKD mouse model and the left carotid artery ligation-induced NH model, caspase-1−/− mice and CKD patients sera-stimulated HVSMC were used to determine whether caspase-1 plays any role in NH formation. We made the following findings: 1) Caspase-1 inhibition partially corrects CKD patients' sera-induced downregulation of VSMC contractile markers; 2) BUN level is not significantly different in WT CKD mice versus caspase-1−/− CKD mice; 3) Caspase-1 deficiency significantly decreases CKD-promoted neointimal hyperplasia of the carotid artery; 4) mechanistically, Caspase-1 deficiency rescues CKD-induced downregulation of VSMC contractile markers in NH lesion; and 5) Caspase-1 deficiency decreases the expression of the VSMC migration molecule $\alpha v \beta 3$ integrin. Our results suggest that the caspase-1 pathway senses CKD-elevated metabolic wastes and promotes the switch from the VSMC "contractile" phenotype to "synthetic" phenotype both in vitro and in vivo. CKD promotes caspase-1 dependent NH formation in the left carotid artery via a decrease in the expression of VSMC contractile phenotypic markers and an increase in the expression of VSMC migration molecule αvβ3 integrin.

Figure 34:
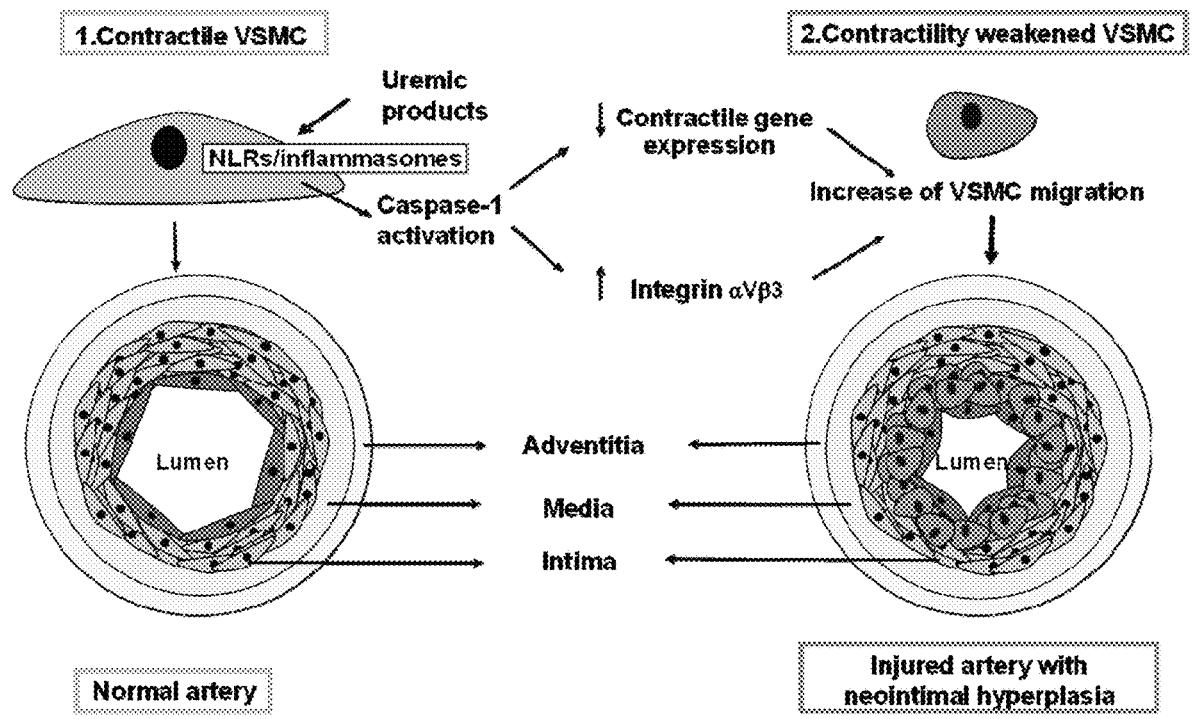
FIG. 34 depicts a schematic representation of a new working model about the role of caspase-1 in facilitating the development of CKD-promoted neointimal hyperplasia. The Nod-like receptors (NLRs)/inflammasomes pathway in the contractile VSMCs can sense the uremic toxic products as the metabolic danger signal-associated molecular patterns (DAMPs) in a CKD-state, which consequently activates caspase-1. The activation of caspase-1 promotes the maturation and secretion of proinflammatory cytokines IL-1b and IL-18, decreases the expression of VSMC contractile markers, and presumably makes VSMCs switch to synthetic phenotype and proliferation. The caspase-1 activation in the contractile weakened VSMCs increases the expression of Integrin αvβ3 also, which mediates the formation of neointimal hyperplasia induced by inward remodeling due to the migration of these VSMCs, which leads to the development of stenotic arterial lesion, occlusion of arterial lumen, and causes blood flow obstruction.

Our results suggest that caspase-1 depletion significantly decreases CKD-promoted neointima hyperplasia but does not cause significant changes in the media volumes of the NH lesion arteries. Once again, our results demonstrate that CKD-promoted NH is an inward remodeling process involved in the migration and proliferation of VSMC primarily in the tunica intima, that are adjacent to the intima but not distal to the intima, which results in the thickening of arterial walls and a decreased arterial lumen space. The mechanisms underlying the initiation of VSMC migration and the switch from "contractile" to "synthetic" phenotype in response to CKD still remain unknown. Recent reports demonstrated that TLR work in synergy with cytosolic sensing receptor families such as NLR in recognizing endogenous DAMP and in mediating the upregulation and activation of a range of inflammatory genes (Yin et al., 2013, Front Biosci 18:638-49). Our results presented here have clearly demonstrated that the caspase-1 pathway serves as the mechanisms underlying the initiation of VSMC migration and the switch from "contractile" to "synthetic" VSMC phenotypes that are responsive to CKD-elevated metabolic danger signals since caspase-1 deficiency completely inhibits CKD-promoted NH formation. Since the two processes of VSMC phenotypes switch, e.g., it can be inferred that a decrease in the VSMC "contractile" phenotype and increase in the VSMC "synthetic" phenotype is linked (Alexander and Owens, 2012, Annu Rev Physiol 74:13-40), which further justifies our focus on caspase-1 inhibition of CKD-induced decrease in VSMC "contractile" phenotype. Our results have also elucidated the detailed molecular mechanisms and demonstrated that caspase-1 enhances CKD-decreased expressions of VSMC contractile markers and CKD-increased expression of VSMC migration molecule αvβ3 integrin. Our new working model presented in FIG. 34 highlights these significant findings.

Patients that undergo hemodialysis-utilizing AVF often need to be surgically re-intervened in order to correct stenotic lesions (Lee et al., 2009, Adv Chronic Kidney Dis 15:329-38). These surgically repeated interventions increase the morbidity and mortality in CKD patients that receive dialysis (Lee et al., 2002, Am J Kidney Dis 40:611-22). The major cause of vascular access failure in AVF is due to neointimal hyperplasia (Lee et al., 2009, Adv Chronic Kidney Dis 15:329-38), which is accelerated by the uremic state in CKD (Langer et al., 2010, Kidney Int 78:1312-21; Kokubo et al., 2009, J Am Soc Nephrol 20:1236-45). However, no effective therapies are available to inhibit the initiation and progression of NH associated with CKD. For the first time, our results have demonstrated that the caspase-1 pathway plays a critical role in NH formation, and that caspase-1 serves as a novel therapeutic target for the suppression of CKD-promoted NH and various vascular pathologies including atherosclerosis, hypertension and post-angioplasty restenosis (Regan et al., 2000, J Cin Invest 106:1139-47; Owens et al., 2004, Physiol Rev 84:767-801).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An inhibitor of caspase-1 activity comprising a non-cleavable Sirt1 peptide inhibitor, wherein the non-cleavable Sirt1 peptide inhibitor is at least one of:

a) Mouse nc-Sirt1:

(SEQ ID NO: 1)

RQIKIWFQNRRMKWKKGYRDNLLLTAGLLTNGFHSC;
or b) Human nc-Sirt1:

(SEQ ID NO: 2)

RQIKIWFQNRRMKWKKGYRDNLLFGAEIITNGFHSC.

* * * * *

SEQUENCE LISTING

```
<160> NUMBER OF SEQ ID NOS: 34

<210> SEQ ID NO 1
<211> LENGTH: 36
<212> TYPE: PRT
<213> ORGANISM: Mus musculus

<400> SEQUENCE: 1

Arg Gln Ile Lys Ile Trp Phe Gln Asn Arg Arg Met Lys Trp Lys Lys
1               5                   10                  15

Gly Tyr Arg Asp Asn Leu Leu Leu Thr Ala Gly Leu Leu Thr Asn Gly
            20                  25                  30

Phe His Ser Cys
        35

<210> SEQ ID NO 2
<211> LENGTH: 36
<212> TYPE: PRT
<213> ORGANISM: Homo sapiens

<400> SEQUENCE: 2

Arg Gln Ile Lys Ile Trp Phe Gln Asn Arg Arg Met Lys Trp Lys Lys
1               5                   10                  15

Gly Tyr Arg Asp Asn Leu Leu Phe Gly Ala Glu Ile Ile Thr Asn Gly
            20                  25                  30

Phe His Ser Cys
        35
```

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized

<400> SEQUENCE: 3
gcctagccga gggagagccg                                             20

<210> SEQ ID NO 4
<211> LENGTH: 22
<212> TYPE: DNA
<213> ORGANISM: Artificial Sequence
<220> FEATURE:
<223> OTHER INFORMATION: Chemically synthesized

<400> SEQUENCE: 4
tgtgacttgg gagctctgca gc                                          22

<210> SEQ ID NO 5
<211> LENGTH: 18
<212> TYPE: DNA
<213> ORGANISM: Artificial Sequence
<220> FEATURE:
<223> OTHER INFORMATION: Chemically synthesized

<400> SEQUENCE: 5
gccgccccga ctgcatct                                               18

<210> SEQ ID NO 6
<211> LENGTH: 21
<212> TYPE: DNA
<213> ORGANISM: Artificial Sequence
<220> FEATURE:
<223> OTHER INFORMATION: Chemically synthesized

<400> SEQUENCE: 6
atggcacacc acagatatcg g                                           21

<210> SEQ ID NO 7
<211> LENGTH: 24
<212> TYPE: DNA
<213> ORGANISM: Artificial Sequence
<220> FEATURE:
<223> OTHER INFORMATION: Chemically synthesized

<400> SEQUENCE: 7
tgctaaagcg catgctccag actg                                        24

<210> SEQ ID NO 8
<211> LENGTH: 21
<212> TYPE: DNA
<213> ORGANISM: Artificial Sequence
<220> FEATURE:
<223> OTHER INFORMATION: Chemically synthesized

<400> SEQUENCE: 8
gagacatata agggagaagg g                                           21

<210> SEQ ID NO 9
<211> LENGTH: 21
<212> TYPE: DNA
<213> ORGANISM: Artificial Sequence
<220> FEATURE:
<223> OTHER INFORMATION: Chemically synthesized

```
<400> SEQUENCE: 9
aagtgactgc tccattcgga a                                              21

<210> SEQ ID NO 10
<211> LENGTH: 22
<212> TYPE: DNA
<213> ORGANISM: Artificial Sequence
<220> FEATURE:
<223> OTHER INFORMATION: Chemically synthesized

<400> SEQUENCE: 10
ctccgagaac agctggtctt ct                                             22

<210> SEQ ID NO 11
<211> LENGTH: 20
<212> TYPE: DNA
<213> ORGANISM: Artificial Sequence
<220> FEATURE:
<223> OTHER INFORMATION: Chemically synthesized

<400> SEQUENCE: 11
tgaagaggag tggatgggtt                                                20

<210> SEQ ID NO 12
<211> LENGTH: 20
<212> TYPE: DNA
<213> ORGANISM: Artificial Sequence
<220> FEATURE:
<223> OTHER INFORMATION: Chemically synthesized

<400> SEQUENCE: 12
ttcaatgcac tggaatctgc                                                20

<210> SEQ ID NO 13
<211> LENGTH: 22
<212> TYPE: DNA
<213> ORGANISM: Artificial Sequence
<220> FEATURE:
<223> OTHER INFORMATION: Chemically synthesized

<400> SEQUENCE: 13
atggacgcct tggacctcac cg                                             22

<210> SEQ ID NO 14
<211> LENGTH: 22
<212> TYPE: DNA
<213> ORGANISM: Artificial Sequence
<220> FEATURE:
<223> OTHER INFORMATION: Chemically synthesized

<400> SEQUENCE: 14
tggcttggct gccgactgag ga                                             22

<210> SEQ ID NO 15
<211> LENGTH: 21
<212> TYPE: DNA
<213> ORGANISM: Artificial Sequence
<220> FEATURE:
<223> OTHER INFORMATION: Chemically synthesized

<400> SEQUENCE: 15
agctcctcag gcagtgcagg a                                              21

<210> SEQ ID NO 16
```

-continued

```
<211> LENGTH: 20
<212> TYPE: DNA
<213> ORGANISM: Artificial Sequence
<220> FEATURE:
<223> OTHER INFORMATION: Chemically synthesized

<400> SEQUENCE: 16
agagcaagac gtgtgcggct                                                 20

<210> SEQ ID NO 17
<211> LENGTH: 21
<212> TYPE: DNA
<213> ORGANISM: Artificial Sequence
<220> FEATURE:
<223> OTHER INFORMATION: Chemically synthesized

<400> SEQUENCE: 17
acagatgaag tgctccttcc a                                               21

<210> SEQ ID NO 18
<211> LENGTH: 21
<212> TYPE: DNA
<213> ORGANISM: Artificial Sequence
<220> FEATURE:
<223> OTHER INFORMATION: Chemically synthesized

<400> SEQUENCE: 18
gtcggagatt cgtagctgga t                                               21

<210> SEQ ID NO 19
<211> LENGTH: 20
<212> TYPE: DNA
<213> ORGANISM: Artificial Sequence
<220> FEATURE:
<223> OTHER INFORMATION: Chemically synthesized

<400> SEQUENCE: 19
accttctaca atgagctgcg                                                 20

<210> SEQ ID NO 20
<211> LENGTH: 20
<212> TYPE: DNA
<213> ORGANISM: Artificial Sequence
<220> FEATURE:
<223> OTHER INFORMATION: Chemically synthesized

<400> SEQUENCE: 20
cctggatagc aagtacatgg                                                 20

<210> SEQ ID NO 21
<211> LENGTH: 22
<212> TYPE: DNA
<213> ORGANISM: Artificial Sequence
<220> FEATURE:
<223> OTHER INFORMATION: Chemically synthesized

<400> SEQUENCE: 21
ccctcaagtt ttgcccttta ga                                              22

<210> SEQ ID NO 22
<211> LENGTH: 22
<212> TYPE: DNA
<213> ORGANISM: Artificial Sequence
<220> FEATURE:
<223> OTHER INFORMATION: Chemically synthesized

<400> SEQUENCE: 22
```
ccctcggaga aagatgttga aa                                        22

<210> SEQ ID NO 23
<211> LENGTH: 21
<212> TYPE: DNA
<213> ORGANISM: Artificial Sequence
<220> FEATURE:
<223> OTHER INFORMATION: Chemically synthesized

<400> SEQUENCE: 23
gttctctaat gtctccgagg c                                         21

<210> SEQ ID NO 24
<211> LENGTH: 20
<212> TYPE: DNA
<213> ORGANISM: Artificial Sequence
<220> FEATURE:
<223> OTHER INFORMATION: Chemically synthesized

<400> SEQUENCE: 24
cttcagaggc aggaaacagg                                           20

<210> SEQ ID NO 25
<211> LENGTH: 21
<212> TYPE: DNA
<213> ORGANISM: Artificial Sequence
<220> FEATURE:
<223> OTHER INFORMATION: Chemically synthesized

<400> SEQUENCE: 25
gcaaaggaca ctggaaaaga g                                         21

<210> SEQ ID NO 26
<211> LENGTH: 23
<212> TYPE: DNA
<213> ORGANISM: Artificial Sequence
<220> FEATURE:
<223> OTHER INFORMATION: Chemically synthesized

<400> SEQUENCE: 26
tcaaagggat acacattagg gac                                       23

<210> SEQ ID NO 27
<211> LENGTH: 21
<212> TYPE: DNA
<213> ORGANISM: Artificial Sequence
<220> FEATURE:
<223> OTHER INFORMATION: Chemically synthesized

<400> SEQUENCE: 27
gctggagaac ttgcgtttaa g                                         21

<210> SEQ ID NO 28
<211> LENGTH: 21
<212> TYPE: DNA
<213> ORGANISM: Artificial Sequence
<220> FEATURE:
<223> OTHER INFORMATION: Chemically synthesized

<400> SEQUENCE: 28
agataaggct tcacactgga c                                         21

<210> SEQ ID NO 29
<211> LENGTH: 26
<212> TYPE: DNA

<210> SEQ ID NO 29
<211> LENGTH: 26
<212> TYPE: DNA
<213> ORGANISM: Artificial Sequence
<220> FEATURE:
<223> OTHER INFORMATION: Chemically synthesized

<400> SEQUENCE: 29
gaggccggtg ctgagtatgt cgtgga                                26

<210> SEQ ID NO 30
<211> LENGTH: 25
<212> TYPE: DNA
<213> ORGANISM: Artificial Sequence
<220> FEATURE:
<223> OTHER INFORMATION: Chemically synthesized

<400> SEQUENCE: 30
cacacccatc acaaactggg ggcat                                 25

<210> SEQ ID NO 31
<211> LENGTH: 21
<212> TYPE: DNA
<213> ORGANISM: Artificial Sequence
<220> FEATURE:
<223> OTHER INFORMATION: Chemically synthesized

<400> SEQUENCE: 31
cgcttgatga ctcagccgga a                                     21

<210> SEQ ID NO 32
<211> LENGTH: 22
<212> TYPE: DNA
<213> ORGANISM: Artificial Sequence
<220> FEATURE:
<223> OTHER INFORMATION: Chemically synthesized

<400> SEQUENCE: 32
agttgagggg actttcccag gc                                    22

<210> SEQ ID NO 33
<211> LENGTH: 736
<212> TYPE: PRT
<213> ORGANISM: Mus musculus

<400> SEQUENCE: 33

Met Ala Asp Glu Val Ala Leu Ala Leu Gln Ala Ala Gly Ser Pro Ser
1               5                   10                  15

Ala Ala Ala Ala Met Glu Ala Ala Ser Gln Pro Ala Asp Glu Pro Leu
            20                  25                  30

Arg Lys Arg Pro Arg Arg Asp Gly Pro Gly Leu Gly Arg Ser Pro Gly
        35                  40                  45

Glu Pro Ser Ala Ala Val Ala Pro Ala Ala Gly Cys Glu Ala Ala
    50                  55                  60

Ser Ala Ala Ala Pro Ala Ala Leu Trp Arg Glu Ala Ala Gly Ala Ala
65                  70                  75                  80

Ala Ser Ala Glu Arg Glu Ala Pro Ala Thr Ala Val Ala Gly Asp Gly
                85                  90                  95

Asp Asn Gly Ser Gly Leu Arg Arg Glu Pro Arg Ala Ala Asp Asp Phe
            100                 105                 110

Asp Asp Asp Glu Gly Glu Gly Glu Asp Glu Ala Ala Ala Ala Ala Ala
        115                 120                 125

Ala Ala Ala Ile Gly Tyr Arg Asp Asn Leu Leu Leu Thr Asp Gly Leu
    130                 135                 140

```
Leu Thr Asn Gly Phe His Ser Cys Glu Ser Asp Asp Asp Arg Thr
145                 150                 155                 160

Ser His Ala Ser Ser Ser Asp Trp Thr Pro Arg Pro Arg Ile Gly Pro
            165                 170                 175

Tyr Thr Phe Val Gln Gln His Leu Met Ile Gly Thr Asp Pro Arg Thr
            180                 185                 190

Ile Leu Lys Asp Leu Leu Pro Glu Thr Ile Pro Pro Glu Leu Asp
        195                 200                 205

Asp Met Thr Leu Trp Gln Ile Val Ile Asn Ile Leu Ser Glu Pro Pro
            210                 215                 220

Lys Arg Lys Lys Arg Lys Asp Ile Asn Thr Ile Glu Asp Ala Val Lys
225                 230                 235                 240

Leu Leu Gln Glu Cys Lys Lys Ile Ile Val Leu Thr Gly Ala Gly Val
            245                 250                 255

Ser Val Ser Cys Gly Ile Pro Asp Phe Arg Ser Arg Asp Gly Ile Tyr
            260                 265                 270

Ala Arg Leu Ala Val Asp Phe Pro Asp Leu Pro Asp Pro Gln Ala Met
            275                 280                 285

Phe Asp Ile Glu Tyr Phe Arg Lys Asp Pro Arg Pro Phe Phe Lys Phe
290                 295                 300

Ala Lys Glu Ile Tyr Pro Gly Gln Phe Gln Pro Ser Leu Cys His Lys
305                 310                 315                 320

Phe Ile Ala Leu Ser Asp Lys Glu Gly Lys Leu Leu Arg Asn Tyr Thr
                325                 330                 335

Gln Asn Ile Asp Thr Leu Glu Gln Val Ala Gly Ile Gln Arg Ile Leu
            340                 345                 350

Gln Cys His Gly Ser Phe Ala Thr Ala Ser Cys Leu Ile Cys Lys Tyr
            355                 360                 365

Lys Val Asp Cys Glu Ala Val Arg Gly Asp Ile Phe Asn Gln Val Val
370                 375                 380

Pro Arg Cys Pro Arg Cys Pro Ala Asp Glu Pro Leu Ala Ile Met Lys
385                 390                 395                 400

Pro Glu Ile Val Phe Phe Gly Glu Asn Leu Pro Glu Gln Phe His Arg
                405                 410                 415

Ala Met Lys Tyr Asp Lys Asp Glu Val Asp Leu Leu Ile Val Ile Gly
            420                 425                 430

Ser Ser Leu Lys Val Arg Pro Val Ala Leu Ile Pro Ser Ser Ile Pro
        435                 440                 445

His Glu Val Pro Gln Ile Leu Ile Asn Arg Glu Pro Leu Pro His Leu
    450                 455                 460

His Phe Asp Val Glu Leu Leu Gly Asp Cys Asp Val Ile Ile Asn Glu
465                 470                 475                 480

Leu Cys His Arg Leu Gly Gly Glu Tyr Ala Lys Leu Cys Cys Asn Pro
                485                 490                 495

Val Lys Leu Ser Glu Ile Thr Glu Lys Pro Pro Arg Pro Gln Lys Glu
            500                 505                 510

Leu Val His Leu Ser Glu Leu Pro Pro Thr Pro Leu His Ile Ser Glu
        515                 520                 525

Asp Ser Ser Ser Pro Glu Arg Thr Val Pro Gln Asp Ser Ser Val Ile
    530                 535                 540

Ala Thr Leu Val Asp Gln Ala Thr Asn Asn Asn Val Asn Asp Leu Glu
545                 550                 555                 560

Val Ser Glu Ser Ser Cys Val Glu Glu Lys Pro Gln Glu Val Gln Thr
```

```
                        565                 570                 575
Ser Arg Asn Val Glu Asn Ile Asn Val Glu Asn Pro Asp Phe Lys Ala
            580                 585                 590

Val Gly Ser Ser Thr Ala Asp Lys Asn Glu Arg Thr Ser Val Ala Glu
            595                 600                 605

Thr Val Arg Lys Cys Trp Pro Asn Arg Leu Ala Lys Glu Gln Ile Ser
            610                 615                 620

Lys Arg Leu Glu Gly Asn Gln Tyr Leu Phe Val Pro Asn Arg Tyr
625                 630                 635                 640

Ile Phe His Gly Ala Glu Val Tyr Ser Asp Ser Glu Asp Val Leu
            645                 650                 655

Ser Ser Ser Ser Cys Gly Ser Asn Ser Asp Ser Gly Thr Cys Gln Ser
            660                 665                 670

Pro Ser Leu Glu Glu Pro Leu Glu Asp Glu Ser Glu Ile Glu Glu Phe
            675                 680                 685

Tyr Asn Gly Leu Glu Asp Asp Thr Glu Arg Pro Glu Cys Ala Gly Gly
            690                 695                 700

Ser Gly Phe Gly Ala Asp Gly Asp Gln Glu Val Asn Glu Ala
705                 710                 715                 720

Ile Ala Thr Arg Gln Glu Leu Thr Asp Val Asn Tyr Pro Ser Asp Lys
            725                 730                 735

<210> SEQ ID NO 34
<211> LENGTH: 747
<212> TYPE: PRT
<213> ORGANISM: Homo sapiens

<400> SEQUENCE: 34

Met Ala Asp Glu Ala Ala Leu Ala Leu Gln Pro Gly Gly Ser Pro Ser
1               5                   10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Leu Trp Arg Glu Ala Glu
65              70                  75                  80

Ala Glu Ala Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205
```

```
Thr Ile Pro Pro Pro Glu Leu Asp Asp Met Thr Leu Trp Gln Ile Val
    210                 215                 220
Ile Asn Ile Leu Ser Glu Pro Pro Lys Arg Lys Lys Arg Lys Asp Ile
225                 230                 235                 240
Asn Thr Ile Glu Asp Ala Val Lys Leu Leu Gln Glu Cys Lys Lys Ile
                245                 250                 255
Ile Val Leu Thr Gly Ala Gly Val Ser Val Ser Cys Gly Ile Pro Asp
            260                 265                 270
Phe Arg Ser Arg Asp Gly Ile Tyr Ala Arg Leu Ala Val Asp Phe Pro
        275                 280                 285
Asp Leu Pro Asp Pro Gln Ala Met Phe Asp Ile Glu Tyr Phe Arg Lys
    290                 295                 300
Asp Pro Arg Pro Phe Phe Lys Phe Ala Lys Glu Ile Tyr Pro Gly Gln
305                 310                 315                 320
Phe Gln Pro Ser Leu Cys His Lys Phe Ile Ala Leu Ser Asp Lys Glu
                325                 330                 335
Gly Lys Leu Leu Arg Asn Tyr Thr Gln Asn Ile Asp Thr Leu Glu Gln
            340                 345                 350
Val Ala Gly Ile Gln Arg Ile Ile Gln Cys His Gly Ser Phe Ala Thr
        355                 360                 365
Ala Ser Cys Leu Ile Cys Lys Tyr Lys Val Asp Cys Glu Ala Val Arg
    370                 375                 380
Gly Asp Ile Phe Asn Gln Val Val Pro Arg Cys Pro Arg Cys Pro Ala
385                 390                 395                 400
Asp Glu Pro Leu Ala Ile Met Lys Pro Glu Ile Val Phe Phe Gly Glu
                405                 410                 415
Asn Leu Pro Glu Gln Phe His Arg Ala Met Lys Tyr Asp Lys Asp Glu
            420                 425                 430
Val Asp Leu Leu Ile Val Ile Gly Ser Ser Leu Lys Val Arg Pro Val
        435                 440                 445
Ala Leu Ile Pro Ser Ser Ile Pro His Glu Val Pro Gln Ile Leu Ile
    450                 455                 460
Asn Arg Glu Pro Leu Pro His Leu His Phe Asp Val Glu Leu Leu Gly
465                 470                 475                 480
Asp Cys Asp Val Ile Ile Asn Glu Leu Cys His Arg Leu Gly Gly Glu
                485                 490                 495
Tyr Ala Lys Leu Cys Cys Asn Pro Val Lys Leu Ser Glu Ile Thr Glu
            500                 505                 510
Lys Pro Pro Arg Thr Gln Lys Glu Leu Ala Tyr Leu Ser Glu Leu Pro
        515                 520                 525
Pro Thr Pro Leu His Val Ser Glu Asp Ser Ser Ser Pro Glu Arg Thr
    530                 535                 540
Ser Pro Pro Asp Ser Ser Val Ile Val Thr Leu Leu Asp Gln Ala Ala
545                 550                 555                 560
Lys Ser Asn Asp Asp Leu Asp Val Ser Glu Ser Lys Gly Cys Met Glu
                565                 570                 575
Glu Lys Pro Gln Glu Val Gln Thr Ser Arg Asn Val Glu Ser Ile Ala
            580                 585                 590
Glu Gln Met Glu Asn Pro Asp Leu Lys Asn Val Gly Ser Ser Thr Gly
        595                 600                 605
Glu Lys Asn Glu Arg Thr Ser Val Ala Gly Thr Val Arg Lys Cys Trp
    610                 615                 620
Pro Asn Arg Val Ala Lys Glu Gln Ile Ser Arg Arg Leu Asp Gly Asn
```

-continued

```
          625              630                 635               640
Gln Tyr Leu Phe Leu Pro Pro Asn Arg Tyr Ile Phe His Gly Ala Glu
                    645                 650              655

Val Tyr Ser Asp Ser Glu Asp Val Leu Ser Ser Ser Cys Gly
            660             665             670

Ser Asn Ser Asp Ser Gly Thr Cys Gln Ser Pro Ser Leu Glu Glu Pro
            675             680             685

Met Glu Asp Glu Ser Glu Ile Glu Glu Phe Tyr Asn Gly Leu Glu Asp
    690             695             700

Glu Pro Asp Val Pro Glu Arg Ala Gly Gly Ala Gly Phe Gly Thr Asp
705             710             715             720

Gly Asp Asp Gln Glu Ala Ile Asn Glu Ala Ile Ser Val Lys Gln Glu
                725             730             735

Val Thr Asp Met Asn Tyr Pro Ser Asn Lys Ser
            740             745
```